(12) United States Patent
Rand

(10) Patent No.: US 12,203,139 B2
(45) Date of Patent: Jan. 21, 2025

(54) SYSTEMS AND METHODS FOR DETECTING MULTI-MOLECULE BIOMARKERS

(71) Applicant: Tempus AI, Inc., Chicago, IL (US)

(72) Inventor: Timothy Rand, Chicago, IL (US)

(73) Assignee: TEMPUS AI, INC., Chicago, IL (US)

( * ) Notice: Subject to any disclaimer, the term of this patent is extended or adjusted under 35 U.S.C. 154(b) by 0 days.

(21) Appl. No.: 18/160,918

(22) Filed: Jan. 27, 2023

(65) Prior Publication Data

US 2023/0323458 A1  Oct. 12, 2023

Related U.S. Application Data

(62) Division of application No. 17/566,088, filed on Dec. 30, 2021, now Pat. No. 11,613,783.

(60) Provisional application No. 63/133,035, filed on Dec. 31, 2020.

(51) Int. Cl.
C12Q 1/68 (2018.01)
C12P 19/34 (2006.01)
C12Q 1/6813 (2018.01)
C12Q 1/6883 (2018.01)

(52) U.S. Cl.
CPC ......... C12Q 1/6883 (2013.01); C12Q 1/6813 (2013.01)

(58) Field of Classification Search
CPC ... C12Q 1/6883; C12Q 1/6804; C12Q 1/6813
See application file for complete search history.

(56) References Cited

U.S. PATENT DOCUMENTS

| | | | |
|---|---|---|---|
| 4,458,066 A | 7/1984 | Caruthers et al. | |
| 4,683,195 A | 7/1987 | Mullis et al. | |
| 4,683,202 A | 7/1987 | Mullis | |
| 5,494,810 A | 2/1996 | Barany et al. | |
| 10,395,772 B1 | 8/2019 | Lucas et al. | |
| 10,902,952 B2 | 1/2021 | Lucas et al. | |
| 10,957,041 B2 | 3/2021 | Yip et al. | |
| 10,975,445 B2 | 4/2021 | Venkat et al. | |
| 11,043,283 B1 | 6/2021 | Bell et al. | |
| 11,043,304 B2 | 6/2021 | Lozac'hmeur et al. | |
| 11,081,210 B2 | 8/2021 | Perera | |
| 11,145,416 B1 | 10/2021 | Hafez et al. | |
| 11,211,144 B2 | 12/2021 | Zhu et al. | |
| 11,211,147 B2 | 12/2021 | Finkle et al. | |
| 11,414,700 B2 | 8/2022 | Perera et al. | |
| 2014/0357500 A1 | 12/2014 | Vigneault et al. | |
| 2016/0305947 A1 | 10/2016 | Pierce et al. | |
| 2018/0312901 A1 | 11/2018 | Fredriksson et al. | |
| 2018/0340939 A1* | 11/2018 | Gaublomme | G01N 33/6845 |
| 2019/0292581 A1 | 9/2019 | Egidio et al. | |
| 2020/0075169 A1 | 3/2020 | Lau et al. | |
| 2020/0087707 A1 | 3/2020 | Engreitz | |
| 2020/0098448 A1 | 3/2020 | Shah et al. | |
| 2020/0118644 A1 | 4/2020 | Khan et al. | |
| 2020/0135303 A1 | 4/2020 | Barber | |
| 2020/0210852 A1 | 7/2020 | Igartua et al. | |
| 2020/0211716 A1 | 7/2020 | Efkofsky et al. | |
| 2020/0258601 A1 | 8/2020 | Lau | |
| 2020/0335102 A1 | 10/2020 | Lefkofsky et al. | |
| 2020/0365232 A1 | 11/2020 | Jaros et al. | |
| 2020/0365268 A1 | 11/2020 | Michuda et al. | |
| 2020/0381087 A1 | 12/2020 | Ozeran et al. | |
| 2020/0395097 A1 | 12/2020 | Chang et al. | |
| 2021/0057042 A1 | 2/2021 | Beaubier et al. | |
| 2021/0057071 A1 | 2/2021 | Barber et al. | |
| 2021/0090694 A1 | 3/2021 | Colley et al. | |
| 2021/0098078 A1 | 4/2021 | Lozac'hmeur et al. | |
| 2021/0115511 A1 | 4/2021 | Blidner | |
| 2021/0118526 A1 | 4/2021 | Barber | |
| 2021/0118559 A1 | 4/2021 | Lefkofsky | |
| 2021/0151192 A1 | 5/2021 | Lucas et al. | |
| 2021/0155989 A1 | 5/2021 | Salahudeen et al. | |
| 2021/0172931 A1 | 6/2021 | Larsen et al. | |
| 2021/0269878 A1 | 9/2021 | Blidner | |
| 2021/0325308 A1 | 10/2021 | Kannan et al. | |
| 2021/0327536 A1 | 10/2021 | Lozac'hmeur et al. | |
| 2021/0343372 A1 | 11/2021 | Tell et al. | |
| 2021/0398617 A1 | 12/2021 | Finkle et al. | |
| 2022/0028482 A1 | 1/2022 | Bell et al. | |
| 2022/0059190 A1 | 2/2022 | Ahmed et al. | |
| 2022/0154284 A1 | 5/2022 | Lau et al. | |
| 2022/0208305 A1 | 6/2022 | Bontrager et al. | |

FOREIGN PATENT DOCUMENTS

| | | |
|---|---|---|
| WO | 2021081253 A1 | 4/2021 |
| WO | 2021113821 A1 | 6/2021 |
| WO | 2021168143 A1 | 8/2021 |

OTHER PUBLICATIONS

Ola Söderberg, et al. "Characterizing proteins and their interactions in cells and tissues using the in situ proximity ligation assay" Methods 45 (2008) 227-232 (Year: 2008).*

Perrine Cruaud, et al. "High-throughput sequencing of multiple amplicons for barcoding and integrative taxonomy" Sci. Rep. 7, 41948; pp. 1-12. (Year: 2017).*

Simon Fredriksson, et al. "Multiplexed protein detection by proximity ligation for cancer biomarker validation" Nature Methods, vol. 40, No. 4, Apr. 2007, pp. 327-329; Supp Table 2. (Year: 2007).*

Christina Greenwood, et al. "Proximity assays for sensitive quantification of proteins" Biomol Detect Quantif. Jun. 2015; 4: 10-16. (Year: 2015).*

Anders Stahlberg, et al. "Simple multiplexed PCR-based barcoding of DNA for ultrasensitive mutation detection by next-generation sequencing" Nat Protoc. Apr. 2017;12(4):664-682 (Year: 2017).*

(Continued)

Primary Examiner — Stephen T Kapushoc
(74) Attorney, Agent, or Firm — Quarles & Brady LLP

(57) ABSTRACT

The present disclosure provides methods, systems, compositions, and kits for the high-throughput detection of multi-molecule biomarkers in a biological sample. The disclosed methods, systems, compositions, and kits utilize antibody-oligonucleotide tags to detect two or more molecules that are in close proximity.

11 Claims, 18 Drawing Sheets

Specification includes a Sequence Listing.

(56) References Cited

OTHER PUBLICATIONS

Alles et al., Cell Fixation and Preservation for Droplet-Based Single-Cell Transcriptomics, BMC Biology, 2017, 15:44, pp. 1-14.
Beaucage et al., Deoxynucleoside Phosphoramidites—A New Class of Key Intermediates for Deoxypolynucleotide Synthesis, Tetrahedron Letters, 1981, 22(20):1859-1862.
Darmanis et al., ProteinSeq: High-Performance Proteomic Analyses by Proximity Ligation and Next Generation Sequencing, PloS ONE, 2011, 6(9):e25583, pp. 1-10.
Haque et al., A Practical Guide to Single-Cell RNA-sequencing for Biomedical Research and Clinical Applications, Genome Medicine, 2017, 9:75, pp. 1-12.
Kolodziejczyk et al., The Technology and Biology of Single-Cell RNA Sequencing, Molecular Cell, 2015, 58 (4):610-620.
Lundberg et al., Multiplexed Homogeneous Proximity Ligation Assays for High-throughput Protein Biomarker Research in Serological Material, Molecular & Cellular Proteomics, 2011, 10.4, pp. 1-10.
Owczarzy et al., Predicting Stability of DNA Duplexes in Solutions Containing Magnesium and Monovalent Cations, Biochemistry, 2008, 47(19):5336-5353.
Wetmur, DNA Probes: Applications of the Principles of Nucleic Acid Hybridization, Critical Reviews in Biochemistry and Molecular Biology, 1991, 26(3-4):227-259.
10X Genomics, Inc., Single Cell Protocols—Cell Preparation Guide, 2017, 22 pages.
PCT International Search Report and Written Opinion, PCT/US2021/073189, Mar. 15, 2022, 14 pages.
Ooi, Aik T., and David W. Ruff. "Simultaneous targeted detection of proteins and RNAs in single cells." Single Cell Methods: Sequencing and Proteomics (2019): 379-392.
Savas, Peter, et al. "Single-cell profiling of breast cancer T cells reveals a tissue-resident memory subset associated with improved prognosis." Nature medicine 24.7 (2018): 986-993.
Canady, Taylor D., et al. "Enhanced hybridization selectivity using structured GammaPNA probes." Molecules 25.4 (2020): 970.
Hammond, Maria, et al. "Profiling cellular protein complexes by proximity ligation with dual tag microarray readout." PLoS One 7.7 (2012): e40405.
Wik, Lotta, et al. "Proximity extension assay in combination with next-generation sequencing for high-throughput proteome-wide analysis." Molecular & Cellular Proteomics 20 (2021).
Darmanis, Spyros, et al. "ProteinSeq: high-performance proteomic analyses by proximity ligation and next generation sequencing." PloS one 6.9 (2011): e25583.
Hegazy, M. et al. Proximity Ligation Assay for Detecting Protein-Protein Interactions and Protein Modifications in Cells and Tissues In Situ. Current Protocols in Cell Biology 89(1):e115, 34 pages, 2020.
Olink, Pea—A High-Multiplex Immunoassay Technology with qPCR or NGS Readout, White Paper, 4 pages, Copyright 2020.
Trifilieff, P. et al. Detection of Antigen Interactions ex vivo by Proximity Ligation Assay: Endogenous Dopamine D2-Adenosine A2A Receptor Complexes in the Striatum. Biotechniques 51(2):111-118, 2011.

\* cited by examiner

Figure 1

Method 100

105: select or customize antibody-oligo tags

110: (optional) select or customize complementary splint oligo sequences

115: add antibody-oligo tags to biological specimen

116: (optional) remove unbound antibody-oligo tags from biological specimen

120: proximal antibody-oligo tags form proximity detection nucleic acid molecule 125: prepare sequencing library 130: generate sequencing data 135: detect proximity detection nucleic acid molecules in sequencing data 140: report multi-molecule biomarkers detected in specimen 145: (optional) report diagnoses, prognoses, and/or therapies and clinical trials associated with detected multi-molecule biomarkers 150: (optional) store results in a database

Figure 3A-L

A 10n for RE activity | BstXI | Spacer mol_ID | BC1
5'-tattgacgatccattggatCGNNNNNNNNNNtgcccgtctgcctt (SEQ ID NO:3)
cagacggaa cagacggaa (SEQ ID NO:4) cagacggaaNNNNNNNNNNTCGCCACGGTCgCACAGAGAATATGTGTAGAGGC-5' blocked | Spacer | BC2 | Spacer | R2
@BC1 | mol_ID | | mol_ID

Figure 3A-L (continued)

B
5'-tattgacgatCCATtgggTGCNNNNNNNNNNtgcacgtctgcctt (SEQ ID NO:3)

(SEQ ID NO:4) cagacggaaNNNNNNNNNNNCCCGACGGTCGGNNNNNNNNNNGACAGAATATGTGTAGAGGC-5'

· cagacggaa
· cagacggaa

C
5'-tattgacgatCCATtgggTGCNNNNNNNNNNtgcacgtctgcctt
   cagacggaaNNNNNNNNNNNTCCGCCAGCCGGTCGGNNNNNNNNNNGACAGAATATGTGTAGAGGC-5'

(Top strand =SEQ ID NO:3)
(Bottom strand =SEQ ID NO:4)

5'-tattgacgatCCAttggctgcctgcctNNNNNNNNNNtgcaccgtctgcct...NNNNNNNNNNGACAGAATATGTGTAGAGGC-5'

(Top strand =SEQ ID NO:5)
(Bottom strand =SEQ ID NO:6)

E

Read 1
5'-CTACACGACGCTCTTCCGATCT...NNNNNNNNNN...NNNNNNNNNNTGTCTCTTATACACATCTCCG
Cell BC   Mol ID   BstXI                                    BC2          Read 2
                   switch                BC1
                   oligo seq (Top strand =SEQ ID NO:7)
(Bottom strand =SEQ ID NO:8)

5'-CTACACGACGCTCTTCCGATCT[Cell BC][Mol ID][BstXI]NNNNNNNNNNNNNNNNgtaccgctgcctgttgcccTTTCTTATATAgggNNNNNNNNNNNNNCTGTCTCTTATACACATCTCCG
GATGTGCTGCGAGAAGGCTAGA[ ][ ][ ]NNNNNNNNNNNNNNNNcatggcgacggacaacgggAAAGAATATATcccNNNNNNNNNNNNNGACAGAGAATATGTGTAGAGGC-5'

Read 1    Cell BC   Mol ID   BstXI                    switch         BC1                        BC2                        Read 2
                                                     oligo seq (Top strand = SEQ ID NO:7)
                                               (Bottom strand = SEQ ID NO:8)

Figure 3A-L (continued)

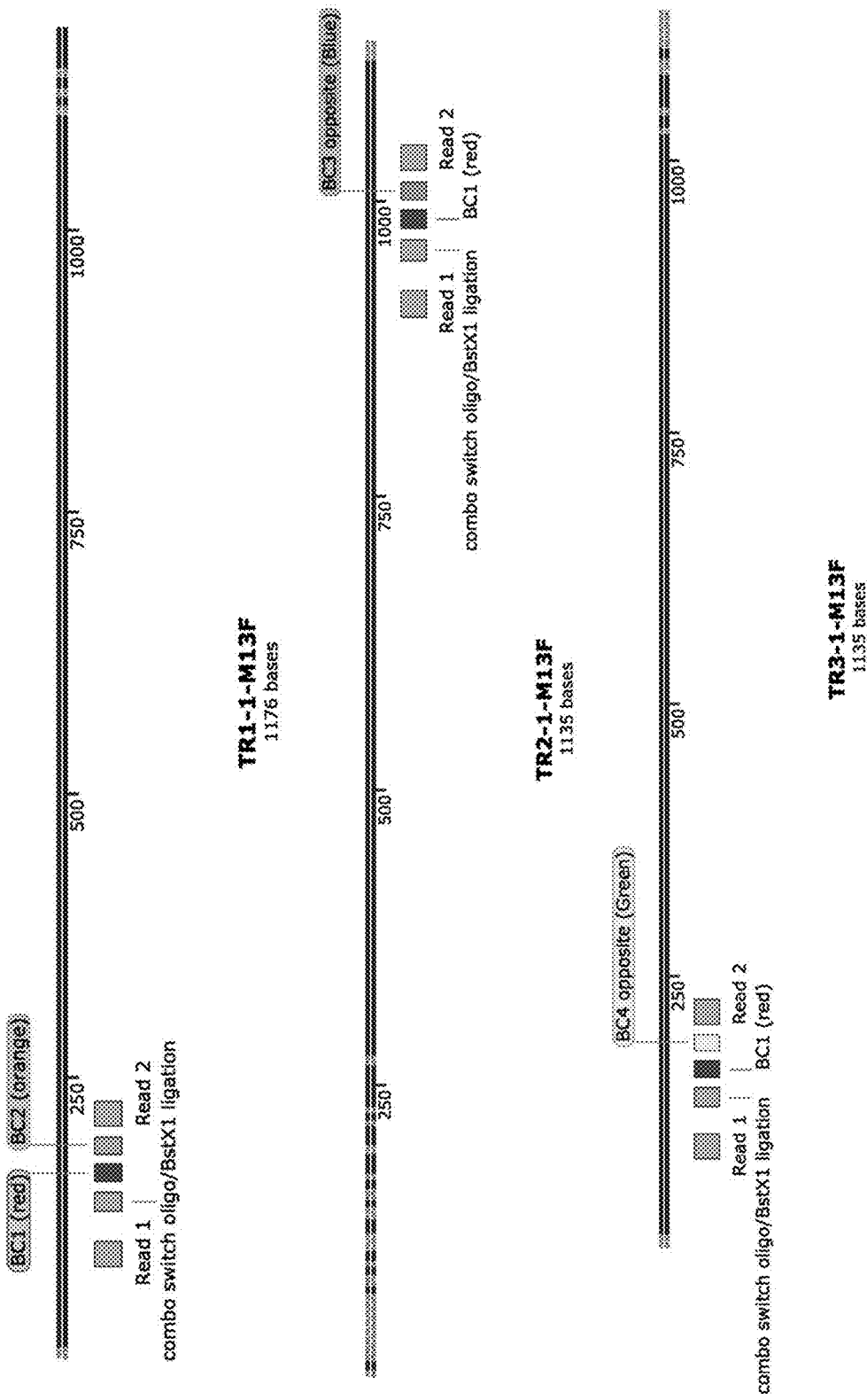
Figure 3A-L (continued)

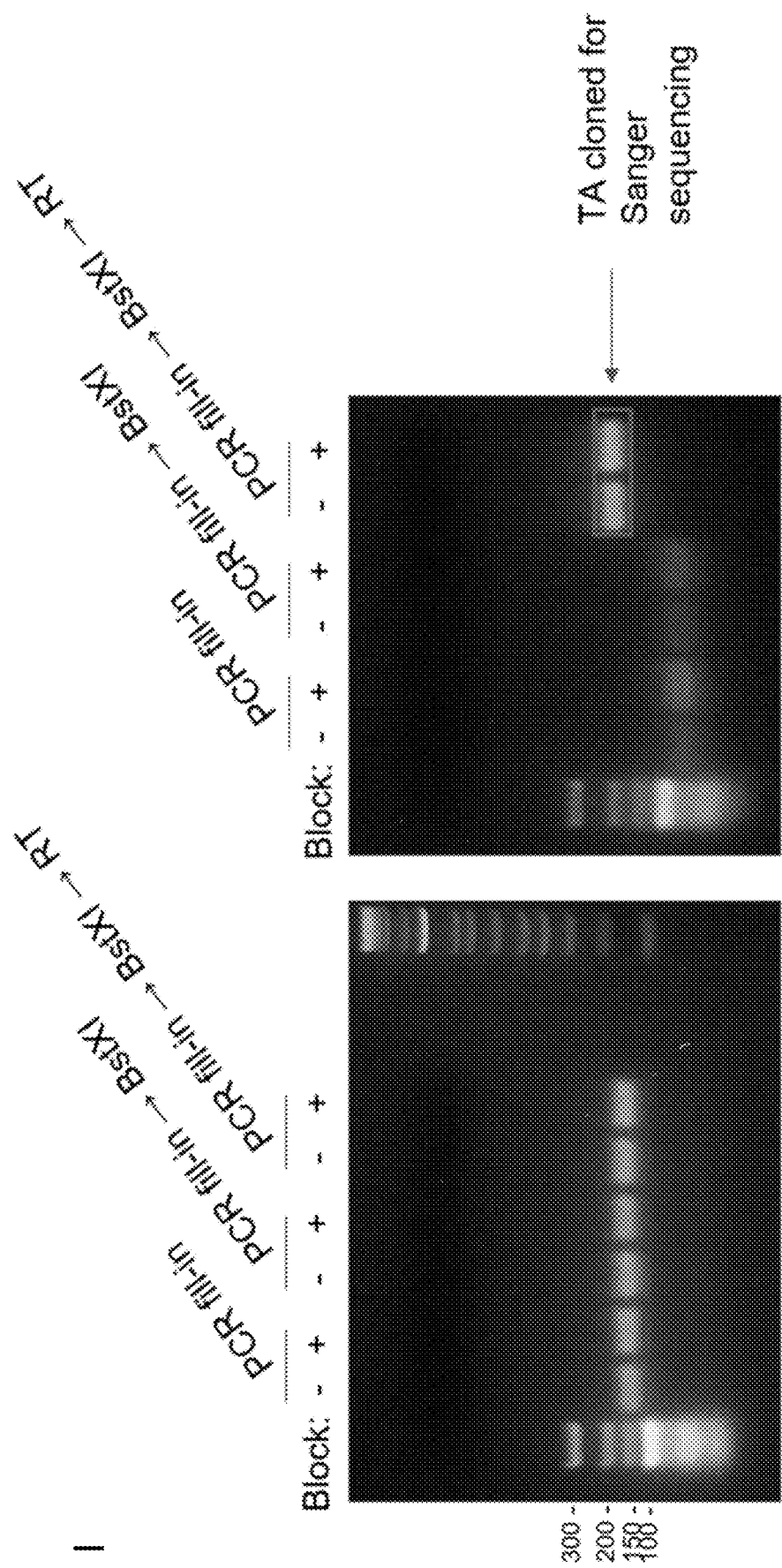
Figure 3A-L (continued)

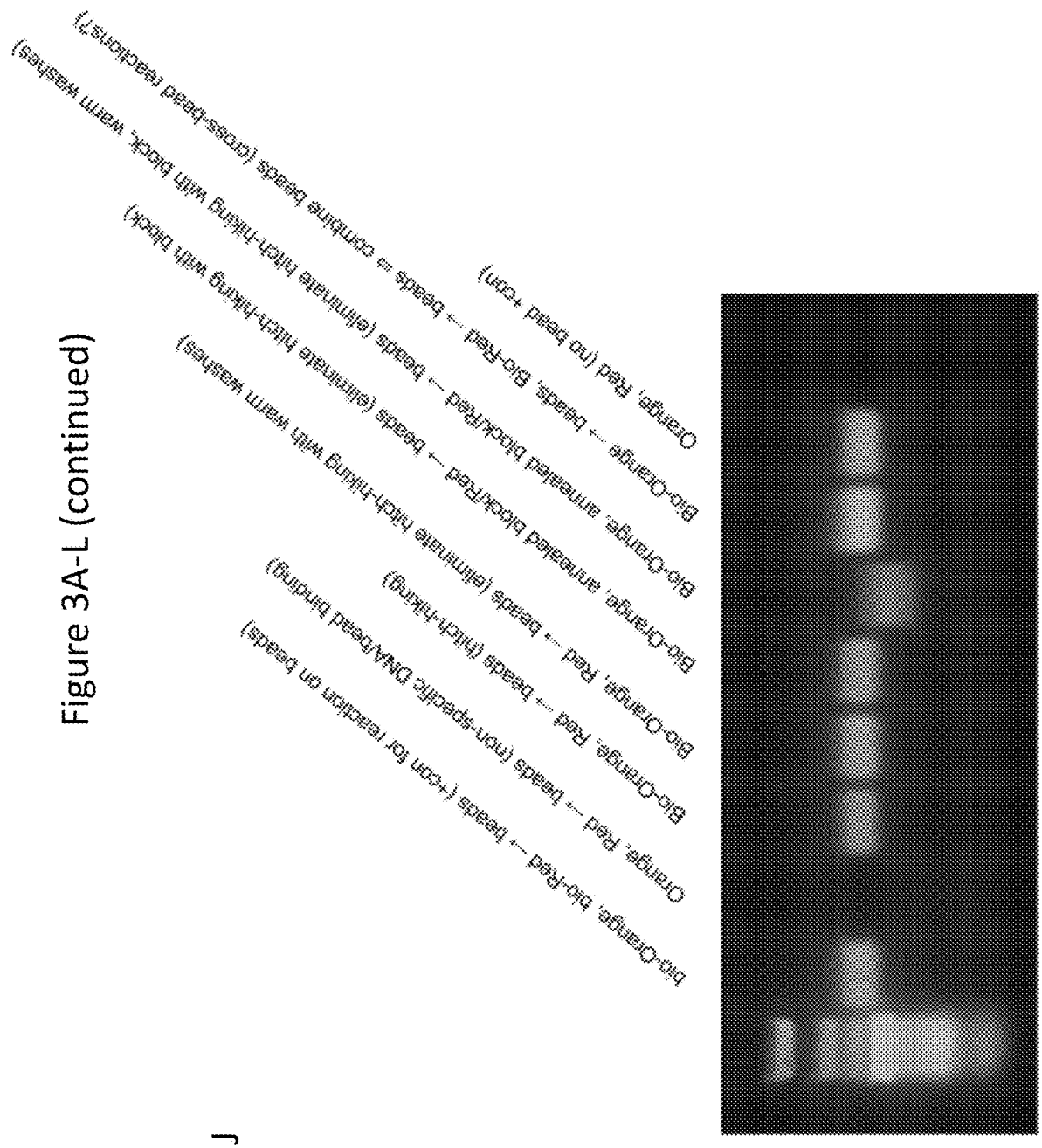
Figure 3A-L (continued)

Figure 3A-L (continued)
K
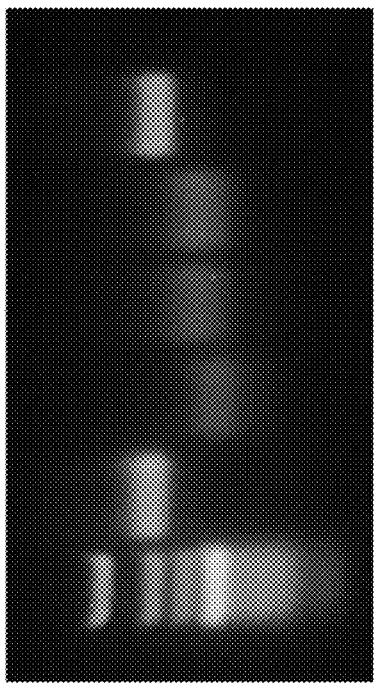
Bio-Orange
Bio-Orange + beads (cross-bead reactions?)
Bio-Orange annealed blocked + beads (eliminate hitch-hiking with block, warm washes)
Bio-Orange annealed blocked + beads (eliminate hitch-hiking with block)
Orange, Red + beads (non-specific DNA/bead binding)
bio-Orange, bio-Red + beads (+con for reaction on beads)

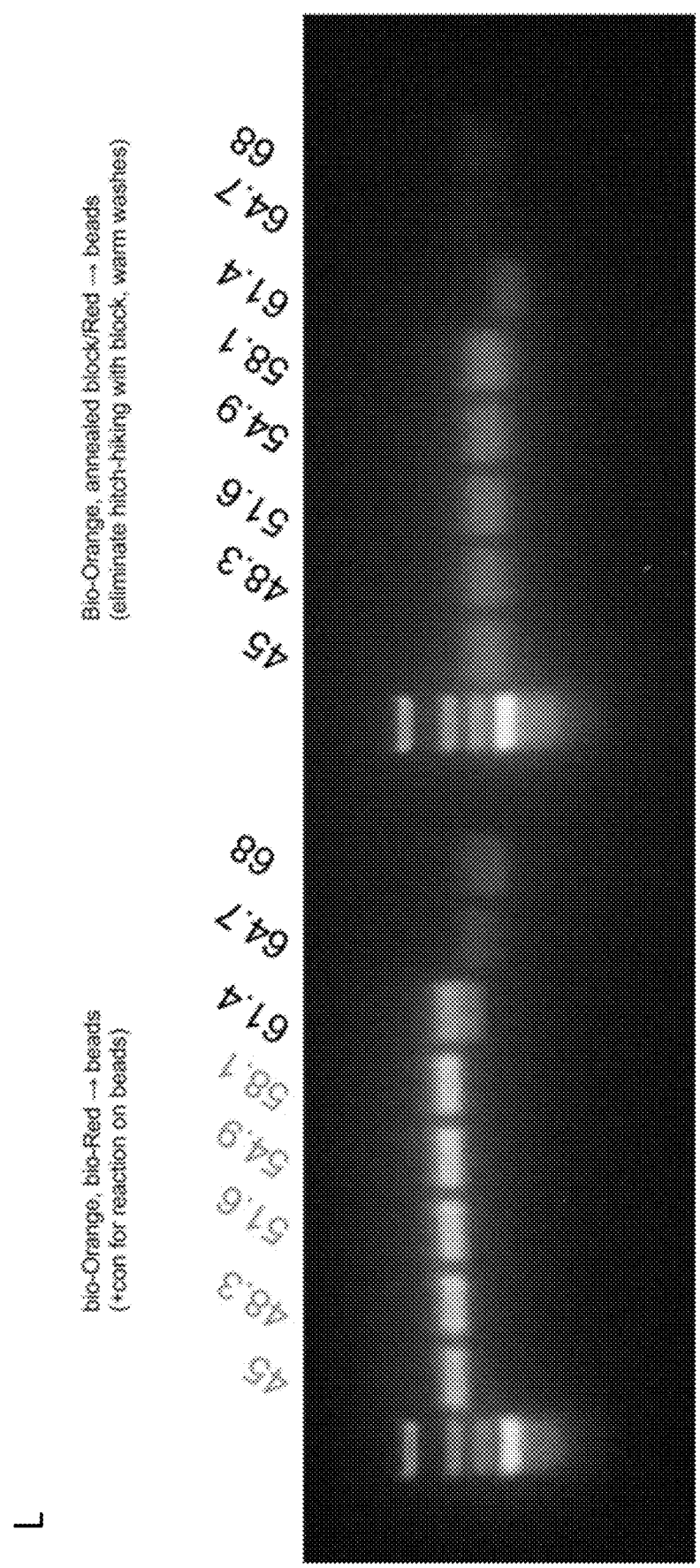
Figure 3A-L (continued)

Figure 5

```
In [12]:
    #so we can open an R1 and R2 file and take chunked records
    #these records are spots on the chip
    #we can regex search ligation features, and retrieve the cellular/uml features = [
      ('CD274', '', {10,10}GTGCTGCCGACAATAC-{9,9}', '', '', ''),            (SEQ ID NO:13)
      ('CD16',  '', {10,10}AAGTTGTACTCTTTGC-{9,9}', '', '', ''),            (SEQ ID NO:14)
      ('CD56',  '', {10,10}TTCGCCCCATTGAGT-{9,9}',  '', '', ''),            (SEQ ID NO:15)
      ('CD4',   '', {10,10}TGTCCCCCCTCAACT-{9,9}',  '', '', ''),            (SEQ ID NO:16)
      ('CD8a',  '', {10,10}GCTCCAGCTTTCCATT-{9,9}', '', '', ''),            (SEQ ID NO:17)
      ('CD19',  '', {10,10}CTGGGCAATTACTCCG-{9,9}', '', '', ''),            (SEQ ID NO:18)
      ('CD20',  '', {10,10}TTCTGGATGCCCTAGA-{9,9}', '', '', ''),            (SEQ ID NO:19)
      ('CD21',  '', {10,10}AACCTAGTAGTTCCG-{9,9}',  '', '', ''),            (SEQ ID NO:20)
      ('CD19_09_CD21', '', {10,10}CGAGTAAATGCCCAG-{9,9}CCGACTACTAGGTT-{9,9}CC',  (SEQ ID NOs:21, 22)
      ('CD19_27_CD21', '', '', {27,27}CCGAACTACTAGGTT-{9,9}', '', ''),      (SEQ ID NOs:23, 24)
      ('CD19_70_CD21', '', {70,70}CCGAACTACTAGGTT-{9,9}', '', '', ''),      (SEQ ID NOs:25, 26)
      ('CD25',  '', {10,10}TTTGCTCTGTACGCC-{9,9}',  '', '', ''),            (SEQ ID NO:27)
      ('CD279', '', {10,10}ACAGCAGGCGTATTTA-{9,9}', '', '', ''),            (SEQ ID NO:28)
      ('CD278', '', {10,10}CAGTAAGTTCGGGAC-{9,9}',  '', '', ''),            (SEQ ID NO:29)
      ('CD137', '', {10,10}GTGTGATGTCCTAAG-{9,9}',  '', '', ''),            (SEQ ID NO:30)
      ('CD127', '', {10,10}TCAACAGCTAATGGTCCAG-{9,9}', '', '', ''),         (SEQ ID NO:31)
      ('CD273', '', {10,10}TCAAGCGTTTCTGGCTAG-{9,9}', '', '', ''),          (SEQ ID NO:32)
      ('CD14',  '', {10,10}CAATCAGACTATGA-{9,9}',   '', '', ''),            (SEQ ID NO:33)
      ('CD117', '', {10,10}AGACTAATAGCTGAC-{9,9}',  '', '', ''),            (SEQ ID NO:34)
      ('CD152', '', {10,10}ATGTTGGTCACGTAATC-{9,9}', '', '', ''),           (SEQ ID NO:35)
      ('CD33',  '', {10,10}CATTTGCTCCCGGT-{9,9}',   '', '', ''),            (SEQ ID NO:36)
      ('CD134', '', {10,10}AACCCACCGGTTGTTA-{9,9}', '', '', ''),            (SEQ ID NO:37)
      ('CD141', '', {10,10}GGATAAACTCCCTT-{9,9}',   '', '', ''),            (SEQ ID NO:38)
      ('CD34',  '', {10,10}GCAAAAAAGTCCCTT-{9,9}',  '', '', ''),            (SEQ ID NO:39)
      ('CD45',  '', {10,10}TGCAATTACCCGGAT-{9,9}',  '', '', ''),            (SEQ ID NO:40)
      ('CD3',   '', {10,10}CTCATTGTAACTCCT-{9,9}',  '', '', ''),            (SEQ ID NO:41)
    ]

features = OrderedDict(features)
```

Figure 7

| In [2] : | len('CGGAGATGTGTATAAGAGACAGNNNNNNNNN CGAGTAATTGCCCAGNNNNNNNNNNNNNNNN NNNNNNNNNNNNNNNNNNNNNNNNNNNNNNNN NNNNNNNNNNNNNNNNCCGAACTACTAGGTTN NNNNNNCCCCATATAAGAAA') (SEQ ID NO:42)<br><br>len('NNNNNNNNNCGAGTAATTGCCCAGNNNNNNNNN NNNNNNNNNNNNNNNNNNNNNNNNNNNNNNNN NNNNNNNNNNNNNNNNNNNNNNNNNNNNNCCG AACTACTAGGTTNNNNNNNNNCCCATATAAGAAA') (SEQ ID NO:43) |
|---|---|
| Out [2] : | 132 |

(SEQ ID NO:54)
(SEQ ID NO:55)

The R2 read contains [10 sp][CGAGTAATTGCCCAG][9][2770 sp][CCGAACTACTAGGTT][9 sp]
[CCCATATAAGAAAA] The first 2 defined DNA sequences are ligation sites (colored red below)
(SEQ ID NO:56)

SYSTEMS AND METHODS FOR DETECTING MULTI-MOLECULE BIOMARKERS

CROSS-REFERENCE TO RELATED APPLICATIONS

This patent application is a divisional of U.S. application Ser. No. 17/566,088, filed Dec. 30, 2021, which claims priority to U.S. Provisional Application 63/133,035, filed Dec. 31, 2020. The entire content of each of the above-referenced applications is incorporated herein by reference.

SEQUENCE LISTING

This application includes a sequence listing in XML format titled "166619.00232_fixed.xml", which is 142,899 bytes in size and was created on Feb. 8, 2023. The sequence listing is electronically submitted with this application via Patent Center and is incorporated herein by reference in its entirety.

BACKGROUND

Detecting biomarkers in a biological or patient specimen can facilitate medical decision-making for patient care or biomedical research. In some instances, a biomarker is a combination of two or more molecules in close proximity (for instance, a multi-molecule biomarker) and detecting the individual molecules without spatial information as to their relative physical positions is not as informative as detecting the combination of the molecules in close proximity.

Current methods for detecting multi-molecule biomarkers include the use of a single antibody that binds to all of the molecules of the multi-molecule biomarker, as well as the use of separate primary antibodies for each molecule in the multi-molecule biomarker in conjunction with a secondary antibody that binds to all of the primary antibodies when they are in close proximity. However, generation of such multi-molecule binding antibodies is challenging, and such methods are typically limited to the detection of a single, multi-molecule complex. Accordingly, there is a need in the art for alternative, high-throughput methods to detect multi-molecule biomarkers.

SUMMARY

Disclosed herein are methods, systems, compositions, and kits for the detection of multi-molecule biomarkers in a biological sample. The methods and kits utilize antibody oligonucleotide tags (AOTs) and, in some embodiments, they use one or more of a splint oligonucleotide, a primer oligonucleotide, and a capture oligonucleotide, to form a proximity detection nucleic acid (PDNA). Detection of the PDNA indicates that the multi-molecule biomarker is present in the sample. In some embodiments, the PDNA is detected via high-throughput sequencing methods.

In a first aspect, the present invention provides methods for detecting a PDNA.

In a first embodiment, the methods comprise: (a) providing a first antibody-oligo tag (AOT) comprising a first antibody and a first oligonucleotide, and a second AOT comprising a second antibody and a second oligonucleotide; wherein the first antibody of the first AOT binds a first target in a biological sample, and the second antibody of the second AOT binds a second target in the biological sample; wherein the first oligonucleotide of the first AOT comprises a first hybridization region, and the second oligonucleotide of the second AOT comprises a second hybridization region, and wherein the first and second hybridization regions are complementary and hybridize to each other under hybridization conditions thereby forming a proximity detection nucleic acid (PDNA); (b) contacting, in a reaction vessel, the biological sample and the first and second AOTs under conditions that allow for binding of the first and second antibodies to their respective targets; (c) providing hybridization conditions to the reaction vessel wherein the complementary regions of the first and second oligonucleotides form the PDNA if the first and second targets are in proximity in the biological sample; and (d) detecting the PDNA.

In a second embodiment, the methods comprise: (a) providing a first antibody-oligo tag (AOT) comprising a first antibody and a first oligonucleotide, and a second AOT comprising a second antibody and a second oligonucleotide; wherein the first antibody of the first AOT binds a first target in a biological sample, and the second antibody of the second AOT binds a second target in the biological sample; and wherein the first oligonucleotide of the first AOT comprises a first hybridization region and the second oligonucleotide of the second AOT comprises a second hybridization region; (b) providing a splint oligonucleotide, wherein the splint oligonucleotide comprises a first complementary splint region (CSR) that is complementary to the first hybridization region of the first AOT and a second CSR that is complementary to the second hybridization region of the second AOT, wherein the first and second hybridization regions hybridize to the first and second CSRs under hybridization conditions thereby forming a proximity detection nucleic acid (PDNA); (c) contacting, in a reaction vessel, the biological sample and the first and second AOTs under conditions that allow for binding of the first and second antibodies to their respective targets; (d) adding the splint oligonucleotide to the reaction vessel; (e) providing hybridization conditions to the reaction vessel wherein the hybridization regions of the first and second oligonucleotides of the first and second AOTs hybridize to the first and second CSRs of the splint oligonucleotide and form the PDNA if the first and second targets are in proximity in the biological sample; and (f) detecting the PDNA.

In a third embodiment, the methods comprise: (a) providing a first antibody-oligo tag (AOT) comprising a first antibody and a first oligonucleotide, and a second AOT comprising a second antibody and a second oligonucleotide; wherein the first antibody of the first AOT binds a first target in a biological sample, and the second antibody of the second AOT binds a second target in the biological sample; wherein the first oligonucleotide of the first AOT comprises a first and a second hybridization region, and the second oligonucleotide of the second AOT comprises a third and a fourth hybridization region; (b) providing a primer oligonucleotide comprising a primer region and a region complementary to the first hybridization region of the first AOT; (c) providing a capture oligonucleotide comprising a capture region and a region complementary to the third hybridization region of the second AOT; (d) providing a splint oligonucleotide comprising (i) a first complementary splint region (CSR), wherein the first CSR is complementary to the second hybridization region of the first AOT, and (ii) a second CSR, wherein the second CSR is complementary to the fourth hybridization region of the second AOT; (e) contacting, in a reaction vessel, the biological sample and the first and second AOTs under conditions that allow for binding the first and second antibodies to their respective targets; (f) adding the primer oligonucleotide, the capture oligonucleotide, and the splint oligonucleotides to the reaction vessel; (g) providing hybridization conditions in the reaction vessel wherein the first and second hybridization regions of the first AOT and the third and fourth hybridization regions of the second AOT hybridize to the primer oligonucleotide, the capture oligonucleotide, and the splint oligonucleotide to form a PDNA if the first and second targets are in proximity in the biological sample; and (h) detecting the PDNA.

In a second aspect, the present invention provides kits comprising two or more antibody-oligo tags (AOTs) and optionally comprising one or more of: a splint oligonucleotide, a primer oligonucleotide, and a capture oligonucleotide.

BRIEF DESCRIPTION OF THE DRAWINGS

FIG. 1 is a flow chart summarizing one exemplary method for detecting multi-molecule biomarkers using sequencing of proximity detection nucleic acid (PDNA) molecules.

FIG. 3A-L shows schematic depictions and experimental results related to Example 2. (A-G) Schematic depiction of the method described in Example 2A. (H) Schematic depiction of the validation experiments described in Example 2B. (I-L) Results of the validation experiments described in Example 2B. Each of these gels includes the same standard ladder in the leftmost lane, though some of the ladders are unlabeled. (I) Image of an agarose gel showing the double-stranded DNA product (approximately 155 bp long) generated by the PCR fill-in reaction. (J) Image of an agarose gel showing the DNA products generated from reactions that included various combinations of biotinylated (denoted by a "bio-" prefix) and unbiotinylated (denoted by the lack of a "bio-" prefix) versions of the red and orange antibody-oligo tag (AOT). The contents of each lane, from left to right, are as follows: 1. standard ladder, 2. biotinylated-orange AOT mixed with biotinylated-red AOT and added to magnetic beads (positive control for the reaction occurring as expected), 3. unbiotinylated-orange AOT mixed with unbiotinylated-red AOT and added to magnetic beads (to test for non-specific bead binding), 4. biotinylated-orange AOT mixed with unbiotinylated-red AOT, added to magnetic beads, and washed with cold solution (control for hitchhiking by the unbiotinylated-red AOT), 5. biotinylated-orange AOT mixed with unbiotinylated-red AOT, added to magnetic beads, and washed with warm (37° C.) solution (to test whether it is possible to suppress the hitchhiking of the unbiotinylated-red AOT using a warm wash and no blocker), 6. biotinylated-orange AOT mixed with unbiotinylated-red AOT annealed to blocker oligo, added to beads, and washed with cold solution (to test whether it is possible to suppress hitchhiking using a blocker oligo and cold washes), 7. biotinylated-orange AOT mixed with unbiotinylated-red AOT annealed to blocker oligo, added to beads, and washed with warm (37° C.) solution (to test whether it is possible to suppress hitchhiking using both blocking and warm washes), 8. biotinylated-orange AOT was added to magnetic beads and biotinylated-red AOT was separately added to magnetic beads, then the beads bound to the biotinylated-orange AOT were mixed with beads bound to the biotinylated-red AOT and were washed with warm (37° C.) solution (to test whether a cross bead reaction is possible), 9. unbiotinylated-orange AOT and unbiotinylated-red AOT were combined without magnetic beads with 1:500 reduction of the PCR fill-in (to determine whether the PCR reaction was occurring properly). (K) Image of an agarose gel showing the DNA products generated from reactions that included various combinations of biotinylated (denoted by a "bio-" prefix) and unbiotinylated (denoted by the lack of a "bio-" prefix) versions of the red and orange AOTs. The contents of each lane, from left to right, are as follows: 1. standard ladder, 2. biotinylated-orange AOT mixed with biotinylated-red AOT and added to magnetic beads (positive control for the reaction occurring as expected), 3. unbiotinylated-orange AOT mixed with unbiotinylated-red AOT and added to magnetic beads (to test for non-specific bead binding), 4. biotinylated-orange AOT mixed with unbiotinylated-red AOT annealed to blocker oligo, added to beads, and washed with cold solution (to test whether it is possible to suppress hitchhiking using a blocker oligo and cold washes), 5. biotinylated-orange AOT mixed with unbiotinylated-red AOT annealed to blocker oligo, added to beads, and washed with warm (37° C.) solution (to test whether it is possible to suppress hitchhiking using a blocker oligo and warm washes), 6. biotinylated-orange AOT was added to magnetic beads and biotinylated-red AOT was separately added to magnetic beads, then the beads bound to the biotinylated-orange AOT were mixed with the beads bound to biotinylated-red AOT and were washed with warm (37° C.) solution (to test whether a cross bead reaction is possible). (L) Image of an agarose gel showing the DNA products generated at various annealing temperatures. The lanes on the left half of the gel contain biotinylated-orange AOT mixed with biotinylated-red AOT and added to magnetic beads (positive control), and the lanes on the right half of the gel contain biotinylated-orange AOT mixed with unbiotinylated-red AOT annealed to blocker oligo, added to beads, and washed with warm (37° C.) solution (negative control). The annealing temperature for each reaction, which ranged from 45-68° C., is indicated above the lane.

FIG. 5 is an exemplary list of feature sequences, which are described in Example 4.

FIG. 7 shows two exemplary search strings, which are described in Example 6.

FIG. 8A-B shows an example of genetic sequencing information detected in a biological specimen. This figure is described in Example 6. (A) Exemplary combined paired-end reads (Read 1 and Read 2 sequences originating from 10×R1 and R2 primer sites, respectively). Each row represents a combined R1R2 sequence read. The first 10 bp represent Spacer 1, the next 15 bp highlighted in gray represent the Feature Barcode (which is associated with a CD19 antibody in this example), the next 9 bp represent Spacer 2, the next 13 bp represent the Capture Sequence, the next 26 bp represent the UMI&10× Barcode, the next 22 bp represent the Read_1 primer site. In this example, the Feature Barcode is a portion of an oligo that is conjugated to an antibody. (B) Exemplary R2 reads. Sites where ligation may occur (including Feature Sequences) are colored red. Each row represents an R2 read. The first 10 base pairs are Spacer 1, the next 15 base pairs are a Feature Sequence (colored red) associated with a CD19 antibody, followed by a 9, 27, or 70 bp spacer, then a Feature Sequence (colored red) associated with a CD21 antibody, then a 9 bp spacer, followed by the Capture Sequence.

DETAILED DESCRIPTION

Figure 2:
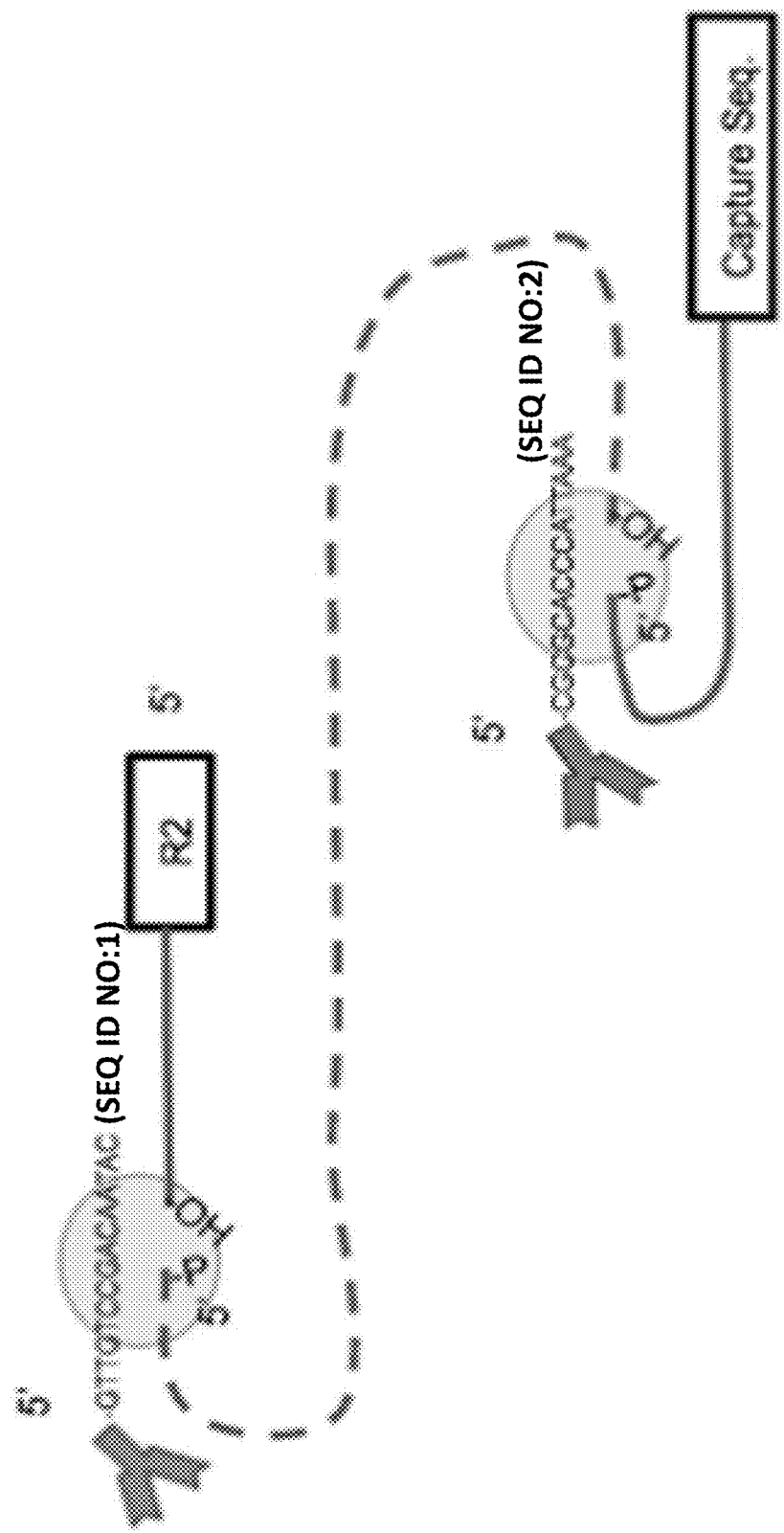
FIG. 2 is a schematic depicting the method described in Example 1.

Disclosed herein are methods and kits for the detection of multi-molecule biomarkers in a biological sample.

Definitions

To aid in understanding the present disclosure, several terms are defined below.

Unless defined otherwise, all technical and scientific terms used herein have the same meaning as commonly understood by one of skill in the art. Although any methods and materials similar to or equivalent to those described herein can be used in the practice or testing of the claims, the exemplary methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

The term "about" means within a statistically meaningful range of a value or values such as a stated concentration, length, molecular weight, pH, time frame, temperature, pressure or volume. Such a value or range can be within an order of magnitude, typically within 20%, more typically within 10%, and even more typically within 5% of a given value or range. The allowable variation encompassed by "about" will depend upon the particular system under study.

The terms "comprising," "having," "including," and "containing" are to be construed as open-ended terms (meaning "including, but not limited to,") unless otherwise noted.

Recitation of ranges of values herein are merely intended to serve as a shorthand method of referring individually to each separate value falling within the range, and includes the endpoint boundaries defining the range, unless otherwise indicated herein, and each separate value is incorporated into the specification as if it were individually recited herein.

The terms "nucleic acid," "oligonucleotide," and "polynucleotide," as used herein, refer to polydeoxyribonucleotides (containing 2-deoxy-D-ribose), polyribonucleotides (containing D-ribose), and to any other type of nucleotide sequence that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present methods and kits, an oligonucleotide also can comprise nucleotide analogs in which the base, sugar, or phosphate backbone is modified as well as non-purine or non-pyrimidine nucleotide analogs. Oligonucleotides can be of genomic, natural, or synthetic origin.

Synthetic polynucleotides can be prepared by any suitable method, including direct chemical synthesis, for example, using a method such as the phosphotriester method of Narang et al. (1979, Meth. Enzymol. 68:90-99), the phosphodiester method of Brown et al. (1979, Meth. Enzymol. 68:109-151), the diethylphosphoramidite method of Beaucage et al. (1981, Tetrahedron Letters 22:1859-1862), or the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, which is incorporated herein by reference.

Polynucleotides may optionally include one or more non-standard nucleotide(s), nucleotide analog(s) and/or modified nucleotides. Examples of modified nucleotides include, but are not limited to, diaminopurine, S2T, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (for example, at one or more atoms that typically are available to form a hydrogen bond with a complementary nucleotide and/or at one or more atoms that are not typically capable of forming a hydrogen bond with a complementary nucleotide), sugar moiety, or phosphate backbone.

The term "hybridizing" and "annealing" are used interchangeably herein and refer to a process by which a strand of nucleic acid binds to another strand of nucleic acid through complementary base pairing, thereby forming a duplex structure. Hybridization can occur between fully complementary nucleic acid strands or between "substantially complementary" nucleic acid strands that contain minor regions of mismatch. As used herein, the term "hybridization conditions" refers to any reaction conditions in which complementary single-stranded nucleic acids have the ability to undergo hybridization. Conditions under which hybridization of fully complementary nucleic acid strands are strongly preferred and are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those of skill in the art understand that several factors, including temperature, salt concentration, the length of the complementary sequences, the GC content of the complementary sequences, and the complexity of the complementary sequences, affect hybridization stringency. For example, increasing the temperature or decreasing the amount of salt in a reaction increases stringency and reduces hybridization of sequences that are not 100% identical. Guidance regarding hybridization conditions is readily available in the art (see, for example, Sambrook et al., 1989, Molecular Cloning—A Laboratory Manual, Cold Spring Harbor Laboratory, Cold Spring Harbor, New York; Wetmur, 1991, Critical Review in Biochem. and Mol. Biol. 26(3/4): 227-259; and Owczarzy et al., 2008, Biochemistry, 47: 5336-5353, which are incorporated herein by reference).

As used herein, the term "complementary" refers to the ability of a nucleic acid molecule to bind to (hybridize with) another nucleic acid molecule through the formation of hydrogen bonds between specific nucleotides (namely, A with T or U and G with C), forming a double-stranded molecule.

The term "amplification reaction" refers to any chemical reaction, including an enzymatic reaction, which results in replication of a nucleic acid target sequence or results in transcription of a nucleic acid target sequence. The product of an amplification reaction is a nucleic acid of a defined length. Amplification reactions include reverse transcription, polymerase chain reaction (PCR), including real-time PCR (see U.S. Pat. Nos. 4,683,195 and 4,683,202; PCR Protocols: A Guide to Methods and Applications (Innis et al., eds, 1990)), and ligase chain reaction (LCR) (see Barany et al., U.S. Pat. No. 5,494,810). Typically, amplification protocols comprise either two- or three-step cycles. Two-step cycles comprise a high-temperature denaturation step followed by a hybridization/elongation (or ligation) step. Three-step cycles comprise a denaturation step followed by a hybridization step followed by a separate elongation step.

The term "polymerization reaction" refers to a chemical reaction in which two or more molecules (monomers) combine to form larger molecules that contain repeating structural units (polymers). By way of example but not by way of limitation, in some embodiments, the polymerization reactions described herein involve the formation of DNA. Nucleotides are joined together in a condensation reaction that is catalyzed by a DNA polymerase.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase, and *Thermus aquaticus* (Taq) DNA polymerase, among others. The foregoing examples of DNA polymerases are also known as "DNA-dependent DNA polymerases". "RNA polymerases" catalyze the polymerization of ribonucleotides. Reverse transcriptase, which generates complementary DNA from an RNA template, is an example of an RNA-dependent DNA polymerase. Known examples of DNA-dependent RNA polymerase include, for example, T3 RNA polymerase, T7 RNA polymerase, SP6 RNA polymerase, and *E. coli* RNA polymerase, among others. The polymerase activity of any of the above enzymes can be determined by means well known in the art.

The terms "target sequence", "target region", and "target nucleic acid" are synonymous and are used herein to refer to a region or sequence of a nucleic acid which is to be amplified, sequenced, or detected.

"Target", as used herein with reference to antibody binding, refers to a molecule, such as a protein, or a part or region of a molecule such as a protein (for example, an epitope), that is bound by an antibody. In some embodiments, a single molecule (for example, a single protein) may include multiple targets. In some embodiments, a single molecule (for example, a single protein) comprises a single target. In some embodiments, the target is a protein, a sugar, or a phosphate. In some embodiments, a target comprises a biomarker, for example, a multi-molecule biomarker.

The term "primer" or "primer oligonucleotide", as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides, and from 25 to 150 nucleotides. Short primer molecules generally require cooler temperatures to form sufficiently stable hybrid complexes with the template. A primer need not reflect the exact sequence of the template nucleic acid but must be sufficiently complementary to hybridize with the template. The design of suitable primers for the amplification of a given target sequence is a standard practice in the art and described in the literature cited herein.

Primers comprise a "primer region" that performs the basic function of the primer, namely, acting as a point of initiation of DNA synthesis. Primers may incorporate additional elements so long as they do not interfere with this basic function, including elements that allow for the detection, immobilization, or localization of the primer. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A) sequence). The region of the primer that is sufficiently complementary to the template to hybridize is referred to herein as a "hybridizing region".

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

The term "reaction mixture", as used herein, refers to a solution containing reagents necessary to carry out a given reaction. A reaction mixture is referred to as "complete" if it contains all reagents necessary to enable the reaction and is referred to as "incomplete" if it contains only a subset of the necessary reagents. An "amplification reaction mixture", which refers to a solution containing reagents necessary to carry out an amplification reaction, typically contains oligonucleotide primers and a DNA polymerase in a suitable buffer. For example, a "PCR reaction mixture," refers to a solution containing all the reagents necessary to carry out a PCR reaction, and typically contains DNA polymerase, dNTPs, and a divalent metal cation in a suitable buffer.

The methods described herein are performed in a reaction vessel. The term "reaction vessel", as used herein, refers to any container suitable for holding the components of the reactions described herein. Examples of vessels include, but are not limited to, a PCR tube, a test tube, a microfuge tube, a beaker, a flask, a multi-well plate, a microtiter plate, a cuvette, a flow system, a microfiber, a microscope slide, and the like.

As used herein, the term "biomarker" or "marker" refers to a biological molecule that is associated with a particular disease or condition, and/or is indicative of a particular cell type, cell state, tissue type, or tissue state. Suitable biomarkers include, for example, nucleic acids, proteins, lipids, sugar moieties, hormones, and the like. Biomarkers can be used as part of a predictive, prognostic, or diagnostic process. For example, biomarkers may be used to predict the likelihood that a particular subject will respond to a particular therapeutic. In some cases, the mere presence (or absence) of a biomarker in a biological sample is indicative of a particular condition, whereas in other cases the biomarker is only indicative of a condition when it is present at a particular level or in a specific location within a biological sample. For example, in some cases a biomarker is a differentially expressed gene. In some embodiments, the biomarker is a therapeutic target. In some embodiments, the biomarker is a cancer biomarker, that is, a biomarker that is associated with cancer.

The biomarkers identified by the methods disclosed herein are "multi-molecule biomarkers", meaning they comprise a combination of two or more target molecules. In some embodiments, each target molecule is distinct (for example, two different proteins). In other embodiments, two or more of the target molecules are the same molecule (for example, two copies of the same protein, or two different targets on the same molecule). The systems and methods disclosed herein are designed to detect two or more molecules that are located in close proximity to each other within a biological sample. For example, the biomarkers that may be targeted by the present methods and kits may be detected on the surface of a cell or within a cell present in the biological sample. In some embodiments, the methods are used to detect biomarkers on the surface of the cell. Exemplary, non-limiting multi-molecule markers include heterodimeric partners (for example, receptors), proteins that interact to form functional proteins complexes, proteins that are altered (for example, by phosphorylation, glycosylation, etc.) in a manner that affects their active state or function.

As used herein, an "antibody-oligo tag (AOT)" is an oligonucleotide conjugated to an antibody that specifically binds to a target molecule. In one embodiment, portions of the AOT oligonucleotides are designed to anneal to one another if the target molecules they bind to are in proximity (see Example 2A). In this embodiment, the oligonucleotide portion of a first AOT contains a hybridization region that is complementary to a hybridization region on a second AOT (see FIG. 3). In another embodiment, the AOTs are each designed to anneal to a splint oligonucleotide that bridges the AOTs together if the target molecules that the AOTs bind to are in proximity (see Example 1). In this embodiment, the oligonucleotide portions of the AOTs contain a hybridization region that is complementary to a hybridization region on a splint oligonucleotide (see FIG. 2).

The AOTs may comprise any type of antibody. Suitable antibodies include, without limitation, whole antibodies, antibody fragments and combinations of fragments (for example, Fab, scFv, diabodies, scFv-Fc, scFv-CH, scFAb, and sFv-zippers, etc.). Antibodies may be monoclonal, polyclonal, IgG, IgM, IgA, IgD, or IgE.

The length of the oligonucleotide of an AOT may be between about 5 and 500 nucleotides, between about 5 and 400 nucleotides, between about 5 and 300 nucleotides, between about 5 and 200 nucleotides, between about 5 and 100 nucleotides, between about 10 and 50 nucleotides, between about 10 and 40 nucleotides, or between about 10 and 20 nucleotides. In some embodiments, an AOT oligonucleotide is about 5, about 10, about 20, about 30, about 40, about 50, about 60, about 70, about 80, about 90, or about 100 nucleotides. In some embodiments, an AOT oligonucleotide is about 20 nucleotides in length.

As used herein, a "splint oligonucleotide" is an oligonucleotide that comprises hybridization regions, termed "complementary splint regions (CSRs)", that are complementary to the hybridization regions of two or more AOTs. Splint oligonucleotides are not conjugated to antibodies themselves. Instead, they serve to bridge together two or more AOTs via complementary base pairing (see FIG. 2, in which the splint oligonucleotide is depicted as a dashed line). In some embodiments, the splint oligonucleotide is a single-stranded DNA molecule. In some embodiments, the splint oligonucleotide comprises two or more separate splint oligonucleotides.

The length of a splint oligonucleotide may be between about 5 and 100 nucleotides, between about 5 and 50 nucleotides, between about 5 and 30 nucleotides, between about 5 and 25 nucleotides, between about 10 and 100 nucleotides, between about 10 and 50 nucleotides, or between about 15 and 30 nucleotides. In some embodiments, an AOT oligonucleotide is about 5, about 10, about 20, about 30, about 40, about 50, about 60, about 70, about 80, about 90, or about 100 nucleotides. In some embodiments, a splint oligonucleotide is about 20-25 nucleotides in length.

As used herein, the term "mask oligonucleotide" refers to a single stranded oligonucleotide that is complementary to a region of a second oligonucleotide and is capable of hybridizing to the second oligonucleotide. In some embodiments, a mask oligonucleotide is used as a "blocker" that prevents the second oligonucleotide from hybridizing to other oligonucleotides until the mask oligonucleotide is removed.

As used herein, the term "capture oligonucleotide" refers to a sequence that aids in the detection of an oligonucleotide. The portion of the capture oligonucleotide that is necessary for this primary function is referred to as a "capture region". In some embodiments, the capture sequence is a sequence that anneals to a primer for amplification via polymerase chain reaction. In other embodiments, the capture oligonucleotide is an adapter sequence that is designed to interact with a specific sequencing platform (for example, the surface of a flow-cell for Illumina sequencing or beads for Ion Torrent sequencing) to facilitate a sequencing reaction. The optimal length of an adapter sequence will vary depending on the sequencing platform used. One of ordinary skill will understand that adapter sequences may be as short as 20 nucleotides or substantially longer. For example, an adapter sequence of 58 nucleotides may be used with an Illumina machine.

The oligonucleotides (namely, the oligonucleotide component of the AOTs and the splint oligonucleotides) used with the present methods and kits comprise hybridization regions. As used herein, the term "hybridization region" refers to a portion of an oligonucleotide that is complementary to a portion of another oligonucleotide, such that the oligonucleotides hybridize under suitable hybridization conditions. The hybridization regions may be about 6 to about 100 nucleotides in length, about 15 to about 35 nucleotides in length, or about 5-10 nucleotides in length.

As used herein, a "proximity detection nucleic acid (PDNA)" comprises a nucleic acid molecule that is formed when two different AOTs, bound to their respective targets, are spatially distanced such that oligonucleotide hybridization events link the two AOTs. Thus, depending on the design of the AOT oligonucleotide linking reaction, a PDNA can comprise sequences of the AOT oligonucleotides, sequences of one or more splint oligonucleotides, sequences of auxiliary oligonucleotides such as primer oligonucleotide sequences, capture oligonucleotide sequences, and any other functional oligonucleotide sequences provided as a part of one of these sequences (for example, barcode sequences, spacer sequences, primer binding sites, restriction endonuclease sites, etc.). A PDNA may be single-stranded, double-stranded, or comprise regions of both single- and double-stranded nucleic acid. In some embodiments, a single-stranded PDNA or regions of a PDNA that are single-stranded may be converted to double-stranded (for example, DNA, DNA/RNA, or RNA duplex). Thus, in some embodiments, formation of a PDNA may include one or more ligation steps (see, for example, FIG. 2), and/or one or more polymerase fill-in steps (see, for example, FIG. 3C-D). By way of example, a single-stranded portion of a PDNA molecule can be made double-stranded by using a polymerase (for example, DNA polymerase Klenow Fragment, Bsu DNA Polymerase) to fill in single-stranded overhangs, forming a double-stranded nucleic acid molecule. A PDNA may also include one or more restriction endonuclease sites. Such restriction sites may be useful in methods to detect a PDNA.

As used herein, the terms "in proximity" and "in close proximity" are used to indicate that two or more molecules are near each other spatially. The threshold used to determine whether two molecules are in proximity is based on the length of the AOTs and splint oligonucleotides that are used to detect them. For example, if the various oligonucleotides that must hybridize to form a PDNA are long enough to hybridize when the antibody portion of the first AOT is bound to a first target molecule and the antibody portion of the second AOT is bound to a second target molecule, then the first and second target molecules are deemed to be in proximity. Thus, the threshold for determining proximity may be adjusted by altering the lengths of the various oligonucleotides that form the PDNA. A suitable length to use as a threshold will depend on the particular multi-molecular biomarker being assayed.

As used herein, the term "sequencing" has its customary meaning in the art and refers to a method for determining the order of nucleotides in a nucleic acid (in other words, the sequence of the nucleic acid).

A "barcode sequence" or "barcode" (also referred to as index) is a known, unique DNA sequence that is added to a DNA molecule prior to sequencing to allow the resulting sequencing reads to be associated with the input DNA molecule from which they were produced. A barcode sequence may include 4, 5, 6, 7, 8, 9, 10, 11, 12, 13, 14, 15, 16, or more nucleotides. A barcode sequence may be included at the 5'-end, the 3'-end, or in the middle of a DNA molecule.

As used herein, the term "detectable label" refers to a chemical moiety that is attached to an oligonucleotide to render the oligonucleotide detectable. Suitable detectable labels include, without limitation, fluorescent labels, chemiluminescent labels, quenchers, radioactive labels, linker molecules (such as biotin, avidin, streptavidin, HRP, protein A, protein G, antibodies, Grb2, polyhistidine, Ni2+, FLAG tags, myc tags), heavy metals, enzymes (such as alkaline phosphatase, peroxidase, and luciferase), electron donors/acceptors, acridinium esters, dyes, and calorimetric substrates.

As used herein, the term "ligation" or "ligation reaction" has its customary meaning in the art and refers to the joining of two nucleic acids through the action of an enzyme (ligase) which links the two nucleic acids by forming covalent bonds.

As used herein, a "biological sample" refers to a sample taken from a subject. Suitable biological samples include, but are not limited to, a tissue sample (for example, fat, muscle, skin, neurological, tumor, etc.), fluid sample (for example, saliva, blood, serum, plasma, urine, stool, cerebrospinal fluid, etc.), and cells or sub-cellular structures. In some embodiments, a biological sample comprises a tumor sample, such as a biopsy. A biological sample may be fresh, frozen, or formalin fixed paraffin embedded (FFPE).

As used herein, the terms "subject" and "patient" are used interchangeably to mammals and non-mammals to which the methods and kits may be applied. A "mammal" may be any member of the class Mammalia including, but not limited to, humans, non-human primates (for example, chimpanzees, other apes, and monkey species), farm animals (for example, cattle, horses, sheep, goats, and swine), domestic animals (for example, rabbits, dogs, and cats), or laboratory animals including rodents (for example, rats, mice, and guinea pigs). Examples of non-mammals include, but are not limited to, birds, and the like. The term "subject" does not denote a particular age or sex. In one embodiment, the subject is human.

The term "treat" or "treatment" refers to an action or therapy that reduces, alleviates, prevents, or otherwise lessens a disease or condition, the signs or symptoms of a disease or condition, or the duration, severity, or exacerbation of a disease or condition. These terms encompass a full and partial "cure" of a disease or condition.

Methods for Detecting Multi-Molecule Biomarkers

The present disclosure provides methods, compositions, and systems for detecting multi-molecule biomarkers in a biological sample. The methods, compositions, and systems allow for the detection of two or more molecules that are in close proximity, and can be used, for example, to provide information about the activation state of a protein or molecular pathway, or to provide the ability to assay for protein-protein proximity, protein-protein interactions, and protein modifications.

The methods utilize antibodies that each bind to a different target molecule of a multi-molecule biomarker. The antibodies are conjugated to oligonucleotides, forming antibody-oligo tags (AOTs). When the AOTs are applied to a biological sample that contains the multi-molecule biomarker such that the first AOT binds to a first target molecule that is in proximity of a second AOT that binds to a second target molecule, the oligonucleotide portions of the AOTs will hybridize to each other (either directly or via a splint oligonucleotide), thereby forming a duplex structure referred to as a proximity detection nucleic acid (PDNA). The PDNA is then detected using a method such as single-cell sequencing.

One exemplary, non-limiting advantage of the methods disclosed herein is that they can be performed in a high-throughput manner, allowing multiple interactions of interest (for example, multiple combinations of two or more target molecules, each combination representing a different multi-molecule biomarker) to be assayed simultaneously. This can be accomplished, for example, by including unique barcode sequences in the AOT oligonucleotides, to determine which antibodies (and, thus, which target molecules) were in proximity in the biological sample and produced a given PDNA. In some embodiments, the methods are designed to be compatible with single-cell sequencing methods, such as those that use high-throughput, droplet-based systems (for example, 10× Genomics sequencing). In some embodiments, the methods disclosed herein do not utilize both primary antibodies and secondary antibodies; instead, only one set of antibodies is used to detect multi-molecule biomarkers.

FIG. 1 illustrates an exemplary method 100 for detecting multi-molecule biomarkers by sequencing PDNA molecules.

Step 105 in the method of FIG. 1 involves the selection or customization of AOTs.

For each molecule or combination of molecules included in the multi-molecule biomarker, an antibody that binds to the molecule or combination of molecules may be selected. In some cases, an antibody that binds to a target molecule of interest may be commercially available and may even be available as a conjugate with an oligonucleotide (see Example 1). In other cases, the sequence of the oligonucleotide component of an AOT may be customized (see Example 2A). The oligonucleotide component of the AOTs may be a DNA molecule or an RNA molecule, and/or may include natural, non-natural (for example, modified) nucleotides, or a combination thereof.

The sequence of the oligonucleotide components of the AOTs may be selected such that a first and a second AOT can base pair with each other when in close proximity. For example, the oligonucleotide of the first AOT may include a portion that is complementary to a portion of the oligonucleotide of the second AOT. These complementary portions are referred to herein as "hybridization regions". The oligonucleotide components of the AOTs may further include elements that increase the likelihood that a PDNA molecule formed from the AOTs will be amplified during library preparation and sequenced during a sequencing reaction. By way of example, but not by way of limitation, such elements may include a barcode sequence, a primer sequence or primer binding sequence, and/or a capture sequence.

The customization of antibodies and oligonucleotides, and the conjugation of antibodies and oligonucleotides are well known practices in the art. Kits and services for the generation of such customized products are commercially available including, for example, Oligonucleotide-antibody Conjugation Service offered by Creative Biolabs (www.creative-biolabs.com/gene-therapy/oligonucleotide-antibody-conjugation-service.htm); Antibody Conjugation Kit or Oligonucleotide Conjugation Kit from Abcam (www.abcam.com/5rsquo-feature-barcode-antibody-conjugation-kit-lightning-linkreg-oligos-1-10-ab270703.html or www.abcam.com/oligonucleotide-conjugation-kit-ab218260.html); and the FAQ section of the 10× Genomics web site (kb.10xgenomics.com/hc/en-us/articles/360019901551-Can-I-do-custom-oligo-conjugation-for-Feature-Barcoding-assays-).

Step 110 in the method of FIG. 1 is optional and comprises the selection of complementary splint oligonucleotides. This step is performed, for example, if the selected AOTs are not designed to anneal to each other when in close proximity. This would be the case, for example, when there is no portion in the sequence in one AOT oligonucleotide that is complementary to a portion of the sequence in the other AOT oligonucleotide. The splint oligonucleotides may be selected or designed such that they hybridize to, or can be ligated to, the two or more AOTs selected in step 105, to ultimately form a PDNA. The splint oligonucleotides may further include elements that increase the likelihood that a PDNA molecule, or a portion of the PDNA molecule, will be amplified during library preparation, and sequenced during a sequencing reaction.

The nucleotide sequence of each splint oligonucleotide may be selected from pre-established sequences or may be designed. The sequence may be designed or selected to ligate to one or more AOT feature sequences (see FIG. 5 for examples of feature sequences). The splint oligonucleotide may be a DNA molecule or an RNA molecule and/or may include natural, non-natural (for example, modified) nucleotides, or a combination thereof.

In some embodiments, mask oligonucleotides are provided with the AOTs to prevent other oligonucleotides from hybridizing with the AOTs. The use of mask oligonucleotides may reduce false positives by preventing one AOT from hybridizing to another AOT prior to binding a target protein and "hitch-hiking" to its binding site. In such embodiments, the mask oligonucleotides are removed by increasing the temperature (for example, to approximately 37° C.) to melt off the mask after the antibodies have been allowed to bind to their target proteins.

In some embodiments, a primer oligonucleotide and a capture oligonucleotide are provided in addition to the splint oligonucleotide (see, for example, FIG. 2). In these embodiments, the AOT oligonucleotides each have a first region that binds to the end of the splint oligonucleotide and a distinct second region (for example, on the opposite end) that binds to the end of the primer oligonucleotide or capture oligonucleotide. As a result, the AOT oligonucleotides bridge together the splint oligonucleotide, primer oligonucleotide, and capture oligonucleotide such that the primer oligonucleotide is on one end and the capture oligonucleotide on the other. As is shown in FIG. 2, once the splint, primer and capture oligonucleotides hybridize to their respective locations on the AOT oligonucleotides, the splint, primer, and capture oligonucleotides may be ligated, and a polymerase may then be used to form a double-stranded PDNA. In some embodiments, for every possible pair of AOTs that is used in an assay, there may be a distinct set of primer, capture, and splint oligonucleotides.

In another embodiment, the splint oligonucleotide comprises two or more separate splint oligonucleotides that are designed to link to each other via hybridization to form a bridge between two or more AOTs. In this embodiment, the PDNA molecule may include two, three or more AOTs that are bridged together by multiple splint oligonucleotides. For example, in the embodiment shown in FIG. 2, a third AOT may be integrated into the PDNA molecule either (1) between the primer oligonucleotide and the first AOT, (2) between the first and second AOT, or (3) between the second AOT and the capture oligonucleotide. In some embodiments, the length of the splint nucleotide(s) included in the PDNA is used to infer the range of potential distances between two target molecules.

In some embodiments, the splint oligonucleotide may be designed such that it can function as a universal linker that can bridge any two AOT oligonucleotides. In this embodiment, fewer molecules may be needed to interact to produce a PDNA. For example, a universal splint oligonucleotide can be used with multiple antibodies that each have a distinct target molecule to detect any pair or combination of the antibodies and their target molecules that are in close proximity. In this embodiment, it is not necessary to design splint oligonucleotides that are complementary and unique to each possible pair of AOTs. Here, a first set of AOTs (the "bait" AOTs) may all comprise a first oligonucleotide sequence and a second set of AOTs (the "query" AOTs) may all comprise a second oligonucleotide sequence. The AOT oligonucleotides may each comprise a unique barcode sequence to allow one to determine which antibodies (and, thus, which target molecules) were associated and produced a given PDNA.

Once the AOTs and any additional oligonucleotides have been hybridized or ligated together to form a single complex, a polymerase reaction, a polymerase chain reaction, or a reverse transcriptase reaction may be used to convert the hybridized single-stranded regions into double-stranded regions.

Step 115 in the method of FIG. 1 involves combining the AOTs with a biological sample.

As part of step 115, the biological sample and/or the oligonucleotides (for example, splint oligonucleotides, primer oligonucleotides, capture oligonucleotides, etc.) may be subjected to a preparation protocol. In some embodiments, the target molecule is on the outside of the cells, while in other embodiments, the target molecule is inside the cells. For example, the cells within the biological sample may be permeabilized to facilitate the entry of the AOTs into the cell to bind to intracellular target molecules. Methods of cell permeabilization are known in the art, and include, for example, methanol fixation. See, for example, Alles, J., Karaiskos, N., Praktiknjo, S. D. et al. Cell fixation and preservation for droplet-based single-cell transcriptomics. BMC Biol 15, 44 (2017), https://doi.org/10.1186/s12915-017-0383-5, the contents of which are incorporated herein by reference in their entirety. Further, this step may optionally include fixing the AOTs to the target molecules to prevent the antibody and target molecule from separating.

In some embodiments, high performance liquid chromatography (HPLC) purification may be used to purify the oligonucleotides before adding them to a biological specimen. This is facilitated by having a large amount of splint oligonucleotide (for example, 100 nM or more).

Step 116 in the method of FIG. 1 is optional and involves removing excess, unbound AOTs from the biological sample.

In step 120 in the method of FIG. 1, any AOTs in proximity form a PDNA molecule.

In some embodiments, the AOT oligonucleotides link directly to each other via complementary hybridization regions. In some embodiments, splint oligonucleotides are used to link the AOT oligonucleotides, (see, for example, Example 1, FIG. 2, and FIG. 3).

If one or more portions of the linked oligonucleotides are single-stranded (for example, single-stranded DNA), then step 120 may further include converting the single-stranded portions into double-stranded nucleic acid molecules (see Example 2A) to form the PDNA molecule.

Step 120 may further include the addition of ligase to join oligos to form a PDNA molecule (for example, splint oligonucleotides, primer oligonucleotides, and capture sequences), or may include washing away excess (unligated) splint oligos or excess (unbound) AOTs from the biological sample.

Detection of the PDNA may be performed using any suitable method known in the art. For example, amplification methods using one or more of a labeled primer or probe may also be employed. In some embodiments, one or more of the oligonucleotides utilized comprises a detectable label. In some embodiments, the label comprises a fluorescent moiety, biotin, an enzymatic moiety, a radioactive moiety, or another chemical moiety useful for detecting a nucleic acid. In some embodiments, the label is added to an amplification reaction product produced from the PDNA.

Additionally or alternatively, the methods and compositions disclosed herein may rely on the use of high-throughput sequencing. For example, step 125 in the method of FIG. 1 involves the formation or preparation of sequencing libraries from the PDNAs formed in the biological sample. In this step the sample may be processed for next generation sequencing (for example, single-cell (sc)-seq, CITE-seq, bulk sequencing, etc.). In some embodiments, the single-cell sequencing is performed using a high-throughput droplet-based system.

In various embodiments, step 125 may include separating the biological sample into individual cells. Suitable separation methods include, for example, micro-dissection/manipulation, flow cytometry/cell sorting, microfluidic method, and droplet-based methods. In some embodiments, library generation involves automated droplet formation for single-cell sequencing. For example, the 10× Genomics' Chromium™ Single Cell 5' Solution technology may be used to analyze bound AOTs on a cell-by-cell basis using microfluidic partitioning to capture single cells and prepare barcoded, next-generation sequencing (NGS) cDNA libraries. This may be accomplished by designing the AOTs and/or modifying a PDNA to be compatible with the 10× Genomics system, as described in Example 2A. For example, to be compatible with the 10× kit, AOTs are designed to (1) include an R2 sequence and a barcode sequence, (2) be capable of recruiting the switch oligonucleotide, and (3) form an oligonucleotide that is roughly equal in size to the 10× antibody oligos (~150 bp) following switch polymerization. By way of example, a PDNA may be partially single stranded upon formation (after annealing). A DNA polymerase and dNTPs may be added to the reaction to fill in the single-stranded portions, resulting in a fully double-stranded PDNA. In some embodiments, a restriction endonuclease recognition site may be incorporated into a PDNA (for example, as part of the first AOT oligonucleotide) such that cleavage of the PDNA generates a specific single-stranded overhang, mimicking the 10× reverse transcription reaction that occurs in droplets (see the BstXI cleavage site in FIG. 3).

To prepare the sequencing libraries, nucleic acids are isolated from the biological sample. Methods to isolate nucleic acids are well known in the art, and reagents and kits are commercially available. In some embodiments, nucleic acid isolation may include eliminating DNA molecules from all or a portion of the isolated nucleic acid molecules to isolate only RNA molecules, and/or eliminating RNA molecules from all or a portion of the isolated nucleic acid molecules to isolate only DNA molecules.

Library preparation may include enriching for nucleic acid molecules of interest. For example, enrichment may be performed using hybridization capture (for RNA or DNA) of specific sequences (for example, capture sequences). Captured RNA may be reverse transcribed to generate cDNA for sequencing. In some embodiments, hybridization capture is used to enrich for sequences that comprise a capture sequence.

Library preparation may include adding a distinct nucleotide barcode to each isolated nucleic acid molecule. In one embodiment, the barcode is added using a GEMRT incubation wherein each isolated nucleic acid molecule is extended with a 10× barcode and a read 1 sequence (primer site for sequencing read 1). In embodiments in which the biological sample is divided into individual cells, a unique 10× barcode sequence may be used in each cell to distinguish one cell's sequence reads from another cell's sequence reads. In some embodiments, the sequence reads from each cell include all or a portion of the cell's transcriptome, which may be used to determine the cell type or phenotype of the cell.

Library preparation may include amplifying isolated nucleic acid molecules. Amplification may be performed using methods known in the art, for example, using Illumina bridge amplification PCR with P5 and P7 primers, in vitro transcription, or another amplification method.

In some embodiments, a P5 primer, read 2 (primer site for sequencing read 2), sample index, and P7 primer are added to each isolated nucleic acid molecule during library construction. The sample index sequence may be unique to one biological sample (for instance, to distinguish one biological sample's sequence reads from another biological sample's sequence reads, allowing two or more biological samples to be sequenced using a single flow cell). In one embodiment, the sequencing library is a Single Cell 3' Library that comprises a paired-end construct which begins with P5 and ends with P7. 16 bp 10× barcodes may be encoded near the start of read 1, while sample index sequences may be incorporated as the i7 index read.

The sequencing libraries may be prepared according to a 10× Genomics User Guide (support.10xgenomics.com/single-cell-vdj/sample-prep/doc/demonstrated-protocol-single-cell-protocols-cell-preparation-guide, www.10xgenomics.com/resources/user-guides/), the contents of which are incorporated herein by reference in their entirety. In some embodiments, the libraries are Single Cell 3' Libraries.

In step 130 in the method of FIG. 1, the sequencing library generated from the biological sample is sequenced to generate sequencing data.

Any suitable sequencing method may be used with the present methods including, for example, single-cell sequencing (sc)-seq, CITE-seq, bulk sequencing, next generation sequencing, nanopore sequencing, etc. The resulting sequencing data may include transcriptional data associated with one or more genes (for example, mRNA sequences, gene expression levels, etc.), genomic data associated with one or more genes (for example, DNA sequences, DNA variants, etc.), whole transcriptome data, whole exome data, and/or whole genome data, and combinations thereof. The sequences of the nucleic acid molecules in each sequencing library or pools of combined sequencing libraries may be provided as FASTQ files with sequencing reads. Sequences may be determined by analyzing the resulting sequence reads.

In some embodiments, the sequencing is accomplished using a next generation sequencer, such as a NextSeq 550, 10×, Illumina, or another sequencing instrument. The sequencer will generate FASTQ files comprising sequence reads. In some embodiments, the FASTQ files are 10× sc-seq FASTQ files containing sequencing reads for each cell, an index file, read 1 (R1) file, and read 2 (R2) file. In some embodiments, a quality control analysis is performed on the FASTQ files and the technical variability in the sequencing data is analyzed.

In some embodiments, the sequencer generates raw data in the base call (BCL) format, containing sequencing data from multiple pooled samples that were assayed in a single sequencing run. In one embodiment, a bioinformatics pipeline (for example, a pipeline that includes the cellranger mkfastq pipeline) may be used to demultiplex BCL files into FASTQ files for each individual library.

In some embodiments, read 1 and read 2 start at standard Illumina sequencing primer sites used in paired-end sequencing. Read 1 may be used to sequence the 16 bp 10× Barcode and 10 bp unique molecular identifiers (UMI), while read 2 may be used to sequence the cDNA fragment.

In some embodiments, the 10× barcode is a nucleic acid sequence that is unique to each cell in a specimen. In some embodiments, the UMI is a nucleic acid sequence that is unique to each nucleic acid molecule isolated from a cell and serves as a type of barcode sequence. The UMI may be added before a library amplification step. During bioinformatic analysis duplicate UMIs may be removed or deduplicated. In one embodiment, the Chromium i7 Sample Index Kit is utilized, and each sample index provided in the kit combines 4 different sequences in order to balance across all four nucleotides.

In some embodiments, the method may further include additional steps described in Hague et al, *Genome Medicine* 9, 75 (2017), which is incorporated by reference herein in its entirety.

In step 135 in the method of FIG. 1, the PDNA sequences are detected in the sequencing data to determine whether the target molecules were proximally located in the biological sample.

In step 135, the sequence reads may be filtered to find reads that are indicative of the presence of a multi-molecule biomarker in the biological sample (for example, feature sequences). For a non-limiting example of a bioinformatics pipeline that can be used to process sequencing data, see Example 2A. In one embodiment, modified software is used to detect a combination of two or more sequences specific to a particular PDNA (feature sequences, for example, sequences specific to the combination of AOTs joined with splint oligo(s), primer(s), capture oligos, etc.), such as, for example, two or more barcodes, which may be connected by spacer sequences of varying lengths. The modified software may comprise existing software designed to analyze sequencing data (for example, Cell Ranger), or a modified version of commercially available software.

In some embodiments, a sequence that is complementary to the sequence of the PDNA molecule or portions of the PDNA is used (termed herein an "anti-target") as a search string that can filter sequence reads to detect PDNA molecule sequences.

In some embodiments, sequence reads from the FASTQ file(s) may be filtered by searching for reads that correspond to one or more splint oligonucleotide sets and may generate a list of cell IDs (for example, 10× barcodes) and/or UMIs associated with a splint oligonucleotide set.

In some embodiments, the R1 and/or R2 reads are searched to detect feature sequences (for example, portions of the AOT oligonucleotides linked to another AOT, splint sequences, etc.) and/or combinations of two or more feature sequences. In some embodiments, two feature sequences may have approximately 5-100 nucleotides between them. In one embodiment, these combinations of feature sequences may be found within a read or pair of paired-end reads.

For each detected feature sequence or combination of feature sequences, a list of the cell IDs (for example, 10× barcodes) and/or UMIs associated with the feature may be saved to generate a list of cells having that feature and/or a list of nucleic acid molecules associated with that feature. In some embodiments, lists of cell IDs and UMIs associated with all feature sequences are saved. If a UMI and cell ID pair are on more than one list, (for example, associated with more than one feature sequence), the UMI and/or cell ID pair may be added to a list of UMIs and/or cell IDs associated with the combination of those feature sequences.

In embodiments utilizing a splint oligonucleotide, if the sequencing results include reads that correspond to a splint oligonucleotide sequence linked to a single AOT sequence, the results indicate the presence of a single target molecule. Alternatively, if the sequencing results include reads that correspond to a splint oligonucleotide sequence linked to two antibody-oligo sequences (for example, arranged as in the PDNA molecule of Example 1) or two AOT sequences without a splint oligonucleotide sequence (for example, arranged as in the PDNA molecule of Example 2A), the results indicate that two target molecules were in close proximity in the biological sample.

In step 140 in the method of FIG. 1, the detection of multi-molecule biomarkers in the biological sample is reported.

In some embodiments, the report will indicate whether one or more multi-molecule biomarkers were detected in the biological sample. The report may further include the number of nucleic acid molecules that were associated with each detected multi-molecule biomarker (or each of a subset of the detected multi-molecule biomarkers) and/or the number of cells in the sample associated with each detected multi-molecule biomarker (or each of a subset of the detected multi-molecule biomarkers). The report may further include the number of nucleic acid molecules and/or cells associated with single molecules or other biomarkers that were detected in the sample. The report may further include one or more diagnoses, prognoses, matched therapies and/or matched clinical trials based on the multi-molecule biomarkers or single molecule biomarkers detected, clinical data, and/or additional molecular data associated with the biological sample. For example, the report may include the identification of the cell, cell type, cell state/condition, etc., associated with the detected multi-molecule biomarker (or each of a subset of the detected multi-molecule biomarkers).

In step 145 in the method of FIG. 1, any suggested diagnoses, prognoses, matched therapies and/or matched clinical trials are optionally reported. This report may aid a physician or medical professional in making a medical care decision.

In step 150 in the method of FIG. 1, the results are optionally stored in a database. The database may further include additional molecular data, such as clinical data associated with the biological sample (for example, treatment response, diagnosis, prognosis, or survival data). The database may be used to discover novel associations between a multi-molecule biomarker and a particular prognosis, diagnosis, and/or treatment response. The novel association may be used to design an experiment using cell lines, organoids, animal models, and/or clinical trials to determine whether the association is coincidental or biologically relevant. The database may also be used to define patient cohorts or to select patients that may be eligible for a clinical trial.

Use with a Digital and Laboratory Health Care Platform

The methods and systems described herein may be utilized in combination with or as part of a digital and laboratory health care platform that is generally targeted to medical care and research. It should be understood that many uses of the methods and systems described above, in combination with such a platform, are possible. One example of such a platform is described in U.S. Patent Publication No. 2021/0090694, titled "Data Based Cancer Research and Treatment Systems and Methods", and published Mar. 25, 2021, which is incorporated herein by reference and in its entirety for any and all purposes.

For example, an implementation of one or more embodiments of the methods described herein may include microservices constituting a digital and laboratory health care platform supporting bioinformatic multi-molecule biomarker detection. Embodiments may include a single microservice for executing and delivering multi-molecule biomarker detection or may include a plurality of microservices each having a particular role which together implement one or more of the embodiments above. In one example, a first microservice may execute bioinformatics filtering to deliver a data file of PDNA associated sequences and metadata to a second microservice for report generation, which may include metadata analysis and/or cell type determination. Similarly, the second microservice may execute report generation to deliver a detected multi-molecule biomarker report according to an embodiment described above.

Where the embodiments described above are executed in one or more micro-services with or as part of a digital and laboratory health care platform, one or more of such microservices may be part of an order management system that orchestrates the sequence of events as needed at the appropriate time and in the appropriate order necessary to instantiate embodiments above. A micro-services based order management system is disclosed, for example, in U.S. Patent Publication No. 2020/80365232, titled "Adaptive Order Fulfillment and Tracking Methods and Systems", and published Nov. 19, 2020, which is incorporated herein by reference and in its entirety for all purposes.

For example, continuing with the above first and second microservices, an order management system may notify the first microservice that an order for bioinformatic filtering has been received and is ready for processing. The first microservice may execute and notify the order management system once the delivery of a data file of PDNA associated sequences and metadata is ready for the second microservice. Furthermore, the order management system may identify that execution parameters (prerequisites) for the second microservice are satisfied, including that the first microservice has completed, and notify the second microservice that it may continue processing the order to generate a report according to an embodiment described above.

Where the digital and laboratory health care platform further includes a genetic analyzer system, the genetic analyzer system may include targeted panels and/or sequencing probes. An example of a targeted panel is disclosed, for example, in U.S. Patent Publication No. 2021/0090694, titled "Data Based Cancer Research and Treatment Systems and Methods", and published Mar. 25, 2021, which is incorporated herein by reference and in its entirety for all purposes. An example of a targeted panel for sequencing cell-free (cf) DNA and determining various characteristics of a specimen based on the sequencing is disclosed, for example, in U.S. patent application Ser. No. 17/179,086, titled "Methods And Systems For Dynamic Variant Thresholding In A Liquid Biopsy Assay", and filed Feb. 18, 1921, U.S. patent application Ser. No. 17/179,267, titled "Estimation Of Circulating Tumor Fraction Using Off-Target Reads Of Targeted-Panel Sequencing", and filed Feb. 18, 1921, and U.S. patent application Ser. No. 17/179,279, titled "Methods And Systems For Refining Copy Number Variation In A Liquid Biopsy Assay", and filed Feb. 18, 1921 which is incorporated herein by reference and in its entirety for all purposes. In one example, targeted panels may enable the delivery of next generation sequencing results (including sequencing of DNA and/or RNA from solid or cell-free specimens) for bioinformatic multi-molecule biomarker detection according to an embodiment, above. An example of the design of next-generation sequencing probes is disclosed, for example, in U.S. Patent Publication No. 2021/0115511, titled "Systems and Methods for Next Generation Sequencing Uniform Probe Design", and published Jun. 22, 2021 and U.S. patent application Ser. No. 17/323,986, titled "Systems and Methods for Next Generation Sequencing Uniform Probe Design", and filed May 18, 1921, which are incorporated herein by reference and in their entirety for all purposes.

Where the digital and laboratory health care platform further includes an epigenetic analyzer system, the epigenetic analyzer system may analyze specimens to determine their epigenetic characteristics and may further use that information for monitoring a patient over time. An example of an epigenetic analyzer system is disclosed, for example, in U.S. patent application Ser. No. 17/352,231, titled "Molecular Response And Progression Detection From Circulating Cell Free DNA", and filed Jun. 18, 1921, which is incorporated herein by reference and in its entirety for all purposes.

Where the digital and laboratory health care platform further includes a bioinformatics pipeline, the methods described above may be utilized after completion or substantial completion of the methods utilized in the bioinformatics pipeline. As one example, the bioinformatics pipeline may receive next-generation genetic sequencing results and return a set of binary files, such as one or more BAM files, reflecting DNA and/or RNA read counts aligned to a reference genome. The methods and systems described above may be utilized, for example, to ingest the DNA and/or RNA read counts and produce multi-molecule biomarker detection as a result.

When the digital and laboratory health care platform further includes an RNA data normalizer, any RNA read counts may be normalized before processing embodiments as described above. An example of an RNA data normalizer is disclosed, for example, in U.S. Patent Publication No. 2020/0098448, titled "Methods of Normalizing and Correcting RNA Expression Data", and published Mar. 26, 2020, which is incorporated herein by reference and in its entirety for all purposes.

When the digital and laboratory health care platform further includes a genetic data deconvolver, any system and method for deconvolving may be utilized for analyzing genetic data associated with a specimen having two or more biological components to determine the contribution of each component to the genetic data and/or determine what genetic data would be associated with any component of the specimen if it were purified. An example of a genetic data deconvolver is disclosed, for example, in U.S. Patent Publication No. 2020/0210852, published Jul. 2, 2020, and PCT/US19/69161, filed Dec. 31, 2019, both titled "Transcriptome Deconvolution of Metastatic Tissue Samples"; and U.S. patent application Ser. No. 17/074,984, titled "Calculating Cell-type RNA Profiles for Diagnosis and Treatment", and filed Oct. 20, 2020, the contents of each of which are incorporated herein by reference and in their entirety for all purposes.

RNA expression levels may be adjusted to be expressed as a value relative to a reference expression level. Furthermore, multiple RNA expression data sets may be adjusted, prepared, and/or combined for analysis and may be adjusted to avoid artifacts caused when the data sets have differences because they have not been generated by using the same methods, equipment, and/or reagents. An example of RNA data set adjustment, preparation, and/or combination is disclosed, for example, in U.S. patent application Ser. No. 17/405,025, titled "Systems and Methods for Homogenization of Disparate Datasets", and filed Aug. 18, 2021.

When the digital and laboratory health care platform further includes an automated RNA expression caller, RNA expression levels associated with multiple samples may be compared to determine whether an artifact is causing anomalies in the data. An example of an automated RNA expression caller is disclosed, for example, in U.S. Pat. No. 11,043,283, titled "Systems and Methods for Automating RNA Expression Calls in a Cancer Prediction Pipeline", and issued Jun. 22, 2021, which is incorporated herein by reference and in its entirety for all purposes.

The digital and laboratory health care platform may further include one or more insight engines to deliver information, characteristics, or determinations related to a disease state that may be based on genetic and/or clinical data associated with a patient, specimen and/or organoid. Exemplary insight engines may include a tumor of unknown origin (tumor origin) engine, a human leukocyte antigen (HLA) loss of homozygosity (LOH) engine, a tumor mutational burden engine, a PD-L1 status engine, a homologous recombination deficiency engine, a cellular pathway activation report engine, an immune infiltration engine, a microsatellite instability engine, a pathogen infection status engine, a T cell receptor or B cell receptor profiling engine, a line of therapy engine, a metastatic prediction engine, an IO progression risk prediction engine, and so forth.

An example tumor origin or tumor of unknown origin engine is disclosed, for example, in U.S. patent application Ser. No. 15/930,234, titled "Systems and Methods for Multi-Label Cancer Classification", and filed May 12, 1920, which is incorporated herein by reference and in its entirety for all purposes.

An example of an HLA LOH engine is disclosed, for example, in U.S. Pat. No. 11,081,210, titled "Detection of Human Leukocyte Antigen Class I Loss of Heterozygosity in Solid Tumor Types by NGS DNA Sequencing", and issued Aug. 3, 2021, which is incorporated herein by reference and in its entirety for all purposes. An additional example of an HLA LOH engine is disclosed, for example, in U.S. patent application Ser. No. 17/304,940, titled "Detection of Human Leukocyte Antigen Loss of Heterozygosity", and filed Jun. 28, 2021, which is incorporated herein by reference and in its entirety for all purposes.

An example of a tumor mutational burden (TMB) engine is disclosed, for example, in U.S. Patent Publication No. 2020/0258601, titled "Targeted-Panel Tumor Mutational Burden Calculation Systems and Methods", and published Aug. 13, 2020, which is incorporated herein by reference and in its entirety for all purposes.

An example of a PD-L1 status engine is disclosed, for example, in U.S. Patent Publication No. 2020/0395097, titled "A Pan-Cancer Model to Predict The PD-L1 Status of a Cancer Cell Sample Using RNA Expression Data and Other Patient Data", and published Dec. 17, 2020, which is incorporated herein by reference and in its entirety for all purposes. An additional example of a PD-L1 status engine is disclosed, for example, in U.S. Pat. No. 10,957,041, titled "Determining Biomarkers from Histopathology Slide Images", issued Mar. 23, 2021, which is incorporated herein by reference and in its entirety for all purposes.

An example of a homologous recombination deficiency engine is disclosed, for example, in U.S. Pat. No. 10,975,445, titled "An Integrative Machine-Learning Framework to Predict Homologous Recombination Deficiency", and issued Apr. 13, 2021, which is incorporated herein by reference and in its entirety for all purposes. An additional example of a homologous recombination deficiency engine is disclosed, for example, in U.S. patent application Ser. No. 17/492,518, titled "Systems and Methods for Predicting Homologous Recombination Deficiency Status of a Specimen", filed Oct. 1, 2021, which is incorporated herein by reference and in its entirety for all purposes.

An example of a cellular pathway activation report engine is disclosed, for example, in U.S. Patent Publication No. 2021/0057042, titled "Systems And Methods For Detecting Cellular Pathway Dysregulation In Cancer Specimens", and published Feb. 25, 2021, which is incorporated herein by reference and in its entirety for all purposes.

An example of an immune infiltration engine is disclosed, for example, in U.S. Patent Publication No. 2020/0075169, titled "A Multi-Modal Approach to Predicting Immune Infiltration Based on Integrated RNA Expression and Imaging Features", and published Mar. 5, 2020, which is incorporated herein by reference and in its entirety for all purposes.

An example of an MSI engine is disclosed, for example, in U.S. Patent Publication No. 2020/0118644, titled "Microsatellite Instability Determination System and Related Methods", and published Apr. 16, 2020, which is incorporated herein by reference and in its entirety for all purposes. An additional example of an MSI engine is disclosed, for example, in U.S. Patent Publication No. 2021/0098078, titled "Systems and Methods for Detecting Microsatellite Instability of a Cancer Using a Liquid Biopsy", and published Apr. 1, 2021, which is incorporated herein by reference and in its entirety for all purposes.

An example of a pathogen infection status engine is disclosed, for example, in U.S. Pat. No. 11,043,304, titled "Systems And Methods For Using Sequencing Data For Pathogen Detection", and issued Jun. 22, 2021, which is incorporated herein by reference and in its entirety for all purposes. Another example of a pathogen infection status engine is disclosed, for example, in PCT/US21/18619, titled "Systems And Methods For Detecting Viral DNA From Sequencing", and filed Feb. 18, 2021, which is incorporated herein by reference and in its entirety for all purposes.

An example of a T cell receptor or B cell receptor profiling engine is disclosed, for example, in U.S. patent application Ser. No. 17/302,030, titled "TCR/BCR Profiling Using Enrichment with Pools of Capture Probes", and filed Apr. 21, 2021, which is incorporated herein by reference and in its entirety for all purposes.

An example of a line of therapy engine is disclosed, for example, in U.S. Patent Publication No. 2021/0057071, titled "Unsupervised Learning And Prediction Of Lines Of Therapy From High-Dimensional Longitudinal Medications Data", and published Feb. 25, 2021, which is incorporated herein by reference and in its entirety for all purposes.

An example of a metastatic prediction engine is disclosed, for example, in U.S. Pat. No. 11,145,416, titled "Predicting likelihood and site of metastasis from patient records", and issued Oct. 12, 2021, which is incorporated herein by reference and in its entirety for all purposes.

An example of an IO progression risk prediction engine is disclosed, for example, in U.S. patent application Ser. No. 17/455,876, titled "Determination of Cytotoxic Gene Signature and Associated Systems and Methods For Response Prediction and Treatment", and filed Nov. 19, 2021, which is incorporated herein by reference and in its entirety for all purposes.

When the digital and laboratory health care platform further includes a report generation engine, the methods and systems described above may be utilized to create a summary report of a patient's genetic profile and the results of one or more insight engines for presentation to a physician. For instance, the report may provide to the physician information about the extent to which the specimen that was sequenced contained tumor or normal tissue from a first organ, a second organ, a third organ, and so forth. For example, the report may provide a genetic profile for each of the tissue types, tumors, or organs in the specimen. The genetic profile may represent genetic sequences present in the tissue type, tumor, or organ and may include variants, expression levels, information about gene products, or other information that could be derived from genetic analysis of a tissue, tumor, or organ.

The report may include therapies and/or clinical trials matched based on a portion or all of the genetic profile or insight engine findings and summaries. For example, the therapies may be matched according to the systems and methods disclosed in U.S. patent application Ser. No. 17/546,049, titled "Artificial Intelligence Driven Therapy Curation and Prioritization", filed Dec. 9, 2021, which is incorporated herein by reference and in its entirety for all purposes. For example, the clinical trials may be matched according to the systems and methods disclosed in U.S. Patent Publication No. 2020/0381087, titled "Systems and Methods of Clinical Trial Evaluation", published Dec. 3, 2020, which is incorporated herein by reference and in its entirety for all purposes.

The report may include a comparison of the results (for example, molecular and/or clinical patient data) to a database of results from many specimens. An example of methods and systems for comparing results to a database of results are disclosed in U.S. Patent Publication No. 2020/0135303 titled "User Interface, System, And Method For Cohort Analysis" and published Apr. 30, 2020, and U.S. Patent Publication No. 2020/0211716 titled "A Method and Process for Predicting and Analyzing Patient Cohort Response, Progression and Survival", and published Jul. 2, 2020, which is incorporated herein by reference and in its entirety for all purposes. The information may be used, sometimes in conjunction with similar information from additional specimens and/or clinical response information, to match therapies likely to be successful in treating a patient, discover biomarkers or design a clinical trial.

Any data generated by the systems and methods and/or the digital and laboratory health care platform may be downloaded by the user. In one example, the data may be downloaded as a CSV file comprising clinical and/or molecular data associated with tests, data structuring, and/or other services ordered by the user. In various embodiments, this may be accomplished by aggregating clinical data in a system backend and making it available via a portal. This data may include not only variants and RNA expression data, but also data associated with immunotherapy markers such as MSI and TMB, as well as RNA fusions.

When the digital and laboratory health care platform further includes a device comprising a microphone and speaker for receiving audible queries or instructions from a user and delivering answers or other information, the methods and systems described above may be utilized to add data to a database the device can access. An example of such a device is disclosed, for example, in U.S. Patent Publication No. 2020/0335102, titled "Collaborative Artificial Intelligence Method and System", and published Oct. 22, 2020, which is incorporated herein by reference and in its entirety for all purposes.

When the digital and laboratory health care platform further includes a mobile application for ingesting patient records, including genomic sequencing records and/or results even if they were not generated by the same digital and laboratory health care platform, the methods and systems described above may be utilized to receive ingested patient records. An example of such a mobile application is disclosed, for example, in U.S. Pat. No. 10,395,772, titled "Mobile Supplementation, Extraction, And Analysis Of Health Records", and issued Aug. 27, 2019, which is incorporated herein by reference and in its entirety for all purposes. Another example of such a mobile application is disclosed, for example, in U.S. Pat. No. 10,902,952, titled "Mobile Supplementation, Extraction, And Analysis Of Health Records", and issued Jan. 26, 2021, which is incorporated herein by reference and in its entirety for all purposes. Another example of such a mobile application is disclosed, for example, in U.S. Patent Publication No. 2021/0151192, titled "Mobile Supplementation, Extraction, And Analysis Of Health Records", and filed May 20, 2021, which is incorporated herein by reference and in its entirety for all purposes.

When the digital and laboratory health care platform further includes organoids developed in connection with the platform (for example, from the patient specimen), the methods and systems may be used to further evaluate genetic sequencing data derived from an organoid and/or the organoid sensitivity, especially to therapies matched based on a portion or all of the information determined by the systems and methods, including predicted cancer type(s), likely tumor origin(s), etc. These therapies may be tested on the organoid, derivatives of that organoid, and/or similar organoids to determine an organoid's sensitivity to those therapies. Any of the results may be included in a report. If the organoid is associated with a patient specimen, any of the results may be included in a report associated with that patient and/or delivered to the patient or patient's physician or clinician. In various examples, organoids may be cultured and tested according to the systems and methods disclosed in U.S. Patent Publication No. 2021/0155989, titled "Tumor Organoid Culture Compositions, Systems, and Methods", published May 27, 2021; PCT/US20/56930, titled "Systems and Methods for Predicting Therapeutic Sensitivity", filed Oct. 22, 2020; U.S. Patent Publication No. 2021/0172931, titled "Large Scale Organoid Analysis", published Jun. 10, 2021; PCT/US2020/063619, titled "Systems and Methods for High Throughput Drug Screening", filed Dec. 7, 2020 and U.S. patent application Ser. No. 17/301,975, titled "Artificial Fluorescent Image Systems and Methods", filed Apr. 20, 2021 which are each incorporated herein by reference and in their entirety for all purposes. In one example, the drug sensitivity assays may be especially informative if the systems and methods return results that match with a variety of therapies, or multiple results (for example, multiple equally or similarly likely cancer types or tumor origins), each matching with at least one therapy.

When the digital and laboratory health care platform further includes application of one or more of the above in combination with or as part of a medical device or a laboratory developed test that is generally targeted to medical care and research, such laboratory developed test or medical device results may be enhanced and personalized through the use of artificial intelligence. An example of laboratory developed tests, especially those that may be enhanced by artificial intelligence, is disclosed, for example, in U.S. Patent Publication No. 2021/0118559, titled "Artificial Intelligence Assisted Precision Medicine Enhancements to Standardized Laboratory Diagnostic Testing", and published Apr. 22, 2021, which is incorporated herein by reference and in its entirety for all purposes.

It should be understood that the examples given above are illustrative and do not limit the uses of the methods described herein in combination with a digital and laboratory health care platform.

Exemplary Uses

A prognosis, diagnosis, therapy, and/or clinical trial may be assigned to a patient based on the detection of one or more multi-molecule biomarkers in a biological sample in combination with clinical or experimental data indicating that the presence or absence of a particular multi-molecule biomarker is associated with a particular prognosis, diagnosis, and/or positive treatment response to a particular therapy (for example, a reduction in the growth rate of cancer cells). Such associations can be identified using, for example, in vitro experiments.

One of the non-limiting advantages of the methods disclosed herein is that they utilize proximity detection. In other words, rather than simply detecting the presence of two or more molecules in a sample, they detect the presence of two or more molecules only when they are in close proximity. Proximity detection can provide information about the activation state of a protein or molecular pathway. For example, proximity detection can be used to detect co-localization of proteins that interact to form a functional protein complex, such as two more receptors that form a hetero-dimeric complex to initiate a particular cellular pathway. Further, proximity detection can be used to detect molecular modifications, such as phosphorylation or glycosylation that lead to the activation or inactivation of certain proteins and/or pathways. Still further, proximity detection can be used to detect biomarkers that are indicative of a particular cell type or disease status. Thus, in some embodiments, detection of the PDNA by the methods provides information on cell type and/or cell state/condition.

In some cases, the molecules detected via PDNA may not be indicative of cell type. Thus, in some embodiments, the methods comprise identifying the cell type in which the PDNA was detected using single-cell RNA sequencing. Methods of using single-cell RNA sequencing to phenotype cells are known in the art. See Mol Cell 58(4):610-20, 2015 (in particular, the section titled "Identifying and Describing Cellular Subpopulations"), which is hereby incorporated by reference in its entirety.

In some embodiments, two or more antibodies are used to detect the multi-molecule biomarkers; that is, in some embodiments, the methods use antibodies against different components that form a multi-molecule biomarker. For example, a pair of antibodies, antibody A and antibody B, could be used to detect the formation of a heterodimeric receptor complex if antibody A specifically binds to one of the receptor proteins that forms the complex and antibody B specifically binds to the other receptor protein. Alternatively, a pair of antibodies could be used to detect phosphorylation of a particular protein if antibody A specifically binds to the phosphorylated portion of the protein and antibody B specifically binds to the same protein at a different site (for example, a different portion of the same protein molecule).

The methods and compositions of the present disclosure can be applied to cell, organoid, and tissue development systems, for example, to identify a particular cell stage or lineage in a differentiation pathway of a multi-potent cell, to determine cell state, cell number, or cell condition (for example, in drug testing or therapeutic efficacy determination), or can be applied to drug delivery systems, for example, systems that involve carrying a therapeutic protein or therapeutic cell to a target tissue or target cell.

In addition, while the present technology is useful as a substitute for multivalent antibodies, it is also useful as a tool for multivalent antibody development. For example, the proximity detection compositions and methods disclosed herein can be used to assess whether the target epitopes are ever localized closely enough for a multivalent antibody to bind the distinct antigens at the same time, and to determine what cell types the target epitopes colocalize in. Pairs of closely localized targets greatly enhance the binding affinity and efficacy of therapeutic bivalent/multivalent antibodies. The proximity detection system would help to prioritize which pairs of epitopes are best suited for targeting when designing a bivalent/multivalent antibody. Like the proximity detection compositions and methods of the present technology, multivalent antibodies provide differentiation between cell types (for instance cancer detection) by detecting molecular combinations that are distinct to the cell type of interest, and can be used as carriers to bring a therapeutic protein into contact with a target disease (for example, cancer) cell.

Target Molecules

In various embodiments, the multi-molecule biomarker comprises two or more target molecules.

In some embodiments, at least one of the target molecules comprises a protein. In some embodiments, at least one of the molecules is a cell surface protein. Such proteins may include, for example, cancer cell markers, immune cell markers, or any other biomarkers that signal a particular cellular state, activity, or inactivity. By way of example, but not by way of limitation, a multi-molecule biomarker is a combination of two or more molecules including at least one of the following: CD274, CD16, CD56, CD4, CD8a, CD19, CD20, CD21, CD19, CD25, CD279, CD278, CD137, CD127, CD273, CD14, CD117, CD152, CD223, CD134, CD141, CD34, CD45, and CD3.

In some embodiments, at least one of the target molecules comprises a sugar moiety such as a carbohydrate or another saccharide molecule. Suitable sugar moieties include, but are not limited to, glycoproteins, glycolipids, and lipopolysaccharides. For example, suitable sugar moieties include glycol-antigens, viral glycans (for example, the glycan shield of an HIV glycoprotein), tumor epitopes, glycolipid and blood group A antigens, internal epitopes of bacterial lipopolysaccharides, terminal epitopes on polysaccharides, and linear homopolysaccharides.

In some embodiments, at least one of the target molecules comprises a lipid. By way of example, but not by way of limitation, such molecules include glycolipids, lipopolysaccharides and phospholipids.

In some embodiments, at least one of the target molecules comprises a post-translational modification (PTM). Suitable PTMs include, without limitation, methylation, acetylation, ubiquitylation, phosphorylation, sumoylation, ribosylation, and citrullination. For example, in some embodiments, the first AOT binds to a protein or DNA sequence of interest and the second AOT binds to a PTM such that detection of the PDNA indicates that the protein or DNA sequence has been post-translationally modified with the target PTM.

Kits

In some embodiments, kits are provided for the identification and detection of multi-molecule biomarkers. In some embodiments, a kit includes two or more AOTs, and optionally one or more of: one or more splint oligonucleotides, a primer oligonucleotide, and a capture oligonucleotide.

EXEMPLARY EMBODIMENTS

The present application provides the following exemplary embodiments.

Embodiment 1. A method comprising: (a) providing a first antibody-oligo tag (AOT) comprising a first antibody and a first oligonucleotide, and a second AOT comprising a second antibody and a second oligonucleotide; wherein the first antibody of the first AOT binds a first target in a biological sample, and the second antibody of the second AOT binds a second target in the biological sample; wherein the first oligonucleotide of the first AOT comprises a first hybridization region, and the second oligonucleotide of the second AOT comprises a second hybridization region, and wherein the first and second hybridization regions are complementary and hybridize to each other under hybridization conditions thereby forming a proximity detection nucleic acid (PDNA); (b) contacting, in a reaction vessel, the biological sample and the first and second AOTs under conditions that allow for binding of the first and second antibodies to their respective targets; (c) providing hybridization conditions to the reaction vessel wherein the complementary regions of the first and second oligonucleotides form the PDNA if the first and second targets are in proximity in the biological sample; and (d) detecting the PDNA.

Embodiment 2. A method comprising: (a) providing a first antibody-oligo tag (AOT) comprising a first antibody and a first oligonucleotide, and a second AOT comprising a second antibody and a second oligonucleotide; wherein the first antibody of the first AOT binds a first target in a biological sample, and the second antibody of the second AOT binds a second target in the biological sample; and wherein the first oligonucleotide of the first AOT comprises a first hybridization region and the second oligonucleotide of the second AOT comprises a second hybridization region; (b) providing a splint oligonucleotide, wherein the splint oligonucleotide comprises a first complementary splint region (CSR) that is complementary to the first hybridization region of the first AOT and a second CSR that is complementary to the second hybridization region of the second AOT, wherein the first and second hybridization regions hybridize to the first and second CSRs under hybridization conditions thereby forming a proximity detection nucleic acid (PDNA); (c) contacting, in a reaction vessel, the biological sample and the first and second AOTs under conditions that allow for binding of the first and second antibodies to their respective targets; (d) adding the splint oligonucleotide to the reaction vessel; (e) providing hybridization conditions to the reaction vessel wherein the hybridization regions of the first and second oligonucleotides of the first and second AOTs hybridize to the first and second CSRs of the splint oligonucleotide and form the PDNA if the first and second targets are in proximity in the biological sample; and (f) detecting the PDNA.

Embodiment 3. A method comprising: (a) providing a first antibody-oligo tag (AOT) comprising a first antibody and a first oligonucleotide, and a second AOT comprising a second antibody and a second oligonucleotide; wherein the first antibody of the first AOT binds a first target in a biological sample, and the second antibody of the second AOT binds a second target in the biological sample; wherein the first oligonucleotide of the first AOT comprises a first and a second hybridization region, and the second oligonucleotide of the second AOT comprises a third and a fourth hybridization region; (b) providing a primer oligonucleotide comprising a primer region and a region complementary to the first hybridization region of the first AOT; (c) providing a capture oligonucleotide comprising a capture region and a region complementary to the third hybridization region of the second AOT; (d) providing a splint oligonucleotide comprising (i) a first complementary splint region (CSR), wherein the first CSR is complementary to the second hybridization region of the first AOT, and (ii) a second CSR, wherein the second CSR is complementary to the fourth hybridization region of the second AOT; (e) contacting, in a reaction vessel, the biological sample and the first and second AOTs under conditions that allow for binding the first and second antibodies to their respective targets; (f) adding the primer oligonucleotide, the capture oligonucleotide, and the splint oligonucleotides to the reaction vessel; (g) providing hybridization conditions in the reaction vessel wherein the first and second hybridization regions of the first AOT and the third and fourth hybridization regions of the second AOT hybridize to the primer oligonucleotide, the capture oligonucleotide, and the splint oligonucleotide to form a PDNA if the first and second targets are in proximity in the biological sample; and (h) detecting the PDNA.

Embodiment 4. The method of any one of embodiments 1-3, wherein the first and second antibodies bind different targets on the same molecule.

Embodiment 5. The method of any one of embodiments 1-3, wherein the first and second antibodies bind different targets on different molecules.

Embodiment 6. The method of any one of embodiments 1-3, wherein the first and second targets are expressed on the surface of one or more cells.

Embodiment 7. The method of any one of embodiments 1-3, wherein the first and second targets are expressed on the surface of the same cell.

Embodiment 8. The method of any one of embodiments 1-3, wherein at least one of the first or second targets comprises a protein.

Embodiment 9. The method of any one of embodiments 1-3, wherein at least one of the first or second targets comprises a sugar.

Embodiment 10. The method of any one of embodiments 1-3, wherein at least one of the first or second targets comprises a phosphate.

Embodiment 11. The method of any one of embodiments 1-3, wherein at least one of the first or second targets is a cancer biomarker and is expressed on the surface of a cancer cell.

Embodiment 12. The method of any one of embodiments 1-3, wherein at least one of the first or second targets is selected from the group consisting of CD274, CD16, CD56, CD4, CD8a, CD19, CD20, CD21, CD19, CD25, CD279, CD278, CD137, CD127, CD273, CD14, CD117, CD152, CD223, CD134, CD141, CD34, CD45, and CD3.

Embodiment 13. The method of any one of embodiments 1-3, wherein the first and second AOT oligonucleotides comprise one or more barcode sequences.

Embodiment 14. The method of embodiment 13, wherein at least one barcode sequence on the first oligonucleotide is different from at least one barcode sequence on the second oligonucleotide sequence.

Embodiment 15. The method of embodiment 13, wherein at least one barcode sequence on the first AOT is associated with the antibody on the first AOT, wherein at least one barcode sequence on the second AOT is associated with the antibody on the second AOT, and wherein the first antibody and the second antibody are different.

Embodiment 16. The method of any one of embodiments 1-3, further comprising providing N additional AOTs in step (a), wherein each of the additional AOTs comprise an antibody that binds to a different target, and wherein each of these different targets is different than the target of the first and second AOT antibodies.

Embodiment 17. The method of any one of embodiments 1-3, wherein detecting the PDNA comprises sequencing at least a portion of the PDNA.

Embodiment 18. The method of embodiment 17, wherein sequencing comprises high-throughput sequencing.

Embodiment 19. The method of any one of embodiments 1-3, wherein detecting the PDNA comprises detecting a product that was amplified using polymerase chain reaction.

Embodiment 20. The method of any one of embodiments 1-3 further comprising providing at least one mask oligonucleotide in step (a), wherein the sequence of the mask oligonucleotide is complementary to at least one of the hybridization regions on the first or second oligonucleotide of the first or second AOT.

Embodiment 21. The method of embodiment 3, wherein forming the PDNA comprises a ligation reaction.

Embodiment 22. The method of any one of embodiments 1-3, wherein forming the PDNA comprises a polymerization reaction.

Embodiment 23. The method of any one of embodiments 1-3, wherein the first and second oligonucleotides are approximately 5 to 100 nucleotides long, about 10-50, about 15-30, or about 20-25 nucleotides long.

Embodiment 24. The method of embodiment 2 or 3, wherein the splint oligonucleotide is approximately 5 to 100 nucleotides long, about 10-50, about 15-30, or about 20-25 nucleotides long.

Embodiment 25. The method of embodiment 2 or 3, wherein the splint oligonucleotide comprises two or more separate splint oligonucleotides.

Embodiment 26. The method of embodiment 22, wherein the two or more separate splint oligonucleotides comprise additional CSRs such that the two or more separate oligonucleotides hybridize together under hybridization conditions.

Embodiment 27. The method of embodiment 1, comprising providing N additional AOTs in step (a), wherein each of the additional AOTs comprise an antibody that binds to a different target, wherein each of these different targets is different than the target of the first and second AOT antibodies, and wherein each of the N oligonucleotides of the N AOTs comprises a hybridization region that hybridizes with the first hybridization region of the first AOT.

Embodiment 28. The method of embodiment 2, comprising: providing N additional AOTs in step (a), wherein each of the additional AOTs comprise an antibody that binds to a different target, wherein each of these different targets is different than the target of the first and second AOT antibodies; providing N additional splint oligonucleotides, wherein each splint oligonucleotide comprises two hybridization regions, each hybridization region complementary to a hybridization region of at least one AOT; and wherein each of the oligonucleotides of the N AOTs comprise a hybridization region complementary to a hybridization region of at least one of the N splint oligonucleotides.

Embodiment 29. The method of any one of embodiments 1-3, wherein one or more of the oligonucleotides comprises a detectable label.

Embodiment 30. The method of any one of embodiments 1-3 further comprising identifying the cell type in which the PDNA was detected using single-cell RNA sequencing.

Embodiment 31. A kit comprising two or more antibody-oligo tags (AOTs) and optionally comprising one or more of: a splint oligonucleotide, a primer oligonucleotide, and a capture oligonucleotide.

EXAMPLES

The following Examples are illustrative and are not intended to limit the scope of the claimed subject matter.

Example 1: Formation of PDNA Using a Splint Oligonucleotide

This example refers to FIG. 2 and describes a non-limiting embodiment that is illustrated in FIG. 2. In this embodiment, a 10× R2 primer site ("R2") is linked to the first end of a first nucleic acid molecule (represented by a solid line). The second end of the first nucleic acid molecule hybridizes to a first antibody-oligo at a first site. The first end of a second nucleic acid molecule (represented by a curved, dashed line, termed a splint oligo) hybridizes to a first antibody-oligo at a second site, and the second end of the second nucleic acid molecule hybridizes to a second antibody-oligo at a third site. A first end of a third nucleic acid molecule (represented by a solid line) hybridizes to a second antibody-oligo at a fourth site and a second end of the third nucleic acid molecule is attached to a capture sequence ("capture seq."). The length of the second nucleic acid molecule may be adjusted. In various embodiments, as the length of the second nucleic acid molecule decreases, the distance between the first and second antibody-oligo tags detected by the systems and methods may decrease. In one embodiment, the length of the second nucleic acid molecule is approximately 5 to 100 nucleotides long.

Portions of the nucleotide sequence of the first, second, and third nucleic acid molecules may be selected to be complementary to a portion of the sequence of an oligo, which may be antibody conjugated. For example, a first sequence of the first antibody-oligo may be selected to be the first site, and the sequence of the second end of the first nucleic acid molecule may be selected to be complementary to the first site, resulting in Watson-Crick base pairing between the oligo and the first nucleic acid molecule.

In FIG. 2, the first antibody-oligo tag is represented here by the blue Y-shaped cartoon and the second antibody-oligo tag is represented here by the red Y-shaped cartoon. Each antibody is linked to an oligo represented here by a nucleotide sequence. In this example, the nucleotide sequence shown is the feature sequence. Each end of the feature sequence may have additional bases that are not shown (for example, the sequences shown may only represent the middle portion of the oligo sequence). In this embodiment, the system is illustrated to be compatible with 10× Genomics' single-cell sequencing methods for high-throughput detection. Accordingly, "R2" represents the 10× R2 primer site and "capture seq." represents a sequence used during the capture step of preparing a sequencing library.

In this example, the 5' and 3' ends of the R2, splint, and capture oligonucleotides are ligated to form a single oligonucleotide comprising the R2 primer oligo, the splint oligo, and the capture sequence oligo.

In some embodiments, one or more additional primer sequences may be provided along with polymerase to generate a double-stranded PDNA, and/or to provide PDNA amplification products. In some embodiments, one or more primer or oligonucleotide may be labeled.

In some embodiments, the single-stranded ligation product (PDNA) is detected by sequencing.

Example 2A: Formation of PDNA without a Splint Oligonucleotide

This example refers to FIG. 3 and describes a non-limiting embodiment that is illustrated in FIG. 3. As with the example above, the steps and components described in this example detect protein proximity using a 10×-reaction-compatible system. In brief, the 10× Genomics' Chromium™ Single Cell 5' kit uses reverse transcription followed by oligo-switching to add a barcode to the 5'-end of RNA molecules.

Figure 3A:
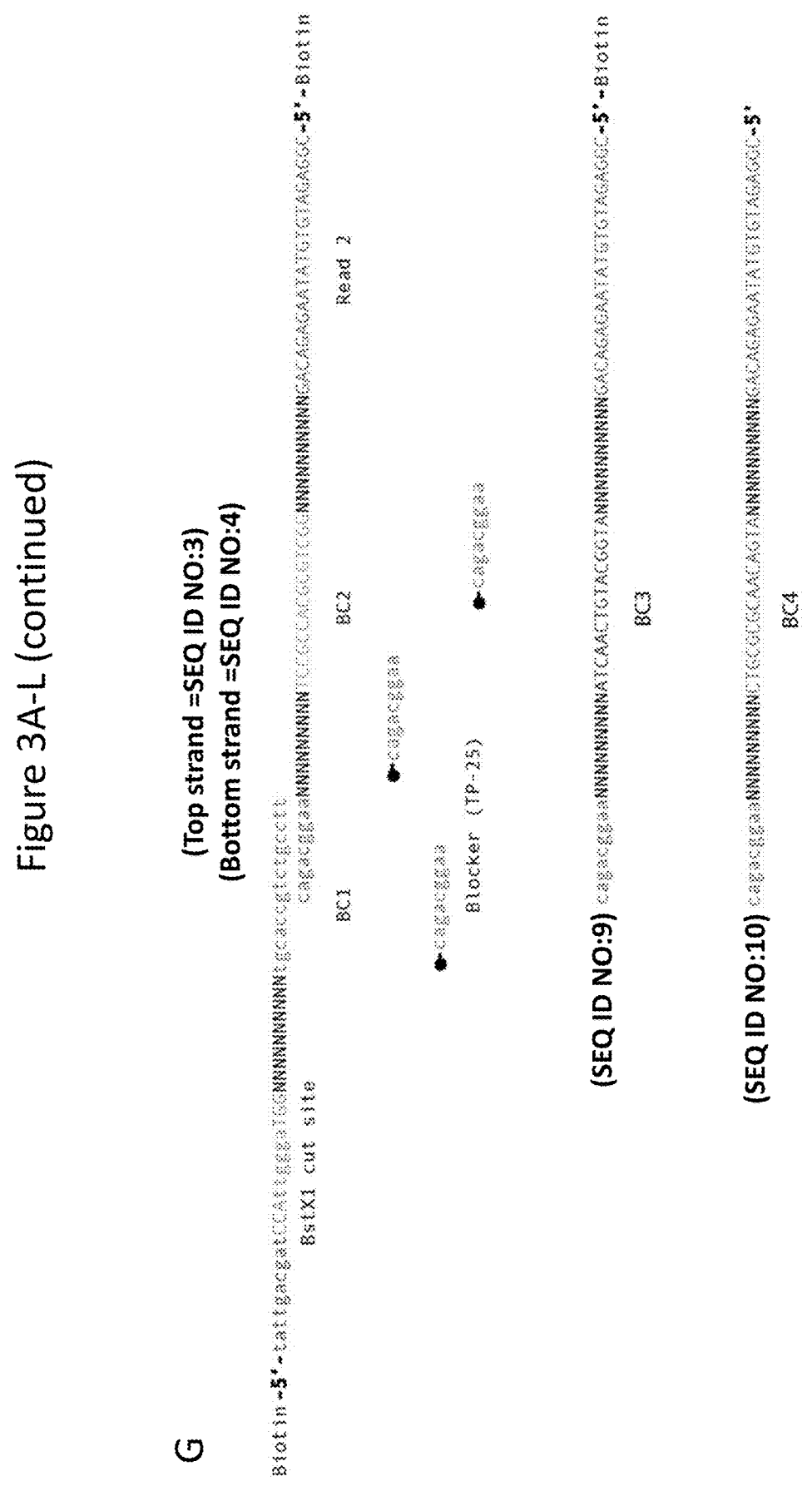

In this example, two antibody-oligo conjugates, referred to as antibody-oligo tags (AOTs), are used to detect two antigens. When these antigens are in close proximity the oligos can anneal and several enzymatic steps are used to convert the annealed complex to a barcoded product for sequencing. FIG. 3A illustrates an example of two antibody-oligo tags (AOTs). In this example, the first AOT oligonucleotide includes a sequence that is compatible for hybridizing with a complementary region in the second AOT oligonucleotide. In various embodiments, each compatible sequence may be located near the end of the oligonucleotide that is not conjugated to the antibody.

In this non-limiting example, the compatible sequence is a unique barcode sequence, "BC1" in the first oligonucleotide that is conjugated to the first antibody (red) in the upper left corner, and a complementary BC1 sequence (@BC1) is present in the second oligonucleotide which is conjugated to the second antibody (orange) in the lower right corner. In this example, the first AOT is termed "bait", and the second AOT is termed "query". It is understood that other complementary sequences may be used instead of the BC1 and @BC1 sequences.

The oligonucleotide in the first AOT in the top left corner of FIG. 3A may include several features, including a unique barcode such as BC1. In this example, the BC1 region is a barcode (useful for identification), and also serves to hybridize to a proximal AOT in a later step.

In various embodiments, it is desirable to avoid premature annealing of the AOT oligonucleotides, which can result in "hitch-hiking". For example, if the orange antibody AOT anneals to the red antibody AOT prior to binding to its antigen, the orange antibody may be dragged to the cell surface along with the red antibody, even if the antigen of the orange antibody is not present. This may cause a false positive result. The present method uses two strategies (that can be used together or alternatively) to minimize such hitch-hiking. The first strategy is to wash with 37° C. wash buffer. This will allow melting of the annealed site and dilution as orange redistributes into the wash buffer volume.

The second strategy is to block the annealing sites of the AOTs using a competing oligonucleotide, referred to herein as a "mask oligo" or a "blocker". Suitably, the mask oligos (1) anneal to the complementary regions on the AOTs, (2) have a melting temperature (Tm) between room temperature and 37° C. (for example, Tm=27° C.), and (3) have a chemical modification at their 3'-end to keep them from being used by DNA polymerase or reverse transcriptase for extension. In some embodiments, blocking groups may include dideoxy-Cytosine (www.idtdna.com/site/Catalog/Modifications/Category/7). Other blocking groups well-known in the art may be used if the 3'-most nucleotide is not a C.

Thus, in this example, when the AOTs are introduced to the specimen and bind to their respective target molecules, at least one of the complementary regions (BC1 and @BC1 in this example) is masked by a short mask oligo (shown in FIG. 3 as a black circle connected to a short oligo including the sequence 5'-aaggcagac-3'). Binding of a mask oligo to at least one of the complementary regions prevents other oligonucleotides from hybridizing to it until the mask oligo is removed, thereby reducing hitch-hiking.

Several different query AOTs can be introduced in the same detection reaction. For example, in a pool of query AOTs, each query AOT may include a unique barcode associated with its unique antibody. However, each query AOT may have the same complementary portion. Thus, the pool of different query AOTs can be used to form PDNAs with the bait AOT that can be distinguished by sequencing, based on the barcode associated with a particular antibody. In some embodiments, there is more than one bait AOT.

In this example, query antibodies carry a unique BCN (BC2), the R2 sequence used in the 10× system, and a region that anneals to the bait antibody BC1 sequence (in this example, the @BC1 region). In this example, the @BC1 sequence is also masked (the mask oligo is not shown here). In this example, the hybridization region is identical in length to the mask and is designed to anneal at a temperature of approximately 20° C. (room temperature).

In some embodiments, the initial antibody binding reaction is done with a molar excess of mask and at 4° C. This will increase the likelihood that the bait BC does not anneal to the query antibodies and recruit them via Watson-Crick base pairing.

Mask removal is depicted in FIG. 3B. Once antibodies are attached to a surface at 4° C. and washed in the presence of mask, the mask may be removed. This is done by increasing the temperature to approximately 37° C. to melt and wash off the mask (to this end, centrifuging and handling may be done at approximately 37° C. and buffers may be used at approximately 37° C.).

FIG. 3C illustrates an example of the BC1 (complementary) sequence of the orange AOT annealing to the previously blocked BC1 sequence of the red AOT.

After the sequences have annealed, the single-stranded DNA is converted to double-stranded DNA (dsDNA). In one embodiment, this conversion step includes filling in with DNA polymerase. The temperature is returned to room temperature, which allows hybridization of overlapped nucleic acid sequences and still supports the activity of a DNA polymerase (for example, Klenow Fragment (3'->5' exo- or Bsu DNA Polymerase)). The DNA polymerase may add dNTPs to all single-stranded DNA in this figure to generate the dsDNA shown in FIG. 3D. The method is not limited by the choice of DNA polymerase, and the skilled artisan will understand that another DNA polymerase may be used.

The PDNA is then prepared for detection by sequencing. The DNA polymerase and excess dNTPs are removed by washing, and then the PDNA can be cut with a restriction enzyme, such as with BstXI at 37° C.

Cutting with BstXI (Cut site: CCANNNNN|NTGG (SEQ ID NO:107)) allows a 4-bp 3'-overhang that is capable of functioning like the CCC overhang that is added by MMLV-RT to cDNA-3' during the 10× reverse transcription (RT) reaction that occurs in droplets.

The samples can then be washed at 4° C. and the cells can be put into droplets for 10× sequencing.

FIG. 3E illustrates the use of RT to fill-in the switch-oligo and pick up the cellular barcode.

Once a cell enters the droplet, it will be placed at 55° C. (standard 10× reaction). This should cause the antibodies to dissociate from their targets and the overhang fragments to separate. In this embodiment, we rely on the switch oligo concentration to out-compete the query antibody overhang end for binding. Additionally, we rely on the RT enzyme to fill-in the DNA primed, DNA template at 55° C. in the droplet.

The final product (155 bp) is shown in FIG. 3F and is R1 . . . R2 DNA with a Cell BC, molecular id, ½ switch oligo-½ BstX1 hybrid site, and BC1, and BC2. This molecule should only form when two antibodies (AOTs) are in close proximity. During the initial antibody binding, steps are taken to ensure that premature oligonucleotide hybridization will not happen, thereby preventing false positives, for example by hitchhiking. Therefore, the antibody binding depends solely on the antibody affinity for its target.

Example 2B: Validation of the Method Described in Example 2A

This example describes the experiments that were performed to test the method for detecting protein proximity described in Example 2A.

For this validation experiment, the AOTs include biotin in the place of the antibodies. This allowed the inventors to test chemical reactions on a magnetic bead surface rather than a cell surface, and to bypass making the various antibody-oligo species. In addition to generating biotinylated versions of the red AOT ("bio-red", which includes the BC1 sequence, as shown in FIG. 3G) and orange AOT ("bio-orange", which includes the BC2 sequence and BC1-complementary sequence, as shown in FIG. 3G) shown in FIG. 3A, the inventors also generated a biotinylated blue AOT ("bio-blue", which includes the BC3 sequence and BC1-complementary sequence as shown in FIG. 3G) and an unbiotinylated green AOT (including the BC4 sequence and BC1-complementary sequence shown in FIG. 3G) for use as controls, see FIG. 3G.

In this example, if the bio-orange, bio-blue, or green AOT are proximal to bio-red, (for example, if bio-red and bio-orange both bind to a magnetic bead via their biotin molecule) the BC1 sequence of the bio-red AOT could anneal to the BC1-complementary sequence of the bio-orange, bio-blue, or green AOT. Because the green AOT is not biotinylated, it should not be proximal to any of the other AOTs and should not form a PDNA. Thus, it is a negative control and if the green BC4 sequence is detected, that indicates that a false positive hitch-hiker event occurred and the protocol may need to be further optimized (for example, via modification of the mask oligo application and/or washing steps) to reduce false positives. The mask oligo is referred to as "blocker" in the following exemplary protocol.

Materials and Methods:

Bead preparation: Wash 100 ul of Streptavidin-C1 magnetic beads 4× with cold wash buffer (PBS+0.02% tween-20). Resuspend in 200 μl wash buffer.

Prepare four starting condition combinations as follows:
1) bio-Red+bio-Orange: mimics co-localization of molecules on bead surface; notably, this condition contains no blocker oligo, so the bio-Red-bio-Orange interaction could be the result of hitchhiking.
   +85 μl wash buffer RT buffer
   +2.7 μl (10 μM stock) bio-red (TP23)
   +2.7 μl (10 μM stock) bio-orange (TP24)
   Incubate 10 min, RT to allow annealing⇒place on ice.
2) bio-Red+blocker, then add bio-Blue: comparison of this reaction to reaction 1 indicates whether use of the blocker reduces hitch-hiker signal.
   +85 μl wash buffer RT buffer
   +2.7 μl (10 μM stock) bio-red (TP23)
   +2.7 μl (100 μM stock) blocker (TP25)

Incubate 10 minutes, RT to allow annealing⇒place on ice.
+2.7 µl (10 µM stock) bio-blue (TP36)
3) bio-Red+Green: strict hitch-hiker control; note: Green may be removed by warm washes before PDNA can form.
+85 µl wash buffer RT buffer
+2.7 µl (10 µM stock) bio-red (TP23)
+2.7 µl (10 µM stock) bio-green (TP35)
Incubate 10 minutes, RT to allow annealing⇒place on ice.
4) Equal part mix of reactions 1-3: allows the species to compete in same reaction
Use a separate tube for each step.
+27 µl reaction 1+0.9 µl Blocker (TP25) place on ice
+27 µl reaction 3+0.9 µl Blocker (TP25) place on ice
+27 µl reaction 2=place on ice
Combine the three volumes together to create reaction 4.
Add 38 µl washed beads to reaction 1-4. Mix by pipetting and leave on ice for 30 minutes. Flick every 10 minutes to mix. Wash 4× with 37° C. wash buffer+block (41 µl blocker [100 µM] per 2 ml wash buffer). Magnet and wash buffer must be in water bath to keep the temperature at 37° C. Incubation on magnet etc. is in water bath. Material is now attached to beads and can be frozen overnight if necessary.
PCR Fill-In:
Magnetize beads on ice. Remove all supernatant, resuspend in 10 µl wash buffer. Move to clean PCR tube.
Prepare PCR Master Mix (no primers) and heat activate it (95° C., 5 min)
+8.4 µl H2O
+70 µl KOD 2× buffer
+30 µl dNTPs (KOD extreme kit)
+4.4 µl enzyme (KOD extreme)
Combine:
+16 µl heat-activated master mix⇒aliquot into strip tubes in chilled metal block
+4 µl resuspended reaction beads
Place on thermocycler preheated to 22° C., incubate for 10 minutes, and then chill at 4° C. or on ice. [C1000 machine, root>FILLIN_1_STE]
3× wash with cold wash buffer, resuspend in 4 µl and move to fresh tube.
Material is now dsDNA (see FIG. 3D) and can be frozen overnight if necessary.
BstX1 Cut:
Prepare BstX1 master mix:
+78 µl H2O
+12 µl Buffer 3.1
+6 µl BstX1
Combine:
+16 µl Bstx1 master mix
+4 µl beads
37° C., 60 minute reaction. [C1000 machine, root>BSTX1]
3× wash with cold wash buffer, resuspend in 10 µl wash buffer.
Material is now dsDNA with cut end and can be frozen overnight if necessary.
RT Reaction Using 10× Kit to Add Barcode:
Prepare RT Master Mix:
+262.5 µl RT reagent mix
+7.5 µl switch oligo (TP20 [50 µM], replaces switch oligo emitted by 10× beads)
+23.5 µl H2O
+12.6 µl Additive A
+52.5 µl RT enzyme mix B Combine:
+68.3 µl RT Master Mix
+22 µl H2O
+10 µl beads (post BstX1)
10× RT step thermocycler protocol. [C100 small machine, recent>10×RT]
3× wash with wash buffer. Resuspend in 10 µl wash buffer.
Material is now nicked dsDNA and can be frozen overnight if necessary.
PCR Detection:
Prepare PCR Master Mix:
+30 µl H2O
+75 µl 2×KOD buffer
+30 µl dNTPs (2 mM, KOD kit)
+4.5 µl F primer (10 µM, TP22)
+4.5 µl R primer (10 µM, TP21)
+3.0 µl enzyme (KOD extreme)
Combine:
+25 µl PCR Master Mix
+5 µl beads
Use proximity detection protocol on thermocycler. [C1000 Root>PROX2_CHECK]
Magnetize beads and keep supernatant.
Material is now dsDNA (see FIG. 3F) and can be frozen overnight if necessary.
This material is ready for running on 2% agarose to detect a 155 bp product. Gel purify and zero blunt topo clone (KAN) for sequencing.
Sequence with M13F primer.
All reactions will typically show product. But reaction 4 (a mix of reactions 1, 2, and 3) allows us to evaluate the various species in competition.

Following the PCR fill-in reaction, the resulting dsDNA from one of the reactions (approximately 155 bp long) was run on an agarose gel. During a run, an electric current will push dsDNA molecules from the starting position (near the top of each gel pictured here) toward the opposite edge of the gel, and the distance that each molecule is pushed depends on the length of the molecule, such that dsDNA molecules of approximately the same length were moved by the electric current to approximately similar locations during the run, resulting in a "band" appearing like a horizontal stripe. If a band contained a larger number of dsDNA molecules, it could appear brighter (more intense) than a band containing a smaller number of dsDNA molecules. Each gel had a standard ladder in the leftmost lane (column), having a mix of dsDNA molecules having known lengths indicated as numbers to the left of the ladder in FIG. 3I (for example, 300, 200, 150, 100, etc. bp). As shown in FIG. 3I, no difference could be detected between the reactions that included blockers and those that did not, indicating that the mask oligo application and/or removal may need to be further optimized to reduce hitchhiking.

In FIG. 3J, various combinations of biotinylated (denoted by a "bio-" prefix) and unbiotinylated (denoted by the lack of a "bio-" prefix) versions of the red and orange AOTs were combined to test for non-specific binding and to compare various versions of the protocol. For example, reactions were compared to determine whether hitchhiking could be reduced using warm washes, blocker oligos, or both warm washes and blocker oligos. The results indicate that using a combination of warm washes and blocker oligos may suppress hitchhiking (compare lane 7 to lanes 2, 4-6, and 8-9).

Similarly, in FIG. 3K, biotinylated (denoted by a "bio-" prefix) or unbiotinylated (denoted by the lack of a "bio-" prefix) versions of the red and orange AOTs were combined to test various versions of the protocol. This gel indicates that the use of blocker oligos with or without a warm wash (with either cold or warm washes) may suppress hitchhiking.

In FIG. 3L, various annealing temperatures were tested to identify an annealing temperature that produced the least background signal caused by non-specific amplification (that is, amplification of molecules that may not be PDNAs or may not indicate proximity) without affecting amplification of the PDNAs. The results of this gel indicate that the ideal annealing temperature for PDNA generation may be in the range of approximately 45 to 58° C.

A schematic of the sequencing reads generated by using an M13F primer to sequence the dsDNA product of each reaction in this validation experiment is depicted in FIG. 3H. For reaction 1, 4/4 red-orange interactions were detected. For reaction 2, 4/4 red-blue interactions were detected. For reaction 3, 3/3 red-green interactions and 1 junk interaction were detected. For reaction 4 (the combination of reactions 1-3, where each reaction is allowed to compete), 15/17 red-orange interactions, 2/17 red-blue interactions, no red-green interactions, and 1 junk interaction were detected.

The sequencing results for reactions 1-3 demonstrate that the overall strategy and reaction steps work. The results for reaction 4 indicate that warm washing is effective for removing hitchhiker (green) AOTs. Blocking also reduced detection of species that can localize to the surface, doing so in close proximity to red at about 1/10th the rate when blocker is used, as is indicated by the reduced occurrence of red-blue (2/17) compared to red-orange (15/17). Non-colocalized detection is probably a high estimate as the oligo concentrations are 10 µM, likely considerably higher than antibody concentrations would be, and therefore more likely to randomly land close to each other on the bead surface during the validation experiment than during actual application of the systems and methods disclosed above.

Example 3: Example of Sequencing Reads Generated by the Present Methods

Figure 4:
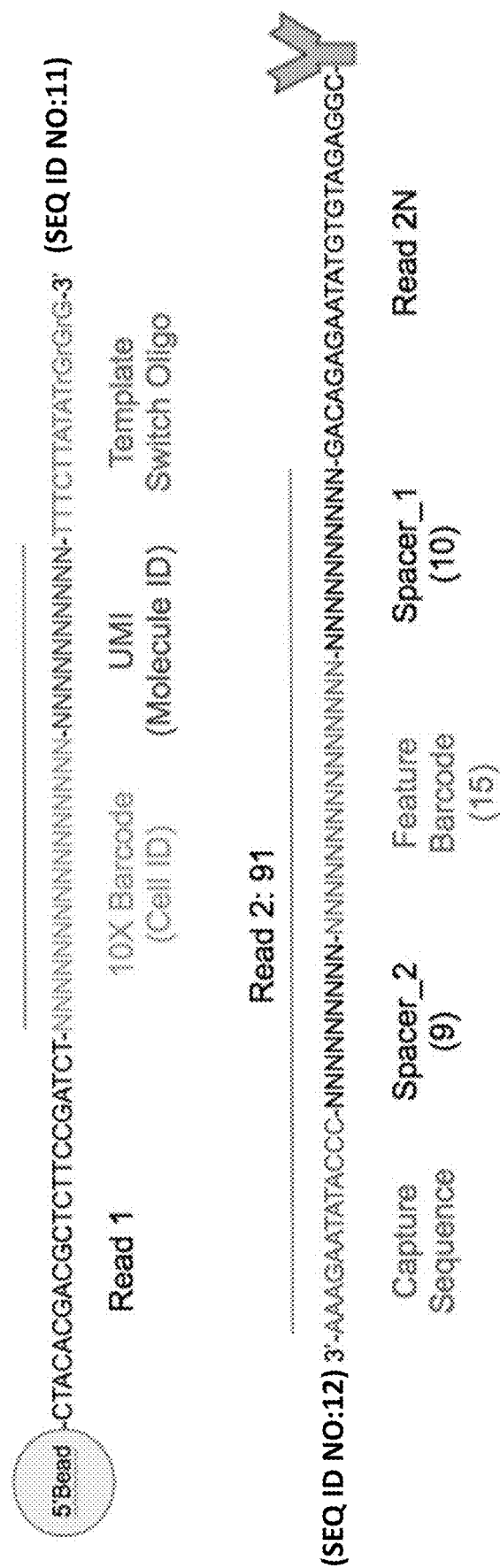
FIG. 4 is a schematic illustrating the exemplary sequencing reads described in Example 3.

This example refers to FIG. 4 and describes a non-limiting embodiment that is illustrated in FIG. 4.

FIG. 4 illustrates an example of an R1 and an R2 sequencing read. In FIG. 4, the R1 sequencing read is 26 bases long and the R2 sequencing read is 91 bases long. Each read is represented by the sequence shown below each solid line. The sequencer reads 26 bp from the R1 primer site and 91 bp from the R2 primer site. For another example of an R1 and an R2 sequencing read, see FIG. 3F.

In this example, the R1 sequencing read comprises the sequences of the 10× Barcode (unique to each cell) and the UMI (unique molecular identifier, unique to each nucleic acid isolated from a cell). Attached to the 5' end of the nucleic acid sequence represented by the R1 sequencing read, is the read 1 primer site and a bead, which may not be included in the R1 sequencing read. Attached to the 3' end of the nucleic acid sequence represented by the R1 sequencing read is a template switch oligo, which may not be included in the R1 sequencing read.

In this example, the R2 sequencing read comprises a first spacer sequence (spacer 1), feature barcode (which may be unique to the antibody), a second spacer sequence (spacer 2), and a capture sequence (used during nucleic acid capture for generating the sequencing library). Attached to the 5' end of the nucleic acid sequence represented by the R2 sequencing read is the read 2 primer site and an antibody, which may not be included in the R2 sequencing read.

In various embodiments, the R1 and R2 files are synchronized such that a set of paired-end reads (a read 1 and paired read 2) will be located in corresponding rows in a set of paired files. For example, for a paired R1 and R2 file, a read 2 located in the third row of the R2 file is the paired read of the read 1 located in the third row of the R1 file.

In various embodiments, the systems and methods may generate a file combining the paired-end reads to generate one R1R2 read and store them in an R1R2 file having one R1R2 read per row. For an example of an R1R2 file, see FIG. 8A.

Example 4: Example of Antibody Targets and Conjugated Feature Sequences

This example refers to FIG. 5 and describes a non-limiting embodiment that is illustrated in FIG. 5.

FIG. 5 illustrates examples of feature sequences. In this example, there are at least 24 classes of antibody-oligo tags that may have been mixed with the biological specimen. In greater detail, there is at least one class of antibody-tags that binds to each of the following target molecules: CD274, CD16, CD56, CD4, CD8a, CD19, CD20, CD21, CD19, CD25, CD279, CD278, CD137, CD127, CD273, CD14, CD117, CD152, CD223, CD134, CD141, CD34, CD45, and CD3. For each antibody tag, the feature sequence of the conjugated oligo is listed to the right of the target molecule of the antibody. Each feature sequence has a 10 nucleotide spacer (spacer 1) attached to a first end of the sequence or combination of sequences, represented by {10,10} and a 9 nucleotide spacer (spacer 2) attached to a second end of the sequence or combination of sequences, represented by {9,9}. Lines 14 through 16 represent three combinations of feature sequences that comprise a proximity detection nucleic acid molecule. Each of these combinations includes an antibody-oligo tag that targets CD19 and an antibody-oligo tag that targets CD21, having varying spacing between the two antibody-oligo tag feature sequences (for example, 9, 27, or 70 nucleotides between the two oligo tag feature sequences, represented by {9,9},{27,27}, and {70,70}, respectively). In this example, lines 14, 15, and 16 each include a capture sequence (CCCATATAAGAAA (SEQ ID NO:105)) that was truncated and is not fully shown in the figure.

Example 5: Example of Bioinformatics Pipeline Structure

Figure 6:
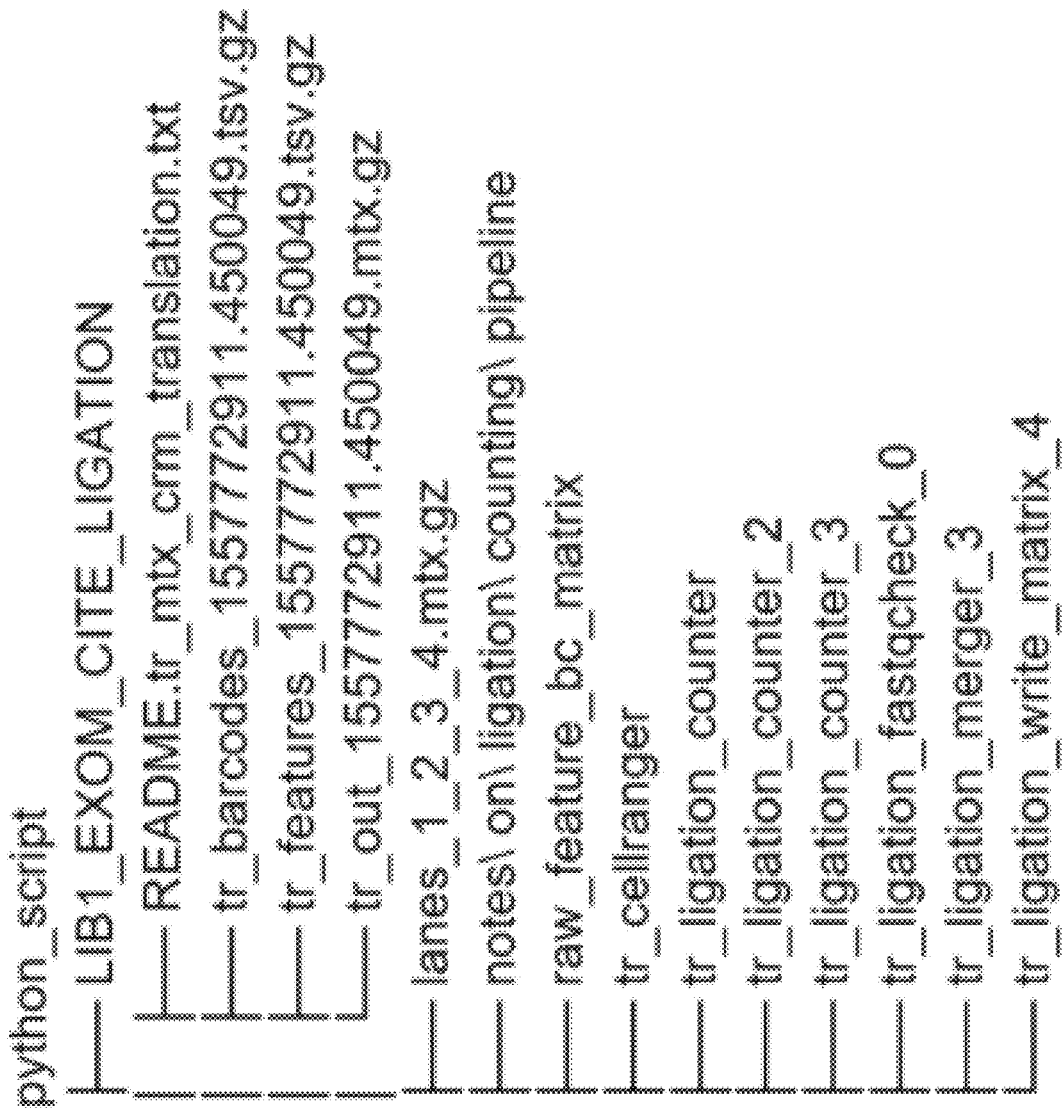
FIG. 6 is an exemplary pipeline architecture for analyzing single cell RNA-seq data to detect two or more molecules located in close proximity in a biological specimen. This pipeline is described in Example 5.

This example refers to FIG. 6 and describes a non-limiting embodiment that is illustrated in FIG. 6.

FIG. 6 illustrates an example pipeline structure for analyzing single cell RNA-seq data to detect two or more molecules located in close proximity in a biological specimen.

In this example, gzip (.gz) files are compressed (zipped) files.

The "barcodes . . . tsv.gz" file is a cellranger output file known in the art. The file is formatted as a matrix where each column represents a barcode sequence, each row represents a feature (for example, an antibody tag conjugated with a detectable nucleic acid sequence), and each entry represents the number of Unique Molecular Identifiers (UMIs) associated with a feature-barcode pair. The file may be filtered to only show detected barcodes.

The "features . . . tsv.gz" file is a cellranger output file known in the art. The file is formatted as a matrix where each row represents a feature and various columns represent the feature ID, feature name, feature type, etc.

The "out . . . mtx.gz" file is a cellranger matrix output file known in the art.

For a description of cellranger software, see support.10x genomics.com/single-cell-vdj/software/analysis-of-multiple-libraries/latest/overview, the contents of which are incorporated herein by reference in their entirety.

The "lanes_1_2_3_4.mtx.gz file is a matrix file generated by the first four lanes on a sequencer flow cell. In this example, each lane in the sequencer generates a corresponding Index file, R1 FASTQ file, and R2 FASTQ file. The index files may be discarded and the R1 and R2 files may be analyzed.

The raw_feature_bc_matrix is a matrix of feature sequences, also known as a feature set (for example, see Example 4).

In this example, the FASTQ files may be synchronized (for example, lines in R1 files and R2 files are from the same paired-end read). The systems and methods may include a counter that searches for feature sequences defined in a ligation feature file (using more flexible regular expression/regex definitions) to look up the corresponding cell barcode and/or UMI info (for example, in R1 file or R1R2 file).

In this example, ligation_counter, ligation_counter_2, and ligation_counter_3 each search portions of a FASTQ file instead of searching the entire file. The systems and methods may include multiple cycles, where each cycle involves python reading in a chunk of the FASTQ (for example, R2) file, matching it against the feature set. Chunking the file offers the advantage of allowing the sequence chunks to be processed in parallel rather than sequentially.

In one embodiment, if a match is found, the systems and methods retrieve the relevant information (cell_id and/or umi) from the R1 file.

FASTQ files include a code for the quality of data at each position along the read. Thus, one way to assess data quality is to filter for reads that have few or no low-quality characters in the quality control string. In this example, tr_ligation_fastqcheck_0 compares the quality score associated with the relevant read in the R1 file to a quality threshold. If the information is high quality (for example, if the quality score exceeds the quality threshold), the systems and methods may store the information in a dictionary (key is cell_id, value is list of UMIs).

In this example, tr_write_matrix_4 outputs a matrix of cell_id and/or UMIs associated with each feature sequence or selected combinations of feature sequences.

For each feature sequence, the systems and methods may record the search result data, including associated cell barcode(s) and/or UMI(s) in any sequence reads having a feature sequence or paired with a read having a feature sequence. In various embodiments, the systems and methods may record the search result data in a dictionary: cell_id=> [umi_1, umi_2 . . . ]. In one embodiment, each dictionary name may be a cell ID (the 10× barcode associated with a cell), and the keys may be UMIs (the sequence associated with a unique nucleic acid molecule isolated from the biological specimen).

In various embodiments, the systems and methods may delete duplicate UMIs to generate a sparse matrix file, a feature file (columns from the matrix file) and cell barcodes file (rows from the matrix file).

In various embodiments, the cell_id may be ambiguous if Ns are allowed, and any N's in the barcode region may be excluded.

In one embodiment, UMIs with Ns may be excluded. In another embodiment, two UMIs having one mismatch are classified as equivalent.

In various embodiments, the molecule definitions will use regular expressions (specifically regex package which allows for fuzzy matching). This will provide a more flexible way to find molecular signatures.

In various embodiments, the pipeline includes a create_proximity_detector( ) command or function. The definition for create_proximity_detector( ) and the output from running create_create-proximity-detector( ) provides the sequence used for the experiment, given a barcode A and barcode B (for example, antibody barcodes depicted in FIGS. 2 and 5) and a desired spacer length, which may be used as a search string to detect a PDNA in sequencing results.

Example 6: Example of Results

This example refers to FIG. 7 and describes a non-limiting embodiment that is illustrated in FIG. 7.

FIG. 7 illustrates two search strings. In one example, the search strings may be generated by a command, for example, create_proximity_detector( ). The first search string (SEQ ID NO:42) is the sequence of the 10× R2 primer site, followed by a spacer of 10 N bases (spacer 1 from FIG. 4), a feature sequence (CD19 feature sequence in line 16 of FIG. 5; this feature sequence is also the reverse complement of the CD19 feature sequence in line 11 of FIG. 5), a spacer of 70 N bases (also referenced in line 16 of FIG. 5), a feature sequence (CD21 feature sequence in line 16 of FIG. 5; this feature sequence is also the reverse complement of the CD21 feature sequence in line 13 of FIG. 5), a spacer of 9 N bases (also referenced in line 16 of FIG. 5), and a capture sequence (shown in FIG. 4 and present in line 16 of FIG. 5, but not shown because line 16 was truncated). The second search string (SEQ ID NO:43) has a 10 N base spacer (spacer 1), a feature sequence (CD19 feature sequence in line 16 of FIG. 5; this feature sequence is also the reverse complement of the CD19 feature sequence in line 11 of FIG. 5), a spacer of 70 N bases (also referenced in line 16 of FIG. 5), a feature sequence (CD21 feature sequence in line 16 of FIG. 5; this feature sequence is also the reverse complement of the CD21 feature sequence in line 13 of FIG. 5), a spacer of 9 N bases (also referenced in line 16 of FIG. 5), and a capture sequence (shown in FIG. 4 and present in line 16 of FIG. 5, but not shown because line 16 was truncated). In this example, the search strings matched 132 results (output: "132"), representing 132 R1R2 reads that include the two feature sequences, separated by a 70 bp spacer. In various embodiments, unique search strings are generated for each feature sequence and for selected combinations of feature sequences and the step of searching the sequence results is repeated for each feature sequence and selected combinations of feature sequences.

Genetic sequence information may be detected from the biological specimen using techniques known in the art such as next-generation sequencing or single-cell sequencing. FIG. 8 shows exemplary genetic sequencing information detected from a biological specimen.

Figure 8A:
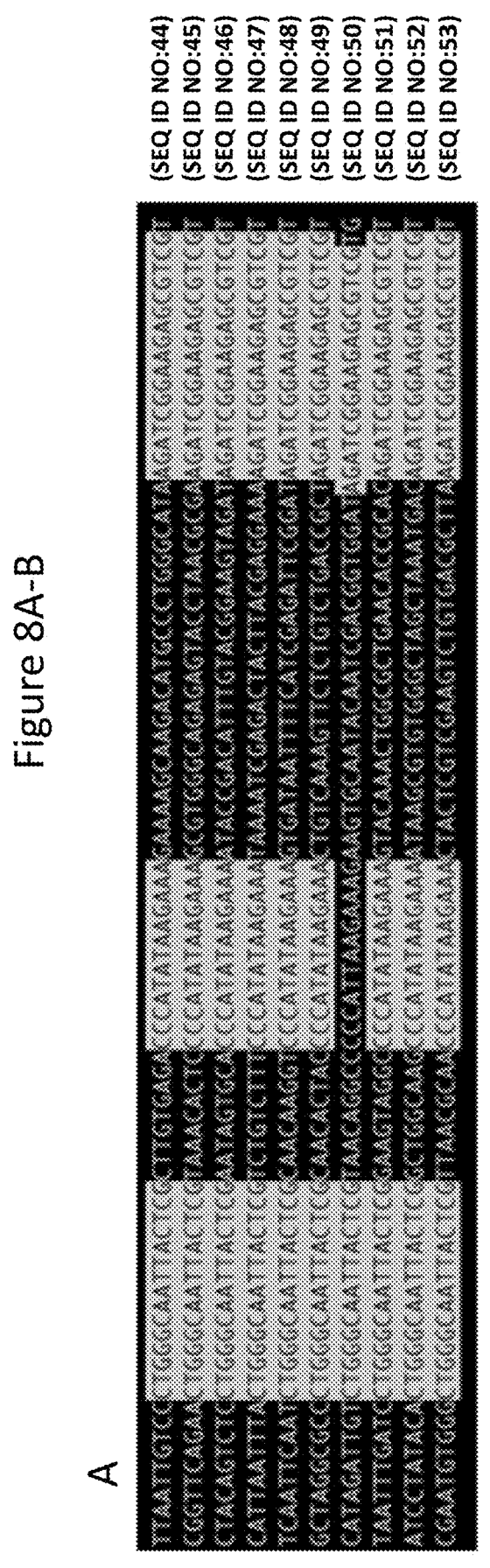

FIG. 8A illustrates an example of combined paired-end reads (read 1 and read 2 sequences originating from a 10× R1 and R2 primer sites, respectively. See Example 3). Each row in the results represents a combined R1R2 sequence read. The first 10 bp represent spacer 1, the next 15 bp highlighted in gray represent the feature barcode (in this example, associated with CD19 antibody), the next 9 bp represent spacer 2, the next 13 bp represent the capture sequence, the next 26 bp represent the UMI&10x barcode, the next 22 bp represent the read_1 primer site. In this example, the feature barcode is a portion of an oligo conjugated to an antibody (see Examples 1, 2, and 4).

In this example, the order of anti-target is: 5'CGGAGATGTGTATAAGAGACAG (SEQ ID NO:106) [10N][reverse complement ^ of target barcode][9-90N SPACER][reverse complement ^ of target barcode][CC-CATATAAGAAA (SEQ ID NO:105)].

FIG. 8B illustrates R2 reads. Sites where ligation may occur (including feature sequences) are colored red. Each row represents an R2 read. The first 10 base pairs are spacer 1, the next 15 base pairs are the feature sequence (colored red) associated with a CD19 antibody, followed by a 9, 27, or 70 base pair spacer, then the feature sequence (colored red) associated with a CD21 antibody, then a 9 base pair spacer, followed by the capture sequence.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

All methods described herein can be performed in any suitable order unless otherwise indicated herein or otherwise clearly contradicted by context. The use of any and all examples provided herein, is intended merely to better illuminate the invention and does not pose a limitation on the scope of the invention unless otherwise claimed. No language in the specification should be construed as indicating any non-claimed element as essential to the practice of the invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

It will be understood by one of ordinary skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components are packaged separately for commercialization and that useful commercial kits may contain any subset of the reaction components of the invention.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method comprising:
a) providing a first antibody-oligo tag (AOT) comprising a first antibody and a first oligonucleotide, and a second AOT comprising a second antibody and a second oligonucleotide;
wherein the first antibody of the first AOT binds a first target in a biological sample, and the second antibody of the second AOT binds a second target in the biological sample;
wherein the first oligonucleotide of the first AOT comprises a first hybridization region, and the second oligonucleotide of the second AOT comprises a second hybridization region; and
wherein the first oligonucleotide of the first AOT comprises a restriction enzyme recognition site for BstXI and said site is located 5' to the first hybridization region;
b) providing a splint oligonucleotide, wherein the splint oligonucleotide comprises a first complementary splint region (CSR) that is complementary to the first hybridization region of the first AOT and a second CSR that is complementary to the second hybridization region of the second AOT, wherein the first and second hybridization regions hybridize to the first and second CSRs under hybridization conditions thereby forming a proximity detection nucleic acid (PDNA) that comprises at least one double-stranded portion and at least two single-stranded portions;
c) contacting, in a reaction vessel, the biological sample and the first and second AOTs under conditions that allow for binding of the first and second antibodies to their respective targets;
d) adding the splint oligonucleotide to the reaction vessel;
e) providing hybridization conditions to the reaction vessel wherein the hybridization regions of the first and second oligonucleotides of the first and second AOTs hybridize to the first and second CSRs of the splint oligonucleotide and form the PDNA if the first and second targets are in proximity in the biological sample;
f) contacting the PDNA with a DNA polymerase and deoxyribonucleotide triphosphates (dNTPs) to fill in the single-stranded portions of the PDNA, thereby forming a double-stranded PDNA;

g) cutting the double-stranded PDNA with BstXI to form a cut PDNA comprising a single-stranded 3'-overhang; and h) detecting the cut PDNA using single-cell sequencing.

2. A method comprising:

a) providing a first antibody-oligo tag (AOT) comprising a first antibody and a first oligonucleotide, and a second AOT comprising a second antibody and a second oligonucleotide;

wherein the first antibody of the first AOT binds a first target in a biological sample, and the second antibody of the second AOT binds a second target in the biological sample;

wherein the first oligonucleotide of the first AOT comprises a first and a second hybridization region, and the second oligonucleotide of the second AOT comprises a third and a fourth hybridization region; and wherein the first oligonucleotide of the first AOT comprises a restriction enzyme recognition site for BstXI and said site is located 5' to the first hybridization region;

b) providing a primer oligonucleotide comprising a primer region and a region complementary to the first hybridization region of the first AOT;

c) providing a capture oligonucleotide comprising a capture region and a region complementary to the third hybridization region of the second AOT;

d) providing a splint oligonucleotide comprising
  a first complementary splint region (CSR), wherein the first CSR is complementary to the second hybridization region of the first AOT, and
  a second CSR, wherein the second CSR is complementary to the fourth hybridization region of the second AOT;

e) contacting, in a reaction vessel, the biological sample and the first and second AOTs under conditions that allow for binding the first and second antibodies to their respective targets;

f) adding the primer oligonucleotide, the capture oligonucleotide, and the splint oligonucleotides to the reaction vessel;

g) providing hybridization conditions in the reaction vessel wherein the first and second hybridization regions of the first AOT and the third and fourth hybridization regions of the second AOT hybridize to the primer oligonucleotide, the capture oligonucleotide, and the splint oligonucleotide to form a PDNA if the first and second targets are in proximity in the biological sample;

h) contacting the PDNA with a DNA polymerase and deoxyribonucleotide triphosphates (dNTPs) to fill in the single-stranded portions of the PDNA, thereby forming a double-stranded PDNA;

i) cutting the double-stranded PDNA with BstXI to form a cut PDNA comprising a single-stranded 3'-overhang; and j) detecting the cut PDNA using single-cell sequencing.

3. The method of claim 1, wherein the first and second antibodies bind to: (i) different targets on the same molecule, or (ii) different targets on different molecules.

4. The method of claim 1, wherein at least one of the first or second targets comprises a protein, a sugar, or a phosphate.

5. The method of claim 1, wherein at least one of the first or second targets is a cancer biomarker and is expressed on the surface of a cancer cell.

6. The method of claim 1, wherein at least one of the first or second targets is selected from the group consisting of CD274, CD16, CD56, CD4, CD8a, CD19, CD20, CD21, CD19, CD25, CD279, CD278, CD137, CD127, CD273, CD14, CD117, CD152, CD223, CD134, CD141, CD34, CD45, and CD3.

7. The method of claim 1, wherein the first and second AOT oligonucleotides comprise one or more barcode sequences.

8. The method of claim 1 further comprising providing at least one mask oligonucleotide in step (a), wherein the sequence of the mask oligonucleotide is complementary to at least one of the hybridization regions on the first or second oligonucleotide of the first or second AOT.

9. The method of claim 1, wherein step (f) further comprises providing single-cell sequencing data to a system, the system comprising:
  at least one processor that is programmed to:
    receive single-cell sequencing data comprising a barcodes file and a features file;
    generate FASTQ files from the single-cell sequencing data;
    define a plurality of search strings, wherein each search string in the plurality of search strings comprises at least two feature site sequences and at least one spacer of a defined length, wherein the at least two feature site sequences are associated with the first and second targets;
    determine a location of each search string in the plurality of search strings in the FASTQ files and unique identifiers of the determined location;
    cause the determined location and the unique identifiers of each search string in the plurality of search strings to be presented.

10. The method of claim 9, wherein a search string in the plurality of search strings is associated with a sequence of the PDNA.

11. The method of claim 9, wherein a search string in the plurality of search strings is associated with a segment of the sequence of the PDNA.

* * * * *

SEQUENCE LISTING

```
Sequence total quantity: 106
SEQ ID NO: 1            moltype = DNA  length = 15
FEATURE                 Location/Qualifiers
misc_feature            1..15
                        note = Exemplary antibody-oligo tag
source                  1..15
                        mol_type = other DNA
                        organism = synthetic construct
SEQUENCE: 1
gttgtccgac aatac                                                          15

SEQ ID NO: 2            moltype = DNA  length = 15
FEATURE                 Location/Qualifiers
misc_feature            1..15
                        note = Exemplary antibody-oligo tag
source                  1..15
                        mol_type = other DNA
                        organism = synthetic construct
SEQUENCE: 2
cgcgcaccca ttaaa                                                          15

SEQ ID NO: 3            moltype = DNA  length = 47
FEATURE                 Location/Qualifiers
misc_feature            1..47
                        note = Exemplary antibody-oligo tag
source                  1..47
                        mol_type = other DNA
```

```
                    organism = synthetic construct
SEQUENCE: 3
tattgacgat ccattgggat ggnnnnnnnn nntgcaccgt ctgcctt            47

SEQ ID NO: 4            moltype = DNA   length = 65
FEATURE                 Location/Qualifiers
misc_feature            1..65
                        note = Exemplary antibody-oligo tag
source                  1..65
                        mol_type = other DNA
                        organism = synthetic construct
SEQUENCE: 4
cagacggaan nnnnnnnntc cgccacgcgt cggnnnnnnn nnngacagag aatatgtgta   60
gaggc                                                              65

SEQ ID NO: 5            moltype = DNA   length = 103
FEATURE                 Location/Qualifiers
misc_feature            1..103
                        note = Exemplary product formed by hybridization of two
                         antibody-oligo tags
source                  1..103
                        mol_type = other DNA
                        organism = synthetic construct
SEQUENCE: 5
tattgacgat ccattgggat ggnnnnnnnn nntgcaccgt ctgccttnnn nnnnnnaggc   60
ggtgcgcagc cnnnnnnnnn nctgtctctt atacacatct ccg                    103

SEQ ID NO: 6            moltype = DNA   length = 103
FEATURE                 Location/Qualifiers
misc_feature            1..103
                        note = Exemplary product formed by hybridization of two
                         antibody-oligo tags
source                  1..103
                        mol_type = other DNA
                        organism = synthetic construct
SEQUENCE: 6
ataactgcta ggtaacccta ccnnnnnnnn nnacgtggca gacggaannn nnnnnntccg   60
ccacgcgtcg gnnnnnnnnn ngacagagaa tatgtgtaga ggc                    103

SEQ ID NO: 7            moltype = DNA   length = 155
FEATURE                 Location/Qualifiers
misc_feature            1..155
                        note = Exemplary product formed by hybridization of two
                         antibody-oligo tags with barcodes added for sequencing
source                  1..155
                        mol_type = other DNA
                        organism = synthetic construct
SEQUENCE: 7
ctacacgacg ctcttccgat ctnnnnnnnn nnnnnnnnnn nnnnnnnntt tcttatatgg   60
gatggnnnnn nnnntgcac cgtctgcctt gtctgccttn nnnnnnnnag gcggtgcgca    120
gccnnnnnnn nnnctgtctc ttatacacat ctccg                             155

SEQ ID NO: 8            moltype = DNA   length = 155
FEATURE                 Location/Qualifiers
misc_feature            1..155
                        note = Exemplary product formed by hybridization of two
                         antibody-oligo tags with barcodes added for sequencing
source                  1..155
                        mol_type = other DNA
                        organism = synthetic construct
SEQUENCE: 8
gatgtgctgc gagaaggcta gannnnnnnn nnnnnnnnnn nnnnnnnnaa agaatatacc   60
ctaccnnnnn nnnnacgtg gcagacggaa cagacggaan nnnnnnntc cgccacgcgt     120
cggnnnnnnn nnngacagag aatatgtgta gaggc                             155

SEQ ID NO: 9            moltype = DNA   length = 65
FEATURE                 Location/Qualifiers
misc_feature            1..65
                        note = Exemplary antibody-oligo tag
source                  1..65
                        mol_type = other DNA
                        organism = synthetic construct
SEQUENCE: 9
cagacggaan nnnnnnnnat caactgtacg gtannnnnnn nnngacagag aatatgtgta   60
gaggc                                                              65

SEQ ID NO: 10           moltype = DNA   length = 65
FEATURE                 Location/Qualifiers
misc_feature            1..65
```

```
                    note = Exemplary antibody-oligo tag
source              1..65
                    mol_type = other DNA
                    organism = synthetic construct
SEQUENCE: 10
cagacggaan nnnnnnnnct gcgcgcaaca gtannnnnnn nnngacagag aatatgtgta    60
gaggc                                                                65

SEQ ID NO: 11           moltype = DNA  length = 64
FEATURE                 Location/Qualifiers
misc_feature            1..64
                        note = Exemplary R1 sequencing read
source                  1..64
                        mol_type = other DNA
                        organism = synthetic construct
SEQUENCE: 11
ctacacgacg ctcttccgat ctnnnnnnnn nnnnnnnnnn nnnnnnnntt tcttatatrg    60
rgrg                                                                 64

SEQ ID NO: 12           moltype = DNA  length = 69
FEATURE                 Location/Qualifiers
misc_feature            1..69
                        note = Exemplary R2 sequencing read
source                  1..69
                        mol_type = other DNA
                        organism = synthetic construct
SEQUENCE: 12
aaagaatata cccnnnnnnn nnnnnnnnnn nnnnnnnnnn nnnnnnngac agagaatatg    60
tgtagaggc                                                            69

SEQ ID NO: 13           moltype = DNA  length = 15
FEATURE                 Location/Qualifiers
misc_feature            1..15
                        note = Exemplary feature sequence
source                  1..15
                        mol_type = other DNA
                        organism = synthetic construct
SEQUENCE: 13
gttgtccgac aatac                                                     15

SEQ ID NO: 14           moltype = DNA  length = 15
FEATURE                 Location/Qualifiers
misc_feature            1..15
                        note = Exemplary feature sequence
source                  1..15
                        mol_type = other DNA
                        organism = synthetic construct
SEQUENCE: 14
aagttcactc tttgc                                                     15

SEQ ID NO: 15           moltype = DNA  length = 15
FEATURE                 Location/Qualifiers
misc_feature            1..15
                        note = Exemplary feature sequence
source                  1..15
                        mol_type = other DNA
                        organism = synthetic construct
SEQUENCE: 15
ttcgccgcat tgagt                                                     15

SEQ ID NO: 16           moltype = DNA  length = 15
FEATURE                 Location/Qualifiers
misc_feature            1..15
                        note = Exemplary feature sequence
source                  1..15
                        mol_type = other DNA
                        organism = synthetic construct
SEQUENCE: 16
tgttcccgct caact                                                     15

SEQ ID NO: 17           moltype = DNA  length = 15
FEATURE                 Location/Qualifiers
misc_feature            1..15
                        note = Exemplary feature sequence
source                  1..15
                        mol_type = other DNA
                        organism = synthetic construct
SEQUENCE: 17
gctgcgcttt ccatt                                                     15
```

| SEQ ID NO: 18   | moltype = DNA  length = 15          |    |
|---|---|---|
| FEATURE         | Location/Qualifiers                 |    |
| misc_feature    | 1..15                               |    |
|                 | note = Exemplary feature sequence   |    |
| source          | 1..15                               |    |
|                 | mol_type = other DNA                |    |
|                 | organism = synthetic construct      |    |
| SEQUENCE: 18    |                                     |    |
| ctgggcaatt actcg |                                    | 15 |

| SEQ ID NO: 19   | moltype = DNA  length = 15          |    |
|---|---|---|
| FEATURE         | Location/Qualifiers                 |    |
| misc_feature    | 1..15                               |    |
|                 | note = Exemplary feature sequence   |    |
| source          | 1..15                               |    |
|                 | mol_type = other DNA                |    |
|                 | organism = synthetic construct      |    |
| SEQUENCE: 19    |                                     |    |
| ttctgggtcc ctaga |                                    | 15 |

| SEQ ID NO: 20   | moltype = DNA  length = 15          |    |
|---|---|---|
| FEATURE         | Location/Qualifiers                 |    |
| misc_feature    | 1..15                               |    |
|                 | note = Exemplary feature sequence   |    |
| source          | 1..15                               |    |
|                 | mol_type = other DNA                |    |
|                 | organism = synthetic construct      |    |
| SEQUENCE: 20    |                                     |    |
| aacctagtag ttcgg |                                    | 15 |

| SEQ ID NO: 21   | moltype = DNA  length = 15          |    |
|---|---|---|
| FEATURE         | Location/Qualifiers                 |    |
| misc_feature    | 1..15                               |    |
|                 | note = Exemplary feature sequence   |    |
| source          | 1..15                               |    |
|                 | mol_type = other DNA                |    |
|                 | organism = synthetic construct      |    |
| SEQUENCE: 21    |                                     |    |
| cgagtaattg cccag |                                    | 15 |

| SEQ ID NO: 22   | moltype = DNA  length = 15          |    |
|---|---|---|
| FEATURE         | Location/Qualifiers                 |    |
| misc_feature    | 1..15                               |    |
|                 | note = Exemplary feature sequence   |    |
| source          | 1..15                               |    |
|                 | mol_type = other DNA                |    |
|                 | organism = synthetic construct      |    |
| SEQUENCE: 22    |                                     |    |
| ccgaactact aggtt |                                    | 15 |

| SEQ ID NO: 23   | moltype = DNA  length = 15          |    |
|---|---|---|
| FEATURE         | Location/Qualifiers                 |    |
| misc_feature    | 1..15                               |    |
|                 | note = Exemplary feature sequence   |    |
| source          | 1..15                               |    |
|                 | mol_type = other DNA                |    |
|                 | organism = synthetic construct      |    |
| SEQUENCE: 23    |                                     |    |
| cgagtaattg cccag |                                    | 15 |

| SEQ ID NO: 24   | moltype = DNA  length = 15          |    |
|---|---|---|
| FEATURE         | Location/Qualifiers                 |    |
| misc_feature    | 1..15                               |    |
|                 | note = Exemplary feature sequence   |    |
| source          | 1..15                               |    |
|                 | mol_type = other DNA                |    |
|                 | organism = synthetic construct      |    |
| SEQUENCE: 24    |                                     |    |
| ccgaactact aggtt |                                    | 15 |

| SEQ ID NO: 25   | moltype = DNA  length = 15          |    |
|---|---|---|
| FEATURE         | Location/Qualifiers                 |    |
| misc_feature    | 1..15                               |    |
|                 | note = Exemplary feature sequence   |    |
| source          | 1..15                               |    |
|                 | mol_type = other DNA                |    |
|                 | organism = synthetic construct      |    |
| SEQUENCE: 25    |                                     |    |

```
cgagtaattg cccag                                                         15

SEQ ID NO: 26            moltype = DNA   length = 15
FEATURE                  Location/Qualifiers
misc_feature             1..15
                         note = Exemplary feature sequence
source                   1..15
                         mol_type = other DNA
                         organism = synthetic construct
SEQUENCE: 26
ccgaactact aggtt                                                         15

SEQ ID NO: 27            moltype = DNA   length = 15
FEATURE                  Location/Qualifiers
misc_feature             1..15
                         note = Exemplary feature sequence
source                   1..15
                         mol_type = other DNA
                         organism = synthetic construct
SEQUENCE: 27
tttgtcctgt acgcc                                                         15

SEQ ID NO: 28            moltype = DNA   length = 15
FEATURE                  Location/Qualifiers
misc_feature             1..15
                         note = Exemplary feature sequence
source                   1..15
                         mol_type = other DNA
                         organism = synthetic construct
SEQUENCE: 28
acagcgccgt attta                                                         15

SEQ ID NO: 29            moltype = DNA   length = 15
FEATURE                  Location/Qualifiers
misc_feature             1..15
                         note = Exemplary feature sequence
source                   1..15
                         mol_type = other DNA
                         organism = synthetic construct
SEQUENCE: 29
cgcgcaccca ttaaa                                                         15

SEQ ID NO: 30            moltype = DNA   length = 15
FEATURE                  Location/Qualifiers
misc_feature             1..15
                         note = Exemplary feature sequence
source                   1..15
                         mol_type = other DNA
                         organism = synthetic construct
SEQUENCE: 30
cagtaagttc gggac                                                         15

SEQ ID NO: 31            moltype = DNA   length = 15
FEATURE                  Location/Qualifiers
misc_feature             1..15
                         note = Exemplary feature sequence
source                   1..15
                         mol_type = other DNA
                         organism = synthetic construct
SEQUENCE: 31
gtgtgttgtc ctatg                                                         15

SEQ ID NO: 32            moltype = DNA   length = 15
FEATURE                  Location/Qualifiers
misc_feature             1..15
                         note = Exemplary feature sequence
source                   1..15
                         mol_type = other DNA
                         organism = synthetic construct
SEQUENCE: 32
tcaacgcttg gctag                                                         15

SEQ ID NO: 33            moltype = DNA   length = 15
FEATURE                  Location/Qualifiers
misc_feature             1..15
                         note = Exemplary feature sequence
source                   1..15
                         mol_type = other DNA
                         organism = synthetic construct
```

```
SEQUENCE: 33
caatcagacc tatga                                                     15

SEQ ID NO: 34           moltype = DNA   length = 15
FEATURE                 Location/Qualifiers
misc_feature            1..15
                        note = Exemplary feature sequence
source                  1..15
                        mol_type = other DNA
                        organism = synthetic construct
SEQUENCE: 34
agactaatag ctgac                                                     15

SEQ ID NO: 35           moltype = DNA   length = 15
FEATURE                 Location/Qualifiers
misc_feature            1..15
                        note = Exemplary feature sequence
source                  1..15
                        mol_type = other DNA
                        organism = synthetic construct
SEQUENCE: 35
atggttcacg taatc                                                     15

SEQ ID NO: 36           moltype = DNA   length = 15
FEATURE                 Location/Qualifiers
misc_feature            1..15
                        note = Exemplary feature sequence
source                  1..15
                        mol_type = other DNA
                        organism = synthetic construct
SEQUENCE: 36
catttgtctg ccggt                                                     15

SEQ ID NO: 37           moltype = DNA   length = 15
FEATURE                 Location/Qualifiers
misc_feature            1..15
                        note = Exemplary feature sequence
source                  1..15
                        mol_type = other DNA
                        organism = synthetic construct
SEQUENCE: 37
aacccaccgt tgtta                                                     15

SEQ ID NO: 38           moltype = DNA   length = 15
FEATURE                 Location/Qualifiers
misc_feature            1..15
                        note = Exemplary feature sequence
source                  1..15
                        mol_type = other DNA
                        organism = synthetic construct
SEQUENCE: 38
ggataaccgc gcttt                                                     15

SEQ ID NO: 39           moltype = DNA   length = 15
FEATURE                 Location/Qualifiers
misc_feature            1..15
                        note = Exemplary feature sequence
source                  1..15
                        mol_type = other DNA
                        organism = synthetic construct
SEQUENCE: 39
gcagaaatct ccctt                                                     15

SEQ ID NO: 40           moltype = DNA   length = 15
FEATURE                 Location/Qualifiers
misc_feature            1..15
                        note = Exemplary feature sequence
source                  1..15
                        mol_type = other DNA
                        organism = synthetic construct
SEQUENCE: 40
tgcaattacc cggat                                                     15

SEQ ID NO: 41           moltype = DNA   length = 15
FEATURE                 Location/Qualifiers
misc_feature            1..15
                        note = Exemplary feature sequence
source                  1..15
                        mol_type = other DNA
```

```
                           organism = synthetic construct
SEQUENCE: 41
ctcattgtaa ctcct                                                     15

SEQ ID NO: 42              moltype = DNA   length = 154
FEATURE                    Location/Qualifiers
misc_feature               1..154
                           note = Exemplary search string
source                     1..154
                           mol_type = other DNA
                           organism = synthetic construct
SEQUENCE: 42
cggagatgtg tataagagac agnnnnnnnn nncgagtaat tgcccagnnn nnnnnnnnn      60
nnnnnnnnnn nnnnnnnnnn nnnnnnnnnn nnnnnnnnnn nnnnnnnnnn nnnnnnccg     120
aactactagg ttnnnnnnnn ncccatataa gaaa                                154

SEQ ID NO: 43              moltype = DNA   length = 132
FEATURE                    Location/Qualifiers
misc_feature               1..132
                           note = Exemplary search string
source                     1..132
                           mol_type = other DNA
                           organism = synthetic construct
SEQUENCE: 43
nnnnnnnnnn cgagtaattg cccagnnnnn nnnnnnnnnn nnnnnnnnnn nnnnnnnnnn      60
nnnnnnnnnn nnnnnnnnnn nnnnnnnnnn nnnnccgaa ctactaggtt nnnnnnnnnc     120
ccatataaga aa                                                        132

SEQ ID NO: 44              moltype = DNA   length = 91
FEATURE                    Location/Qualifiers
misc_feature               1..91
                           note = Exemplary combined R1R2 paired-end read
source                     1..91
                           mol_type = other DNA
                           organism = synthetic construct
SEQUENCE: 44
ttaattgtcc ctgggcaatt actcgcttgt gagacccata taagaaagaa aagcaagaca     60
tgccctgggc ataagatcgg aagagcgtcg t                                    91

SEQ ID NO: 45              moltype = DNA   length = 91
FEATURE                    Location/Qualifiers
misc_feature               1..91
                           note = Exemplary combined R1R2 paired-end read
source                     1..91
                           mol_type = other DNA
                           organism = synthetic construct
SEQUENCE: 45
cggttcagaa ctgggcaatt actcgtaaac actccccata taagaaagcg tgggcagaga     60
gtacctaacg cgaagatcgg aagagcgtcg t                                    91

SEQ ID NO: 46              moltype = DNA   length = 91
FEATURE                    Location/Qualifiers
misc_feature               1..91
                           note = Exemplary combined R1R2 paired-end read
source                     1..91
                           mol_type = other DNA
                           organism = synthetic construct
SEQUENCE: 46
ctacagtctc ctgggcaatt actcgaatag tgcacccata taagaaaata ccgacatttg     60
tacgaagta gatagatcgg aagagcgtcg t                                     91

SEQ ID NO: 47              moltype = DNA   length = 91
FEATURE                    Location/Qualifiers
misc_feature               1..91
                           note = Exemplary combined R1R2 paired-end read
source                     1..91
                           mol_type = other DNA
                           organism = synthetic construct
SEQUENCE: 47
cattaattta ctgggcaatt actcgtctgt ctttcccata taagaaataa aatcgagact     60
acttacgagg aaaagatcgg aagagcgtcg t                                    91

SEQ ID NO: 48              moltype = DNA   length = 91
FEATURE                    Location/Qualifiers
misc_feature               1..91
                           note = Exemplary combined R1R2 paired-end read
source                     1..91
                           mol_type = other DNA
                           organism = synthetic construct
```

```
SEQUENCE: 48
tcaattcaat ctgggcaatt actcgcaaca aggtcccata taagaaagtg ataattttca    60
tcgagattcg gatagatcgg aagagcgtcg t                                   91

SEQ ID NO: 49           moltype = DNA   length = 91
FEATURE                 Location/Qualifiers
misc_feature            1..91
                        note = Exemplary combined R1R2 paired-end read
source                  1..91
                        mol_type = other DNA
                        organism = synthetic construct
SEQUENCE: 49
gctaggcgcc ctgggcaatt actcgcaaca ctaccccata taagaaactg tcaaagttct    60
ctgtctgacc gctagatcgg aagagcgtcg t                                   91

SEQ ID NO: 50           moltype = DNA   length = 91
FEATURE                 Location/Qualifiers
misc_feature            1..91
                        note = Exemplary combined R1R2 paired-end read
source                  1..91
                        mol_type = other DNA
                        organism = synthetic construct
SEQUENCE: 50
catagattgt ctgggcaatt actcgtaaca ggccccatt aagaaagaag tgcaatacaa     60
tcgacggtgg atagatcgga agagcgtcgt g                                   91

SEQ ID NO: 51           moltype = DNA   length = 90
FEATURE                 Location/Qualifiers
misc_feature            1..90
                        note = Exemplary combined R1R2 paired-end read
source                  1..90
                        mol_type = other DNA
                        organism = synthetic construct
SEQUENCE: 51
taatttgatc ctgggcaatt actcggaagt aggccccata taagaaagta caaactggcg    60
ctgaacaccg cacagatcgg aagagcgtct                                     90

SEQ ID NO: 52           moltype = DNA   length = 91
FEATURE                 Location/Qualifiers
misc_feature            1..91
                        note = Exemplary combined R1R2 paired-end read
source                  1..91
                        mol_type = other DNA
                        organism = synthetic construct
SEQUENCE: 52
atcctataca ctgggcaatt actcggctgg caagcccata taagaaaata agcgtgtggg    60
ctagctaaat gacagatcgg aagagcgtcg t                                   91

SEQ ID NO: 53           moltype = DNA   length = 91
FEATURE                 Location/Qualifiers
misc_feature            1..91
                        note = Exemplary combined R1R2 paired-end read
source                  1..91
                        mol_type = other DNA
                        organism = synthetic construct
SEQUENCE: 53
cgaatgtggg ctgggcaatt actcgttaac gcaacccata taagaaacta ctcgtcgaag    60
tctgtgacgc ttaagatcgg aagagcgtcg t                                   91

SEQ ID NO: 54           moltype = DNA   length = 15
FEATURE                 Location/Qualifiers
misc_feature            1..15
                        note = Portion of exemplary R2 read
source                  1..15
                        mol_type = other DNA
                        organism = synthetic construct
SEQUENCE: 54
cgagtaattg cccag                                                     15

SEQ ID NO: 55           moltype = DNA   length = 15
FEATURE                 Location/Qualifiers
misc_feature            1..15
                        note = Portion of exemplary R2 read
source                  1..15
                        mol_type = other DNA
                        organism = synthetic construct
SEQUENCE: 55
ccgaactact aggtt                                                     15
```

| | | |
|---|---|---|
| SEQ ID NO: 56 | moltype = DNA   length = 14 | |
| FEATURE | Location/Qualifiers | |
| misc_feature | 1..14 | |
| | note = Portion of exemplary R2 read | |
| source | 1..14 | |
| | mol_type = other DNA | |
| | organism = synthetic construct | |

SEQUENCE: 56
cccatataag aaaa                                                          14

| | | |
|---|---|---|
| SEQ ID NO: 57 | moltype = DNA   length = 134 | |
| FEATURE | Location/Qualifiers | |
| misc_feature | 1..134 | |
| | note = Exemplary R2 read | |
| source | 1..134 | |
| | mol_type = other DNA | |
| | organism = synthetic construct | |

SEQUENCE: 57
taccactttg cgagtaattg cccaggtacc atttgctacc gacccatgga ataggatatc         60
cagactaata ctggcgctaa gttaacaaat ccggtccgaa ctactaggtt ctccatgatc        120
ccatataaga aaac                                                         134

| | | |
|---|---|---|
| SEQ ID NO: 58 | moltype = DNA   length = 134 | |
| FEATURE | Location/Qualifiers | |
| misc_feature | 1..134 | |
| | note = Exemplary R2 read | |
| source | 1..134 | |
| | mol_type = other DNA | |
| | organism = synthetic construct | |

SEQUENCE: 58
gtaatccgtt cgagtaattg cccagaccag gcccagtttc ccattctccg tcccgaacta         60
ctaggttccc gggtccccca tataagaaaa agaaaagtcc tctcatcttt gtgacagatc        120
ggaagagcgt cgtg                                                         134

| | | |
|---|---|---|
| SEQ ID NO: 59 | moltype = DNA   length = 134 | |
| FEATURE | Location/Qualifiers | |
| misc_feature | 1..134 | |
| | note = Exemplary R2 read | |
| source | 1..134 | |
| | mol_type = other DNA | |
| | organism = synthetic construct | |

SEQUENCE: 59
atttcagaac cgagtaattg cccagaagcc attcacatcg tcaaatgtcc caccgaacta         60
ctaggttcaa cccaggccca tataagaaag agtagactcc ttgcagctta gcatcagatc        120
ggaagagcgt cgtg                                                         134

| | | |
|---|---|---|
| SEQ ID NO: 60 | moltype = DNA   length = 134 | |
| FEATURE | Location/Qualifiers | |
| misc_feature | 1..134 | |
| | note = Exemplary R2 read | |
| source | 1..134 | |
| | mol_type = other DNA | |
| | organism = synthetic construct | |

SEQUENCE: 60
ccactgtaag cgagtaattg cccaggtctc cgctccgmac tactaggttc ccaaggcccc         60
catataagaa aagacggata agctagagga acgtgttaga tcggaagagc gtcgtggagg        120
gaaatagtgt agaa                                                         134

| | | |
|---|---|---|
| SEQ ID NO: 61 | moltype = DNA   length = 134 | |
| FEATURE | Location/Qualifiers | |
| misc_feature | 1..134 | |
| | note = Exemplary R2 read | |
| source | 1..134 | |
| | mol_type = other DNA | |
| | organism = synthetic construct | |

SEQUENCE: 61
cggccctacc cgagtaattg cccagtgtcc taagagcccc atagtttaga ttccgattgc         60
gttctccact ggccttgaga tcggaagagc gtcgtgtagg gaaagagtgt agatctcggt        120
ggtcgccgta tcat                                                         134

| | | |
|---|---|---|
| SEQ ID NO: 62 | moltype = DNA   length = 134 | |
| FEATURE | Location/Qualifiers | |
| misc_feature | 1..134 | |
| | note = Exemplary R2 read | |
| source | 1..134 | |
| | mol_type = other DNA | |
| | organism = synthetic construct | |

SEQUENCE: 62
ctcataggcc cgagtaattg cccagcgttt gtaacaacat taagcacttc tgccgaacta         60

```
ctaggttcaa tcccagccca tataagaaag ccgaagagac agtctgctcc actctagatc    120
ggaagagcgt cgtg                                                      134

SEQ ID NO: 63          moltype = DNA   length = 134
FEATURE                Location/Qualifiers
misc_feature           1..134
                       note = Exemplary R2 read
source                 1..134
                       mol_type = other DNA
                       organism = synthetic construct
SEQUENCE: 63
caaatgttca cgagtaattg cccagattca acgcgttcca aagcgagacc gaggcatgac    60
aggtagttat tgtgcaccta cgtctttatg ttcacccgaa ctactaggtt ctttgtcgac    120
ccatataaga aact                                                      134

SEQ ID NO: 64          moltype = DNA   length = 131
FEATURE                Location/Qualifiers
misc_feature           1..131
                       note = Exemplary R2 read
source                 1..131
                       mol_type = other DNA
                       organism = synthetic construct
SEQUENCE: 64
attcagggcc cgagtaattg cccactgtcc ggttccgmct actaggttca tgccagcccc    60
atataagaaa ttgactttca gacggtgctt ggtctaagat cgagagcgtc gtgtagggaa    120
agagtgtaga a                                                         131

SEQ ID NO: 65          moltype = DNA   length = 134
FEATURE                Location/Qualifiers
misc_feature           1..134
                       note = Exemplary R2 read
source                 1..134
                       mol_type = other DNA
                       organism = synthetic construct
SEQUENCE: 65
tctaatgccg cgagtaattg cccagcttgc aaacccgmac tactaggttg tagagcttcc    60
catataagaa atacgctagc ttatagctct ttggtgtaga tctcaataga ctccttaaca    120
taaaaaaaaa aaaa                                                      134

SEQ ID NO: 66          moltype = DNA   length = 133
FEATURE                Location/Qualifiers
misc_feature           1..133
                       note = Exemplary R2 read
source                 1..133
                       mol_type = other DNA
                       organism = synthetic construct
SEQUENCE: 66
atagcataag cgagtaattg cccagccaat ccttccgaac tactaggttt tccccccccc    60
atataagaaa tctgtatgtg ttgcgcggat cccactagat cggaagagcg tcgtgtaggg    120
aaagagtgta gat                                                       133

SEQ ID NO: 67          moltype = DNA   length = 134
FEATURE                Location/Qualifiers
misc_feature           1..134
                       note = Exemplary R2 read
source                 1..134
                       mol_type = other DNA
                       organism = synthetic construct
SEQUENCE: 67
gcctcgaatc cgagtaattg cccagcgtag gtattgaccc tactcatcga catccaataa    60
atggtacacc ggagtcccca ctcttctccc catataagaa actggaacac tcctcgttac    120
cttgtgaaga tcgg                                                      134

SEQ ID NO: 68          moltype = DNA   length = 134
FEATURE                Location/Qualifiers
misc_feature           1..134
                       note = Exemplary R2 read
source                 1..134
                       mol_type = other DNA
                       organism = synthetic construct
SEQUENCE: 68
tctgtagtcc cgagtaattg cccagcaccc ttccccgmac tactaggttc gtttgcttcc    60
catataagaa aagatggtat gtgcatgtga atcctgaaga tcggaagagc gtcgtgtagg    120
gaaagagtgt agat                                                      134

SEQ ID NO: 69          moltype = DNA   length = 134
FEATURE                Location/Qualifiers
misc_feature           1..134
                       note = Exemplary R2 read
```

```
source                  1..134
                        mol_type = other DNA
                        organism = synthetic construct
SEQUENCE: 69
tagccttcca cgagtaattg cccaggtttg tggtattaga ataacgcgta ctccgaacta    60
ctaggttacg aattctccca tataagaaag gtccgtgaag cgtatatggt agcaagatcg   120
gaagagcgtc gtgt                                                    134

SEQ ID NO: 70           moltype = DNA   length = 134
FEATURE                 Location/Qualifiers
misc_feature            1..134
                        note = Exemplary R2 read
source                  1..134
                        mol_type = other DNA
                        organism = synthetic construct
SEQUENCE: 70
tgtaatccac cgagtaattg cccagtcctt tgagccgaac tactaggttg attttcgccc    60
catataagaa aaaacgaaga attctggctg gaagtcgaga tcggaagagc gtcgtgtatg   120
gaaagagtgt agat                                                    134

SEQ ID NO: 71           moltype = DNA   length = 134
FEATURE                 Location/Qualifiers
misc_feature            1..134
                        note = Exemplary R2 read
source                  1..134
                        mol_type = other DNA
                        organism = synthetic construct
SEQUENCE: 71
tgtatgcgac cgagtaattg cccaggcgct atccccgaac tactaggtct gcggcaggcc    60
catataagaa acaattccag tcgcaatgag cgtccaagat cggaagagcg tcgtgtaggg   120
aaagagtgta tata                                                    134

SEQ ID NO: 72           moltype = DNA   length = 134
FEATURE                 Location/Qualifiers
misc_feature            1..134
                        note = Exemplary R2 read
source                  1..134
                        mol_type = other DNA
                        organism = synthetic construct
SEQUENCE: 72
aaaccggagc cgagtaattg cccagcgtga cgtacaaaaa agcgcttcac tgataacaaa    60
tacatccact taaatgactt ccaataaatc aacgaccgaa ctactaggtt gactacagac   120
ccatataaga aagc                                                    134

SEQ ID NO: 73           moltype = DNA   length = 134
FEATURE                 Location/Qualifiers
misc_feature            1..134
                        note = Exemplary R2 read
source                  1..134
                        mol_type = other DNA
                        organism = synthetic construct
SEQUENCE: 73
cggccgtttg cgagtaattg cccagtccac gactccgaac tactaggttc tgcttacgcc    60
catataacaa agcggagaca gggttaactg tctgctcaga tcggaagagc gtcgtggtgg   120
gaaagagtgt tgat                                                    134

SEQ ID NO: 74           moltype = DNA   length = 133
FEATURE                 Location/Qualifiers
misc_feature            1..133
                        note = Exemplary R2 read
source                  1..133
                        mol_type = other DNA
                        organism = synthetic construct
SEQUENCE: 74
tgtccggtca cgagtaattg cccagatcca ctaaccgaac tactaggttg tgaccctccc    60
catataagaa aagcaagaga gtgggctcga atgatcagat cggaagagcg tcgtgtaggg   120
aaagagtgta gct                                                     133

SEQ ID NO: 75           moltype = DNA   length = 134
FEATURE                 Location/Qualifiers
misc_feature            1..134
                        note = Exemplary R2 read
source                  1..134
                        mol_type = other DNA
                        organism = synthetic construct
SEQUENCE: 75
gcaataaaat cgagtaattg cccaggtact gagaatagaa acccaggtca ttccgaacta    60
ctaggttgtt taagtcccca tataagaaat aaaattcgag aaacgcgata atgagagatc   120
ggaagagcgt cgtg                                                    134
```

```
SEQ ID NO: 76            moltype = DNA   length = 134
FEATURE                  Location/Qualifiers
misc_feature             1..134
                         note = Exemplary R2 read
source                   1..134
                         mol_type = other DNA
                         organism = synthetic construct
SEQUENCE: 76
gcatctagta cgagtaattg cccagcactg gccccgttaa gtaacccctc aaacatctcc   60
aacacagtcc atctgctcca tacaaagagt tatatccgaa ctatttggcg atttggcaag  120
atcggaagag cgtc                                                    134

SEQ ID NO: 77            moltype = DNA   length = 131
FEATURE                  Location/Qualifiers
misc_feature             1..131
                         note = Exemplary R2 read
source                   1..131
                         mol_type = other DNA
                         organism = synthetic construct
SEQUENCE: 77
gtcataaata cgagtaattg cccagacaaa tcgtgctcac ccacgctcga ccccgactac   60
gctacttcgt gaagatcgga agagcgtcgt gtagggamag agtgtagatc tcggtgtcgc  120
cgtatcatta a                                                       131

SEQ ID NO: 78            moltype = DNA   length = 134
FEATURE                  Location/Qualifiers
misc_feature             1..134
                         note = Exemplary R2 read
source                   1..134
                         mol_type = other DNA
                         organism = synthetic construct
SEQUENCE: 78
tcacagttcc cgagtaattg cccagtcact acacgagttg gtcataaaaa cgttttgaag   60
cctggtctcc tcagattaca ttggatcgtc atcatccgaa ctactaggtt taacatgcat  120
ccatataaga aatc                                                    134

SEQ ID NO: 79            moltype = DNA   length = 134
FEATURE                  Location/Qualifiers
misc_feature             1..134
                         note = Exemplary R2 read
source                   1..134
                         mol_type = other DNA
                         organism = synthetic construct
SEQUENCE: 79
gaacccagcg cgagtaattg cccagcccag cttcaaaatc tttcgtcggt atccgaacta   60
ctaggtttcc gcagtaccca tataagaaaa ccaaggaaac gatgcgactc gtgatagatc  120
ggaagagcgt cgtg                                                    134

SEQ ID NO: 80            moltype = DNA   length = 134
FEATURE                  Location/Qualifiers
misc_feature             1..134
                         note = Exemplary R2 read
source                   1..134
                         mol_type = other DNA
                         organism = synthetic construct
SEQUENCE: 80
gtcgagatag aacctagtag ttcggcaggt ttagcccatg cccagtctcc acccaattcc   60
gtcaagcctc gacccaagca aatgtatgac ttccacccac ttataagacc gggtcccgaa  120
ctactaggtt attt                                                    134

SEQ ID NO: 81            moltype = DNA   length = 132
FEATURE                  Location/Qualifiers
misc_feature             1..132
                         note = Exemplary R2 read
source                   1..132
                         mol_type = other DNA
                         organism = synthetic construct
SEQUENCE: 81
cgtgacccgc cgagtattgc ccagcgttac gtcgtccggc gacagcagta cccgactact   60
aggtttctct tcgtcccata taagaaaagc ggctccgtcc atccgacgcg atcagatcgg  120
aagagcgtcg tg                                                      132

SEQ ID NO: 82            moltype = DNA   length = 134
FEATURE                  Location/Qualifiers
misc_feature             1..134
                         note = Exemplary R2 read
source                   1..134
                         mol_type = other DNA
```

```
                        organism = synthetic construct
SEQUENCE: 82
tgagattctg cgagtaattg cccagctacc taatccgaac tactaggttt gagctctgcc    60
catataagaa agcgcactgg cggacacgct tcgctctaga tcggaagagc gtcgtgtatg   120
gaaagagtgt agaa                                                    134

SEQ ID NO: 83           moltype = DNA   length = 134
FEATURE                 Location/Qualifiers
misc_feature            1..134
                        note = Exemplary R2 read
source                  1..134
                        mol_type = other DNA
                        organism = synthetic construct
SEQUENCE: 83
gatggtttga cgagtaattg cccagtacct ctgtccgccc cgctagtata tcccgaacta    60
ctaggtttga tctgtcccca tataagaaaa atcattccat cgcgttacag tagatagatc   120
ggaagagcgt cgtg                                                    134

SEQ ID NO: 84           moltype = DNA   length = 132
FEATURE                 Location/Qualifiers
misc_feature            1..132
                        note = Exemplary R2 read
source                  1..132
                        mol_type = other DNA
                        organism = synthetic construct
SEQUENCE: 84
gacatgccaa cgagtaattg cccagtcgaa tagataaatc gttgcattta cacttaccga    60
tccatgcctt caccactata aagtattata gaccaccgaa ctactaggtt ctaactgacc   120
catataagaa aa                                                      132

SEQ ID NO: 85           moltype = DNA   length = 134
FEATURE                 Location/Qualifiers
misc_feature            1..134
                        note = Exemplary R2 read
source                  1..134
                        mol_type = other DNA
                        organism = synthetic construct
SEQUENCE: 85
gatacctgaa cgagtaattg cccagggtat ctaaccgmac tactaggttc cgcatacacc    60
catataagaa atctattcga ggcgccaatg cttattcaga tcggaagagc gtcgtgtagg   120
gaaagagtgt agat                                                    134

SEQ ID NO: 86           moltype = DNA   length = 134
FEATURE                 Location/Qualifiers
misc_feature            1..134
                        note = Exemplary R2 read
source                  1..134
                        mol_type = other DNA
                        organism = synthetic construct
SEQUENCE: 86
ggcgtcgagt cgagtaattg cccagtcgcc actctataag aggttagaac ttctgtctcc    60
cggttgcgtc tgatcgcata gatcggaaga gcgtcgtgta gggaaagagt gtagatctcg   120
gtggtcgccg tatc                                                    134

SEQ ID NO: 87           moltype = DNA   length = 134
FEATURE                 Location/Qualifiers
misc_feature            1..134
                        note = Exemplary R2 read
source                  1..134
                        mol_type = other DNA
                        organism = synthetic construct
SEQUENCE: 87
gtttgccatc cgagtaattg cccagccaaa atatccgaac tactaggttc acgctgcccc    60
catataagaa actgagactg tggtacagga gtgtccgaga tcggaagagc gtcgtgtagg   120
gaaagagtgt agat                                                    134

SEQ ID NO: 88           moltype = DNA   length = 134
FEATURE                 Location/Qualifiers
misc_feature            1..134
                        note = Exemplary R2 read
source                  1..134
                        mol_type = other DNA
                        organism = synthetic construct
SEQUENCE: 88
aagatgttaa cgagtaattg cccaggtcca tgtcgaatta caaatctgct tcccgaacta    60
ctaggttctc tcacatccca tataagaaag gccggtgatg gcaatttgag ccaagagatc   120
ggaagagcgt cgtg                                                    134

SEQ ID NO: 89           moltype = DNA   length = 134
```

| FEATURE | Location/Qualifiers |
|---|---|
| misc_feature | 1..134 |
| | note = Exemplary R2 read |
| source | 1..134 |
| | mol_type = other DNA |
| | organism = synthetic construct |

SEQUENCE: 89

```
ggagctgtcc cgagtaattg cccagtccgc acatatatat cataaaccct caccgaacta   60
ctaggttcaa ggctgaccca tataagaaaa gtcgatgtac caaggcactt gtgacagatc   120
ggaagagcgt cgtg                                                     134
```

| SEQ ID NO: 90 | moltype = DNA  length = 134 |
|---|---|
| FEATURE | Location/Qualifiers |
| misc_feature | 1..134 |
| | note = Exemplary R2 read |
| source | 1..134 |
| | mol_type = other DNA |
| | organism = synthetic construct |

SEQUENCE: 90

```
cgcttaatgc cgagtaattg cccagtaagg tattctagca ccccactcac caaaatctca   60
atgttacacg accctctgct agcgaacact cgtacccgaa ctactaggtt ggcgtctctc   120
ccatataaga aaag                                                     134
```

| SEQ ID NO: 91 | moltype = DNA  length = 134 |
|---|---|
| FEATURE | Location/Qualifiers |
| misc_feature | 1..134 |
| | note = Exemplary R2 read |
| source | 1..134 |
| | mol_type = other DNA |
| | organism = synthetic construct |

SEQUENCE: 91

```
tagctacggt cgagtaattg cccagacata actgccgaac tactaggttc atgggcggac   60
ccatataaga aaacaagag agatgtcgcc ttagggcaag atcggaagag cgtcgtgtac    120
gcaaagactg taga                                                     134
```

| SEQ ID NO: 92 | moltype = DNA  length = 134 |
|---|---|
| FEATURE | Location/Qualifiers |
| misc_feature | 1..134 |
| | note = Exemplary R2 read |
| source | 1..134 |
| | mol_type = other DNA |
| | organism = synthetic construct |

SEQUENCE: 92

```
atgcgtcccg cgagtaattg cccagatgac catttccctt ggacagtagc ccccgaacta   60
ctaggttcgg gttcgcccca tataagaaag gtaattctgg cttgcactgt atgggagatc   120
ggaagagcgt cgtg                                                     134
```

| SEQ ID NO: 93 | moltype = DNA  length = 133 |
|---|---|
| FEATURE | Location/Qualifiers |
| misc_feature | 1..133 |
| | note = Exemplary R2 read |
| source | 1..133 |
| | mol_type = other DNA |
| | organism = synthetic construct |

SEQUENCE: 93

```
aattagcgac cgagtaattg cccagatggc cattccgmac tactaggttg actgatcgcc   60
catataagaa agtcggggtc agcggtaaga acttgacaga tcggaagagc gtcgtgtagc   120
gaatattgta gat                                                      133
```

| SEQ ID NO: 94 | moltype = DNA  length = 134 |
|---|---|
| FEATURE | Location/Qualifiers |
| misc_feature | 1..134 |
| | note = Exemplary R2 read |
| source | 1..134 |
| | mol_type = other DNA |
| | organism = synthetic construct |

SEQUENCE: 94

```
gacataccc cgagtaattg cccagcttac tagataggcc ttctatggcg ggccgaacta    60
ctaggttgtt atccctccca tataagaaac gtaagtgact ggattcgatc cagcgagatc   120
ggaagagcgt cgtg                                                     134
```

| SEQ ID NO: 95 | moltype = DNA  length = 134 |
|---|---|
| FEATURE | Location/Qualifiers |
| misc_feature | 1..134 |
| | note = Exemplary R2 read |
| source | 1..134 |
| | mol_type = other DNA |
| | organism = synthetic construct |

SEQUENCE: 95

```
gcacgcatta cgagtaattg cccaggcctt acacccgaac tactaggttc ggacaatgcc    60
catataagaa aggaaaacac atgtcgaatg gaatatgaga tcggaagagc gtcgtggagg   120
gaaagagtgt agat                                                    134

SEQ ID NO: 96            moltype = DNA  length = 134
FEATURE                  Location/Qualifiers
misc_feature             1..134
                         note = Exemplary R2 read
source                   1..134
                         mol_type = other DNA
                         organism = synthetic construct
SEQUENCE: 96
acttactacc cgagtaattg cccagcatta caaagttttc aactattccc gtatgtagca    60
attactcctc taaagcacgt ataacgaagg gggaaccgaa ctaaaaagta aactctttca   120
agatcggaag agcg                                                    134

SEQ ID NO: 97            moltype = DNA  length = 133
FEATURE                  Location/Qualifiers
misc_feature             1..133
                         note = Exemplary R2 read
source                   1..133
                         mol_type = other DNA
                         organism = synthetic construct
SEQUENCE: 97
agtatgtatg cgagtattgc ccaggcaagc tcctgtgcgc atcataatca cggctattaa    60
tccccaaccc acgttgctct ctttagcgct tataccgmac tagaggtaca ctttattcca   120
gatcggaaga gcg                                                     133

SEQ ID NO: 98            moltype = DNA  length = 134
FEATURE                  Location/Qualifiers
misc_feature             1..134
                         note = Exemplary R2 read
source                   1..134
                         mol_type = other DNA
                         organism = synthetic construct
SEQUENCE: 98
agggtcttgt cgagtaattg cccagaaagct ttaaccgaac tactaggttc tgactcatcc   60
catataagaa atccatcctt tcgcactttg tcctaagaga tcggaagagc gtcgtgtatg  120
gaaagagtgt agaa                                                    134

SEQ ID NO: 99            moltype = DNA  length = 134
FEATURE                  Location/Qualifiers
misc_feature             1..134
                         note = Exemplary R2 read
source                   1..134
                         mol_type = other DNA
                         organism = synthetic construct
SEQUENCE: 99
acccccccac cgagtaattg cccaggcatt ttcaattcgg ttctacccga actactaggt    60
ttggtttggt cccatataag aaaaccccct tcaggtacag gagtgtccga gatcggaaga  120
gcgtcgtgtt ggga                                                    134

SEQ ID NO: 100           moltype = DNA  length = 134
FEATURE                  Location/Qualifiers
misc_feature             1..134
                         note = Exemplary R2 read
source                   1..134
                         mol_type = other DNA
                         organism = synthetic construct
SEQUENCE: 100
gcaacacgtt caagtaattg cccagtgcgt gagtgtatta acacatgaac gcagttcaac    60
actaccagtt acctgggaat tcataagagt cacggcccga actactaggt taattcgtcc   120
cccatataag aaac                                                    134

SEQ ID NO: 101           moltype = DNA  length = 132
FEATURE                  Location/Qualifiers
misc_feature             1..132
                         note = Exemplary R2 read
source                   1..132
                         mol_type = other DNA
                         organism = synthetic construct
SEQUENCE: 101
cattagttag cgagtattgc ccagccttat aagccgmcta ctaggttccc ctcggcccca    60
tataagamag attaattttg caagcagatg ttcgcagatc ggaagagcgt cgtgtatcga  120
aagactatac at                                                      132

SEQ ID NO: 102           moltype = DNA  length = 134
FEATURE                  Location/Qualifiers
misc_feature             1..134
```

```
                        note = Exemplary R2 read
source                  1..134
                        mol_type = other DNA
                        organism = synthetic construct
SEQUENCE: 102
aggtggataa cgagtaattg cccagtatca gcatccgaac tactaggttt ttctaaggcc    60
catataagaa aatagtaaag tgttcttaac gctccttaga tcggaagagc gtcgtgtagg   120
gaaatagtgt agat                                                     134

SEQ ID NO: 103          moltype = DNA  length = 134
FEATURE                 Location/Qualifiers
misc_feature            1..134
                        note = Exemplary R2 read
source                  1..134
                        mol_type = other DNA
                        organism = synthetic construct
SEQUENCE: 103
atcgatcacc cgagtaattg cccagcaagt cctattatta tacccccac gcatcccgtt    60
tcaccaaacc gaagagtata acctacatcg cctccccgaa ctactaggtt gaacctttgc   120
ccatataaga aatt                                                     134

SEQ ID NO: 104          moltype = DNA  length = 134
FEATURE                 Location/Qualifiers
misc_feature            1..134
                        note = Exemplary R2 read
source                  1..134
                        mol_type = other DNA
                        organism = synthetic construct
SEQUENCE: 104
atagtcacaa acgagtaatt gcccagttaa acttatgcct cttcccgaac tttccgaact    60
actaggttat agcccaaccc atataagaaa ttggagagtg tcgcgttgac tatcagagat   120
cggaagagcg tcgt                                                     134

SEQ ID NO: 105          moltype = DNA  length = 13
FEATURE                 Location/Qualifiers
misc_feature            1..13
                        note = Exemplary capture sequence
source                  1..13
                        mol_type = other DNA
                        organism = synthetic construct
SEQUENCE: 105
cccatataag aaa                                                       13

SEQ ID NO: 106          moltype = DNA  length = 22
FEATURE                 Location/Qualifiers
misc_feature            1..22
                        note = Portion of exemplary anti-target sequence
source                  1..22
                        mol_type = other DNA
                        organism = synthetic construct
SEQUENCE: 106
cggagatgtg tataagagac ag                                             22
```